(12) United States Patent
Bode et al.

(10) Patent No.: US 8,501,658 B2
(45) Date of Patent: Aug. 6, 2013

(54) ENANTIOSELECTIVE REACTIONS CATALYZED BY CHIRAL TRIAZOLIUM SALTS

(75) Inventors: Jeffrey Bode, Santa Barbara, CA (US); Ming He, Goleta, CA (US); Justin Struble, Urbana, IL (US)

(73) Assignee: The Regents of the University of California, Oakland, CA (US)

( * ) Notice: Subject to any disclaimer, the term of this patent is extended or adjusted under 35 U.S.C. 154(b) by 711 days.

(21) Appl. No.: 12/297,858

(22) PCT Filed: Apr. 23, 2007

(86) PCT No.: PCT/US2007/067236
§ 371 (c)(1),
(2), (4) Date: Feb. 17, 2010

(87) PCT Pub. No.: WO2007/124494
PCT Pub. Date: Nov. 1, 2007

(65) Prior Publication Data
US 2010/0210452 A1  Aug. 19, 2010

Related U.S. Application Data

(60) Provisional application No. 60/793,757, filed on Apr. 21, 2006.

(51) Int. Cl.
*B01J 31/18* (2006.01)
*C07D 265/28* (2006.01)
*C07D 211/72* (2006.01)

(52) U.S. Cl.
USPC ............................. 502/167; 544/99; 546/301

(58) Field of Classification Search
None
See application file for complete search history.

(56) References Cited

U.S. PATENT DOCUMENTS 6,784,323 B2  8/2004  MacMillan
6,900,357 B2  5/2005  MacMillan et al.

OTHER PUBLICATIONS

Sohn et al. Organic Letters. 2005, vol. 7, No. 18, pp. 3873-3876.*
Berge, S. et al., "Pharmaceutical Salts." *Journal of Pharmaceutical Sciences.* vol. 66, pp. 1-19 (1977).
Breslow, R., "On the Mechanism of Thiamine Action. IV. Evidence from Studies on Model Systems." *J. Am. Chem. Soc.*, vol. 80, pp. 3719-3725 (1958).
Burnstein, C. et al., "Organocatalyzed Conjugate Umpolung of α.,β-Unsaturated Aldehydes for the Synthesis of γ-Butyrolactones." *Angew. Chem. Int. Ed.*, vol. 43, pp. 6205-6208 (2004).
Chan, A. et al., "Conversion of α, β-Unsaturated Aldehydes into Saturated Esters: An Umpolung Reaction Catalyzed by Nucleophilic Carbenes." *Organic Letters.*, vol. 7, No. 5, pp. 905-908 (2005).
Christmann, M. "New Developments in the Asymmetric Stetter Reaction." *Angew. Chem. Int. Ed.*, vol. 44, pp. 2632-2364 (2005).
Enders, D. et al., "The First Asymmetric Intramolecular *Stetter* Reaction." *Helvetica Chimica Acta*, vol. 76, pp. 1899-1902 (1996).
Enders, D. et al., "An Efficient Nucleophilic Carbene Catalyst for the Asymmetric Benzoin Condensation." *Angew. Chem. Int. Ed.*, vol. 41, pp. 1743-1745 (2002).
Enders, D. et al., "Nucleophilic Carbenes in Asymmetric Organocatalysis." *Acc. Chem. Res.*, vol. 37, pp. 534-541 (2004).
Johnson, J.S., "Catalyzed Reactions of Acyl Anion Equivalents." *Angew. Chem. Int. Ed.*, vol. 43, 1326-1328 (2004).
Kerr, M. et al., "Enantioselective Synthesis of Quaternary Stereocenters via a Catalytic Asymmetric Stetter Reaction." *J. Am. Chem. Soc.*, vol. 126, pp. 8876-8877 (2004).
Maehr, H., "A Proposed New Convention for Graphic Presentation of Molecular Geometry and Topography." *Journal of Chemical Education*, vol. 62, pp. 114-120 (1985).
Reynolds, N. et al., "Conversion of α-Haloaldehydes into Acylating Agents by an Internal REdox Reaction Catalyzed by Nucleophilic Carbenes." *J. Am. Chem. Soc.*,vol. 126, pp. 9518-9519 (2004).
Zeitler, K., "Extending Mechanistic Routes in Heterazolium Catalysis-Promising Concepts for Versatile Synthetic Methods." *Angew. Chem. Int. Ed.*, vol. 44, pp. 7506-7510 (2005).
Alaniz, J. et al., "A Highly Enantio- and Diastereoselective Catalytic Intramolecular Stetter Reaction." *Journal American Chemical Society Articles.* (Published on Web) (2004).
Berry, C. et al., "Inverse electron-demand aza-[4+2] cycloaddition reactions of allenamides." *Tetrahedron.* vol. 60, pp. 7629-7636 (2004).
Boger, D. et al., "Inverse Electron Demand Diels-Alder Reactions of N-Sulfonyl α, β-Unstaturated Imines: A General Approach to Implementation of the 4π Participation of 1-Aza-1, 3-butadienes in Diels-Alder Reactions." *Journal American Chemical Society.* vol. 113, pp. 1713-1729 (1991).
Clark, R. et al., "Diastereoselective Diels-Alder Reactions of N-Sulfonyl-1 aza-1,3-butadienes with Optically Active Enol Ethers: An Asymmetric Variant of the 1-Azadiene Diels-Alder Reaction." *Journal American Chemical Society Articles.* (Published on Web) (2006).
Chow, K. et al., "Catalytic Generation of Activated Carboxylates: Direct, Stereoselective Synthesis of β-Hydroxyesters from Epoxyaldehydes." *Journal American Chemistry Society.* vol. 26, pp. 8126-8127 (2004).
He, M. et al., "Catalytic Synthesis of γ-Lactams via Direct Annulations of Enals and N-Sulfonylimines." *Organic Letters.* vol. 7, No. 14, pp. 3131-3134 (2005).
Kerr, M. et al., "A Highly Enantioselective Catalytic Intramolecular Stetter Reaction." *Journal American Chemical Society.* vol. 124, pp. 10298-10299 (2002).
Kerr, M. et al., "An Efficient Synthesis of Achiral and Chiral 1,2,4-Triazolium Salts: Bench Stable Precursors for N-Heterocyclic Carbenes." *Journal American Chemical Society Note.* (Published on Web) (2005).

(Continued)

*Primary Examiner* — Melvin Curtis Mayes
*Assistant Examiner* — Yun Qian
(74) *Attorney, Agent, or Firm* — Morgan, Lewis & Bockius LLP; Jeffry S. Mann

(57) ABSTRACT

This invention provides a convenient method for converting imines and other electrophiles into heterocyclic ring systems. The process does not require the use of metallic reagents, and is catalyzed by an organic heterocyclic carbene catalyst. Accordingly, it produces the desired compounds without the concomitant production of a large volume of metallic waste. Chiral heterocyclic carbene catalysts of the invention and methods of using these catalysts produce chiral heterocycles in high enantiomeric and diastereomeric excess.

35 Claims, No Drawings

(56) References Cited

OTHER PUBLICATIONS

Chow, K. et al., "Catalytic Generation of Activated Carboxylates: Direct, Stereoselective Synthesis of β-Hydroxyesters from Epoxyaldehydes." *Journal American Chemistry Society.* vol. 26, pp. 8126-8127 (2004).

He, M. et al., "Catalytic Synthesis of γ-Lactams via Direct Annulations of Enals and N-Sulfonylimines." *Organic Letters.* vol. 7, No. 14, pp. 3131-3134 (2005).

Kerr, M. et al., "A Highly Enantioselective Catalytic Intramolecular Stetter Reaction." *Journal American Chemical Society.* vol. 124, pp. 10298-10299 (2002).

Kerr, M. et al., "An Efficient Synthesis of Achiral and Chiral 1,2,4-Triazolium Salts: Bench Stable Precursors for N-Heterocyclic Carbenes." *Journal American Chemical Society Note.* (Published on Web) (2005).

Knight, R. et al., "Comparison of chiral thiazolium and triazolium salts as asymmetric catalysts for the benzoin condensation." *J. Chem. Soc., Perkin Trans 1.* (1998).

Liu, Q. et al., "Asymmetric Synthesis of Hydrobenzofuranones via Desymmetrization of Cyclohexadienones Using the Intramolecular Stetter Reaction." *Journal American Chemical Society Communications.* (Published on Web) (2006).

Reynolds, N. et al., "Enantioselective Protonation of Catalytically Generated Chiral Enolates as an Approach to the Synthesis of α-Chloroesters." Journal American Chemical Society. (Published on Web) (2005).

Sohn, S. et al., "N-Heterocyclic Carbene-Catalyzed Generation of Homoenolates: γ-Butyrolactones by Dirct Annulations of Enals and Aldehydates." *Journal American Chemical Society.* vol. 126, pp. 14370-14371 (2004).

Sohn, S. et al., "Catalytic Generation of Activated Carboxylates from Enals: A Product-Determining Role for the Base." *Organic Letters.* vol. 7, No. 18, pp. 3873-3876 (2005).

\* cited by examiner

ENANTIOSELECTIVE REACTIONS CATALYZED BY CHIRAL TRIAZOLIUM SALTS

CROSS-REFERENCE TO RELATED APPLICATIONS

This application claims priority to U.S. Provisional Patent Application No. 60/793,757 filed Apr. 21, 2006, which is incorporated herein by reference in its entirety for all purposes.

FIELD OF THE INVENTION

This invention relates to methods suitable for the preparation of chiral dihydropyridinones as well as chiral non-metal based catalysts useful in the methods of the invention.

BACKGROUND OF THE INVENTION

Carbon—carbon bond forming processes mediated by N-heterocyclic carbene organocatalysts have witnessed recent, impressive progress in the discovery of new reaction manifolds and the development of asymmetric processes. (Zeitler, *Angew. Chem. Int. Ed.,* 44:7506-7510, (2005); Johnson, J. S., *Angew. Chem. Int. Ed.,* 43:1326-1328 (2004); Christman, M., *Angew. Chem. Int. Ed.,* 44:2632-2634, (2005); Enders, et al, *Acc. Chem. Res.,* 37:534, (2004)). Notable advances include new chiral triazolium catalysts for enantioselective intermolecular homodimerization of aryl aldehydes (Enders, et al., *Angew. Chem. Mt. Ed,* 41: 1743 (2002)), intramolecular aldehyde-ketone benzoin cyclizations and intramolecular Stetter reactions, (Kerr, et al., *J. Am. Chem. Soc.,* 124:10298-10299, (2002); Kerr, et al., *J. Am. Chem. Soc.,* 126:8876-8877 (2004); Read de Alaniz, et al., *J. Am. Chem. Soc.,* 127:6284-6289, (2005); Enders, et al., *Helv. Chim. Acta,* 76:1899-1902, (1996)). Efforts have focused on extending the mechanistic pathways available to the key "Breslow intermediate" formed by the nucelophilic addition of the carbene catalyst to the aldehydes (Breslow, R. J., *Am. Chem. Soc.,* 80: 3719-3725, (1958)). This strategy was applied to the catalytic generation of activated carboxylates (Chow, *J. Am. Chem. Soc.,* 126:8126-8127, (2004); Sohn, et al., *Org. Lett.,* 7:3873-3876, (2005); Reynolds, et al., *J. Am. Chem. Soc.,* 126:9518-9519, (2004); Reynold, et al., *J. Am. Chem. Soc.,* 127:16406-16407, (2005); Chan, et al.; *Org. Lett.,* 7: 905-908, (2005)), and to novel carbon—carbon bond forming processes that proceed via a formal homoenolate intermediate (Sohn, et al., *J. Am. Chem. Soc.,* 126:14370-14371, (2004); Burstein, et al., *Angew. Chem. Int. Ed.,* 43:6205-6208, (2004); He, et al., *Org. Lett.,* 7:3131-3134, (2005)).

A cost-efficient, scalable method for organocatalysis through a N-heterocyclic-carbene catalyzed Diels-Alder reaction would be a significant addition to the array of available annulation chemistries. Furthermore, a process that provided a highly enantioselective organo-catalyzed intermolecular cross-coupling reaction would be operationally friendly and would not require heating, cooling, complex workup or the use of other reagents. The current invention addresses this and other needs.

SUMMARY OF THE INVENTION

This invention provides a new class of triazolium catalysts and their utility for the diastereo- and enantioselective synthesis of heterocyclic compounds, particularly pyridinones and pyranones.

Enantioselective and stereoselective organic reactions catalyzed by small organic molecules are an increasingly important method for the synthesis of chiral molecules. This strategy has the advantage that the small organic catalysts tend to be less expensive and less toxic than metal-based catalysts and are easier to remove from the reaction mixtures. These "organocatalysts" also have the advantage that they often operate in the presence of complex functional groups and under more user-friendly reaction conditions than metal catalyzed processes. The products from these organocatalytic reactions find widespread use in the manufacture of pharmaceuticals, pesticides, fine chemicals, fragrances, natural products, and materials.

Thus, in a first aspect, the current invention provides a method for preparing a chiral heterocycle described herein. In an exemplary embodiment, the chiral heterocycle has a formula which is a member selected from:

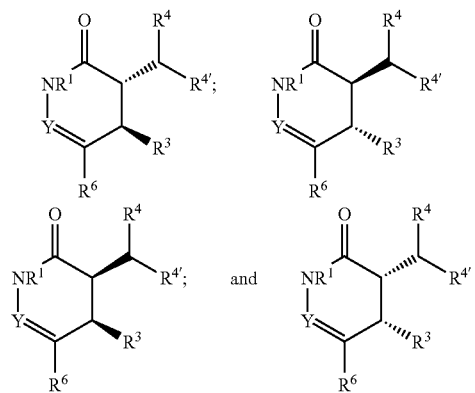

wherein $R^1$ is a member selected from $C(O)R^7$, $S(O)_2R^7$, $P(O)(R^7)_2$ and $P(O)(OR^7)_2$, wherein each $R^7$ is a member independently selected from substituted or unsubstituted alkyl, substituted or unsubstituted heteroalkyl, substituted or unsubstituted aryl, substituted or unsubstituted heteroaryl substituted or unsubstituted cycloalkyl and substituted or unsubstituted heterocycloalkyl.

Y is a member selected from $CR^2$ and $NO^-$. $R^2$, $R^4$, $R^{4'}$ and $R^6$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl. $R^3$ is a member selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl. In an exemplary embodiment, Y is $CR^2$.

The method includes contacting an imine described herein and an aldehyde described herein and an organic catalyst described herein. In an exemplary embodiment, the imine has the formula:

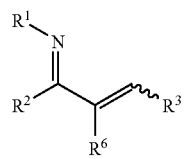

and the aldehyde has the formula:

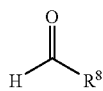

wherein $R^8$ is a member selected from substituted or unsubstituted unsaturated alkyl, substituted or unsubstituted unsaturated heteroalkyl substituted or unsubstituted cycloalkyl and substituted or unsubstituted heterocycloalkyl with a heterocyclic organic catalyst described herein. In an exemplary embodiment, the organic catalyst has the formula:

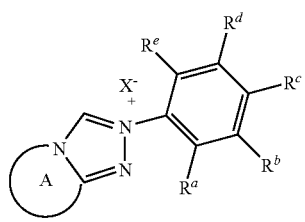

I

In Formula I, A is present or absent and, when present, is a ring system selected from substituted or unsubstituted cycloalkyl and substituted or unsubstituted heterocycloalkyl, $R^a$, $R^b$, $R^c$, $R^d$ and $R^e$ are members independently selected from H, substituted or unsubstituted alkyl and substituted or unsubstituted heteroalkyl, and $X^-$ is an anion under conditions appropriate to prepare said chiral heterocycle.

Thus, in a second aspect, the current invention provides a method for preparing a chiral heterocycle described herein. In an exemplary embodiment, the chiral heterocycle has a formula which is a member selected from:

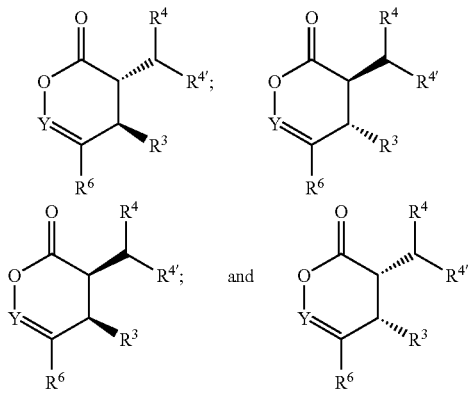

wherein $R^1$ is a member selected from $C(O)R^7$, $S(O)_2R^7$, $P(O)(R^7)_2$ and $P(O)(OR^7)_2$, wherein each $R^7$ is a member independently selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl.

Y is a member selected from $CR^2$ and $NO^-$. $R^2$, $R^4$, $R^{4'}$ and $R^6$ are members independently selected from H, substituted or unsubstituted alkyl, substituted or unsubstituted heteroalkyl, substituted or unsubstituted aryl, substituted or unsubstituted heteroaryl, substituted or unsubstituted hetero- cycloalkyl. $R^3$ is a member selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl.

The method includes contacting an enone described herein and an aldehyde described herein and an organic catalyst described herein. In an exemplary embodiment, the enone has the formula:

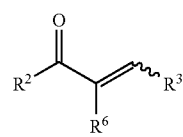

and the aldehyde has the formula:

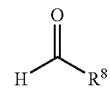

wherein $R^8$ is a member selected from substituted or unsubstituted unsaturated alkyl, substituted or unsubstituted unsaturated heteroalkyl, substituted or unsubstituted cycloalkyl and substituted or unsubstituted heterocycloalkyl with a heterocyclic organic catalyst described herein. In an exemplary embodiment, the organic catalyst has the formula:

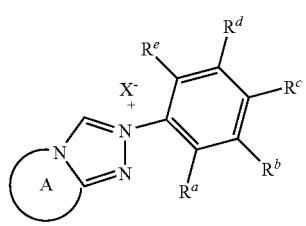

I

In Formula I, A is present or absent and, when present, is a ring system selected from substituted or unsubstituted cycloalkyl and substituted or unsubstituted heterocycloalkyl, $R^a$, $R^b$, $R^c$, $R^d$ and $R^e$ are members independently selected from H, substituted or unsubstituted alkyl and substituted or unsubstituted heteroalkyl, and $X^-$ is an anion under conditions appropriate to prepare said chiral heterocycle.

In a third aspect, the invention provides a compound of Formula I:

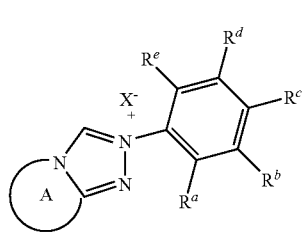

I wherein A is a ring system selected from substituted or unsubstituted cycloalkyl and substituted or unsubstituted heterocycloalkyl. $R^a$, $R^b$, $R^c$, $R^d$ and $R^e$ are members independently selected from H, substituted or unsubstituted alkyl and substituted or unsubstituted heteroalkyl and $X^-$ is an anion.

In another aspect, the invention provides a method for preparing a chiral heterocycle having the formula:

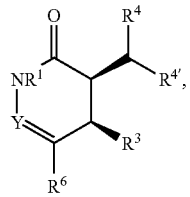

involving contacting an imine described herein and an aldehyde described herein and an organic catalyst with a structure according to the following formula:

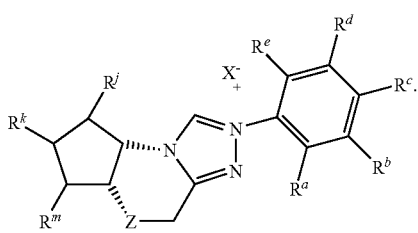

In an exemplary embodiment, the organic catalyst has a structure according to the following formula:

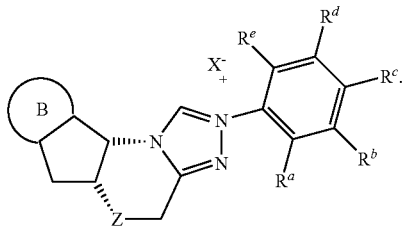

In an exemplary embodiment, the organic catalyst has a structure according to the following formula:

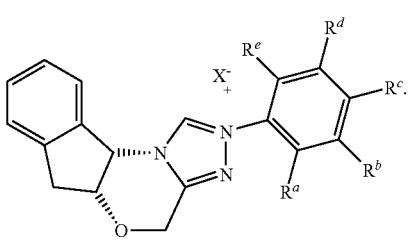

In an exemplary embodiment, the compound has a formula which is a member selected from:

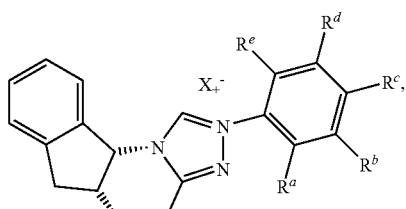

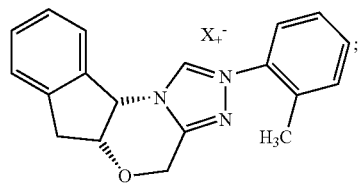

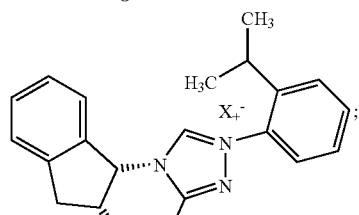

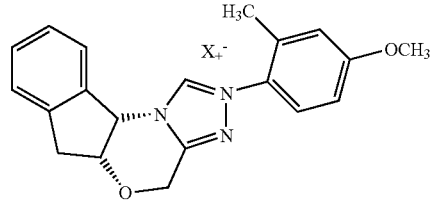

and

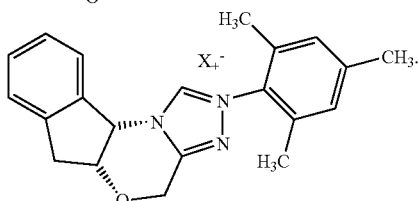

In an exemplary embodiment, the method produces the product with an enantiomeric excess of a member selected from about 80% ee (de) to about 99% ee (de), from about 90% ee (de) to about 99% ee (de), from about 95% ee (de) to about 99% ee (de), still more preferably from about 98% ee (de) to about 99% ee (de), still more preferably from about 99% ee (de) to about 99.9% ee(de).

In another aspect, the invention provides a method for preparing a chiral heterocycle having the formula:

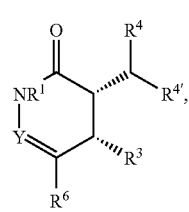

involving contacting an imine described herein and an aldehyde described herein and an organic catalyst with a structure according to the following formula:

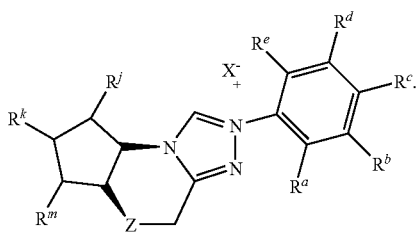

In an exemplary embodiment, the organic catalyst has a structure according to the following formula:

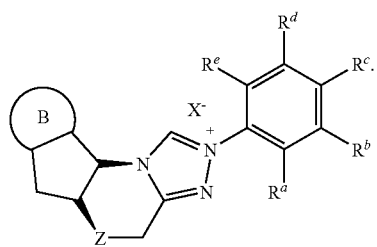

In an exemplary embodiment, the organic catalyst has a structure according to the following formula:

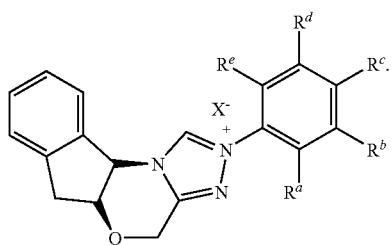

In an exemplary embodiment, the compound has a formula which is a member selected from:

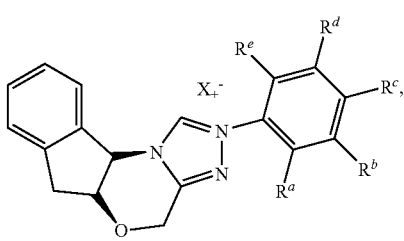

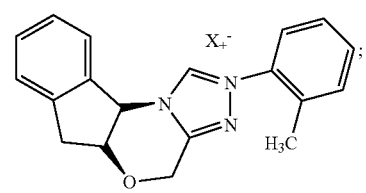

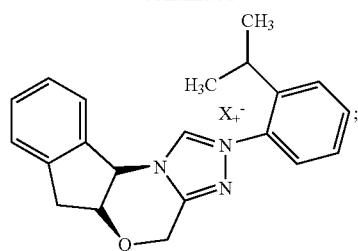

In an exemplary embodiment, the method produces the product with an enantiomeric excess of a member selected from about 80% ee (de) to about 99% ee (de), from about 90% ee (de) to about 99% ee (de), from about 95% ee (de) to about 99% ee (de), still more preferably from about 98% ee (de) to about 99% ee (de), still more preferably from about 99% ee (de) to about 99.9% ee(de).

In another aspect, the invention provides a method for preparing a chiral heterocycle having the formula:

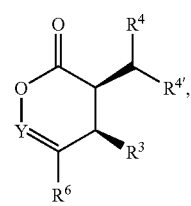

involving contacting an enone described herein and an aldehyde described herein and an organic catalyst with a structure according to the following formula:

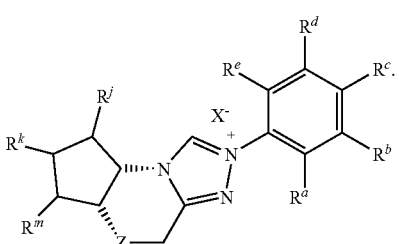

In an exemplary embodiment, the organic catalyst has a structure according to the following formula:

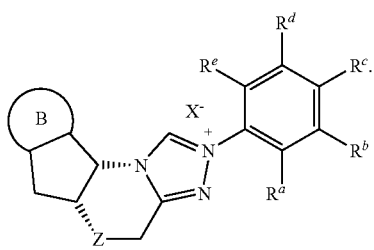

In an exemplary embodiment, the organic catalyst has a structure according to the following formula:

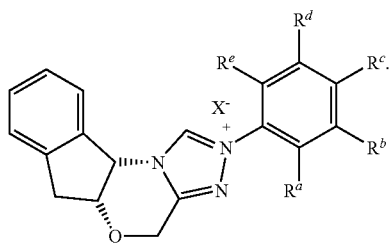

In an exemplary embodiment, the compound has a formula which is a member selected from:

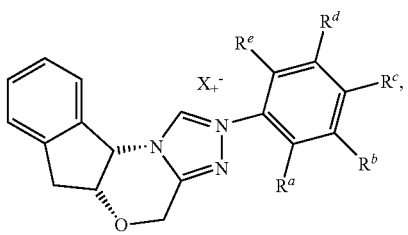

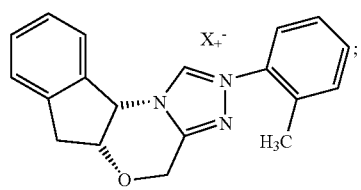

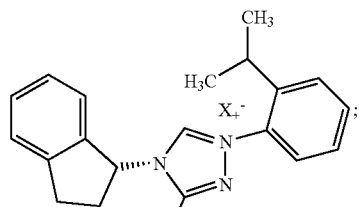

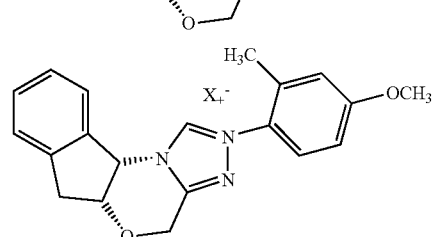

and

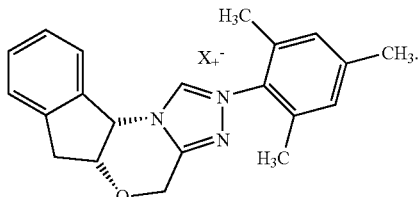

In an exemplary embodiment, the method produces the product with an enantiomeric excess of a member selected from about 80% ee (de) to about 99% ee (de), from about 90% ee (de) to about 99% ee (de), from about 95% ee (de) to about 99% ee (de), still more preferably from about 98% ee (de) to about 99% ee (de), still more preferably from about 99% ee (de) to about 99.9% ee(de).

In another aspect, the invention provides a method for preparing a chiral heterocycle having the formula:

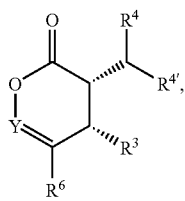

involving contacting an enone described herein and an aldehyde described herein and an organic catalyst with a structure according to the following formula:

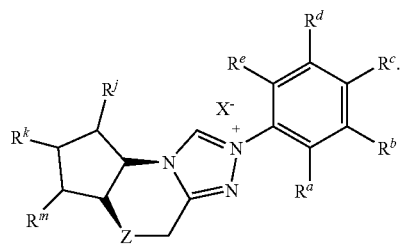

In an exemplary embodiment, the organic catalyst has a structure according to the following formula:

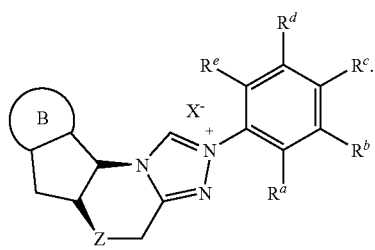

In an exemplary embodiment, the organic catalyst has a structure according to the following formula:

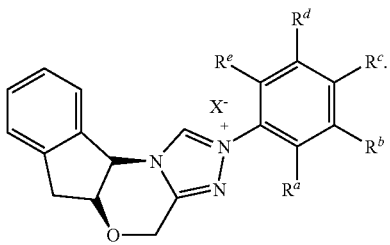

In an exemplary embodiment, the compound has a formula which is a member selected from:

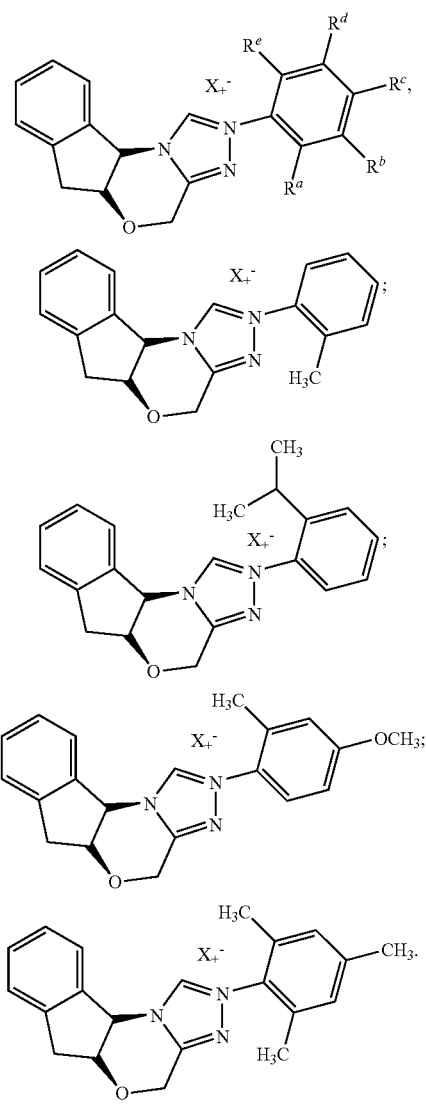

In an exemplary embodiment, the method produces the product with an enantiomeric excess of a member selected from about 80% ee (de) to about 99% ee (de), from about 90% ee (de) to about 99% ee (de), from about 95% ee (de) to about 99% ee (de), still more preferably from about 98% ee (de) to about 99% ee (de), still more preferably from about 99% ee (de) to about 99.9% ee(de).

DETAILED DESCRIPTION OF THE INVENTION

Definitions

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, and —CH═CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', —NR'R", —SR', -halogen, —SiR'R"R''', —OC(O)R', —C(O)R', —CO$_2$R', —CONR'R", —OC(O)NR'R", —NR"C(O)R', —NR'—C(O) NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R"" and are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula 13 (CRR')$_s$—X—(CR"R")$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

Despite the recognized utility of dihydropyridinones, there are few methods for their preparation in either racemic or enantiomerically pure form. The existing, uncatalyzed methods require high pressure or temperatures and are limited in substrate scope. To access enantiomerically pure products, expensive chiral auxiliaries must be employed, a process that adds complexity, cost, and several reaction steps to the overall process.

The present invention provides innovations in both the catalyst and the mechanistic pathway for preparation of enantiomerically and diastereomerically enriched dihydropyridinones.

The Methods

In a first aspect, the present invention provides a method for preparing a dihydropyridinone. The method includes performing an organo-catalyzed Diels-Alder reaction, forming the dihydropyridinone ring system. The Diels-Alder reaction includes coupling of a diene (e.g., an alpha-beta unsaturated imine) and an electrophilic reactant (e.g., an alpha-beta unsaturated aldehyde) in the presence of a heterocyclic organic catalyst. Exemplary conditions and substrates are set forth herein.

Imine

In one embodiment, a diene reactant is useful in the methods described herein. In an exemplary embodiment, the diene reactant is an alpha-beta unsaturated imine of Formula II:

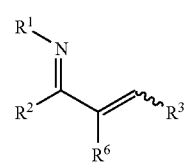

II

In Formula II, $R^1$ is a member selected from $C(O)R^7$, $S(O)_2R^7$, $P(O)(R^7)_2$ and $P(O)(OR^7)_2$, wherein each $R^7$ is a member independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In an exemplary embodiment, each $R^7$ is a member independently selected from substituted or unsubstituted alkyl, substituted or unsubstituted heteroalkyl, substituted or unsubstituted aryl and substituted or unsubstituted heteroaryl. $R^2$ and $R^6$ are members independently selected from H, substituted or unsubstituted alkyl, substituted or unsubstituted heteroalkyl, substituted or unsubstituted aryl, substituted or unsubstituted heteroaryl substituted or unsubstituted cycloalkyl and substituted or unsubstituted heterocycloalkyl. $R^3$ is a member selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl.

In an exemplary embodiment, $R^2$ is a member selected from substituted or unsubstituted alkyl, substituted or unsubstituted heteroalkyl, substituted or unsubstituted aryl, substituted or unsubstituted heteroaryl substituted or unsubstituted cycloalkyl and substituted or unsubstituted heterocycloalkyl. In an exemplary embodiment, $R^2$ is a member selected from substituted or unsubstituted alkyl, substituted or unsubstituted aryl, substituted or unsubstituted heteroaryl. In an exemplary embodiment, $R^2$ is a member selected from substituted or unsubstituted methyl, substituted or unsubstituted hexyl, substituted or unsubstituted phenyl, and substituted or unsubstituted furyl. In an exemplary embodiment, $R^2$ is a member selected from methyl, c-hexyl, phenyl, halogen substituted phenyl, p-bromophenyl, m-bromophenyl, o-bromophenyl, p-chlorophenyl, m-chlorophenyl, o-chlorophenyl, p-fluorophenyl, m-fluorophenyl, o-fluorophenyl, p-iodophenyl, m-iodophenyl, o-iodophenyl, and furyl. In an exemplary embodiment, $R^2$ is p-bromophenyl. In an exemplary embodiment, $R^2$ is H.

In an exemplary embodiment, $R^3$ is a member selected from substituted and unsubstituted alkyl, substituted and unsubstituted heteroalkyl, substituted and unsubstituted cycloalkyl, substituted and unsubstituted heterocycloalkyl, substituted and unsubstituted aryl and substituted and unsubstituted heteroaryl. In an exemplary embodiment, $R^3$ is a member selected from substituted and unsubstituted alkyl and substituted and unsubstituted aryl. In an exemplary embodiment, $R^3$ is a member selected from substituted or unsubstituted methyl, substituted or unsubstituted propyl, substituted or unsubstituted hexyl, substituted or unsubstituted furyl, substituted or unsubstituted phenyl, and substituted or unsubstituted toluoyl. In an exemplary embodiment, $R^3$ is a member selected from methyl, propyl, isopropyl, c-hexyl, phenyl, p-methoxyphenyl, m-methoxyphenyl, o-methoxyphenyl, p-acetylphenyl, m-acetylphenyl, o-acetylphenyl, alkylcarbonylphenyl, alkyl substituted phenyl, p-toluoyl, m-toluoyl, o-toluoyl, p-bromophenyl, m-bromophenyl, o-bromophenyl, p-chlorophenyl, m-chlorophenyl, o-chlorophenyl, p-fluorophenyl, m-fluorophenyl, o-fluorophenyl, p-iodophenyl, m-iodophenyl, o-iodophenyl.

In an exemplary embodiment, $R^6$ is H.

In an exemplary embodiment, $R^7$ is substituted and unsubstituted aryl. In an exemplary embodiment, $R^7$ is a member selected from p-methoxyphenyl, o-methoxyphenyl, m-methoxyphenyl, and phenyl.

In a preferred embodiment, the imine has a formula which is a member selected from:

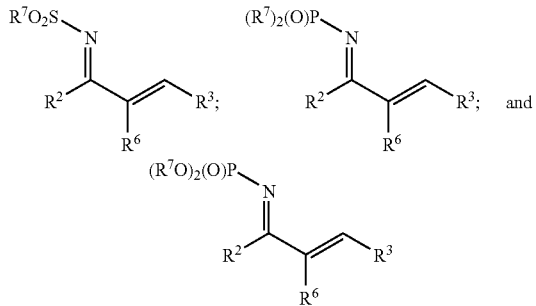

in which $R^2$, $R^3$ and $R^6$ are as defined herein.

Diene reactants or electrophiles other than imines are useful to practice the method of the invention. Exemplary electrophiles with an alternative functional group include unsaturated ketones and nitroalkenes. In an exemplary embodiment the electrophile is a member selected from:

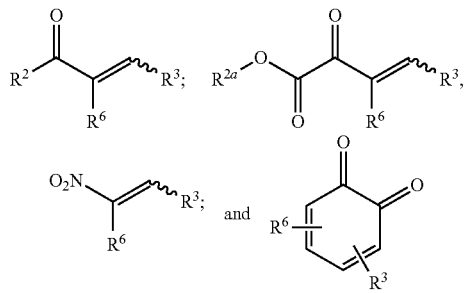

in which $R^2$, $R^3$ and $R^6$ are as defined above. $R^{2a}$ is a member selected from substituted and unsubstituted alkyl, substituted and unsubstituted heteroalkyl, substituted and unsubstituted cycloalkyl, substituted and unsubstituted heterocycloalkyl, substituted and unsubstituted aryl and substituted and unsubstituted heteroaryl. In an exemplary embodiment, $R^{2a}$ is substituted and unsubstituted alkyl. In an exemplary embodiment, $R^{2a}$ is a member selected from methyl, ethyl, propyl, isopropyl and butyl. In an exemplary embodiment, $R^{2a}$ is ethyl.

In an exemplary embodiment, $R^3$ is $—C(O)OR^{3a}$, wherein $R^{3a}$ is a member selected from substituted and unsubstituted alkyl, substituted and unsubstituted heteroalkyl, substituted and unsubstituted cycloalkyl, substituted and unsubstituted heterocycloalkyl, substituted and unsubstituted aryl and substituted and unsubstituted heteroaryl. In an exemplary embodiment, $R^{3a}$ is substituted and unsubstituted alkyl. In an exemplary embodiment, $R^{3a}$ is a member selected from methyl, ethyl, propyl, isopropyl and butyl. In an exemplary embodiment, $R^{3a}$ is methyl.

Aldehyde

According to the methods described herein, the diene reactant (either imine or enone) is contacted with an aldehyde having the formula:

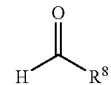

wherein $R^8$ is a member selected from substituted alkyl, substituted or unsubstituted unsaturated alkyl, substituted heteroalkyl, substituted or unsubstituted heteroalkyl, unsaturated heteroalkyl and substituted or unsubstituted heterocycloalkyl.

Preferred aldehydes of the current invention include those in which the aldehyde function is alpha-beta unsaturated. Exemplary aldehydes are members selected from:

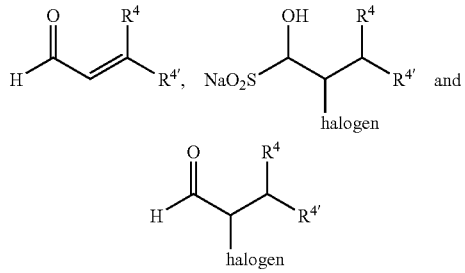

in which $R^4$ and $R^{4'}$ are members independently selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl. In an exemplary embodiment, one of $R^4$ and $R^{4'}$ is H, and the other is substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl. In an exemplary embodiment, one of $R^4$ and $R^{4'}$ is H, and the other is substituted or unsubstituted alkyl, substituted or unsubstituted O-tertbutylsilyl, substituted or unsubstituted phenyl. In an exemplary embodiment, one of $R^4$ and $R^{4'}$ is H, and the other is methyl, nonyl, O-tertbutylsilyl and phenyl.

In another exemplary embodiment, 'halogen' is a member selected from chloro and bromo. In another exemplary embodiment, 'halogen' is chloro. In an exemplary embodiment, $R^4$ is H. In an exemplary embodiment, $R^{4'}$ is H. In an exemplary embodiment, one of $R^4$ and $R^{4'}$ is H, and the other is —C(O)OR$^{4a}$, wherein $R^{4a}$ is a member selected from substituted and unsubstituted alkyl, substituted and unsubstituted heteroalkyl, substituted and unsubstituted cycloalkyl, substituted and unsubstituted heterocycloalkyl, substituted and unsubstituted aryl, substituted or unsubstituted cycloalkyl and substituted and unsubstituted heteroaryl. In an exemplary embodiment, $R^{4a}$ is substituted and unsubstituted alkyl or substituted and unsubstituted phenyl. In an exemplary embodiment, $R^{4a}$ is a member selected from methyl, ethyl, propyl, isopropyl, t-butyl, butyl and phenyl. In an exemplary embodiment, $R^{4a}$ is ethyl or methyl.

In one exemplary embodiment, the aldehyde has the formula:

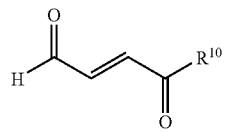

wherein $R^{10}$ is a member selected from OR$^{11}$, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl. $R^{11}$ is substituted or unsubstituted alkyl, substituted or unsubstituted heteroalkyl, substituted or unsubstituted aryl, substituted or unsubstituted heteroaryl and substituted or unsubstituted heterocycloalkyl.

In another exemplary embodiment, $R^8$ includes a substituted cyclopropane moiety. Exemplary aldehydes have the formula:

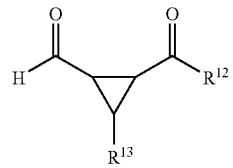

wherein $R^{12}$ is a member selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl. $R^{13}$ is a member selected from H, substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl.

In another exemplary embodiment, the aldehyde includes an alpha-heteroatom. Exemplary aldehydes have the formula:

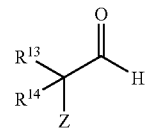

wherein $R^{13}$ and $R^{14}$ are members independently selected from H, halogen, substituted or unsubstituted alkyl, substituted or unsubstituted heteroalkyl, and substituted or unsubstituted heterocycloalkyl. $R^{13}$ and $R^{14}$ are optionally joined to form a 3- to 7-membered ring. Z is a member selected from halogen, OC(O)R$^{15}$, OS(O)$_2$R$^{15}$, OP(O)(R$^{15}$)$_2$ and OR$^{15}$, wherein R$^{15}$ is a member selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl.

Other aldehydes useful in the methods of the invention include:

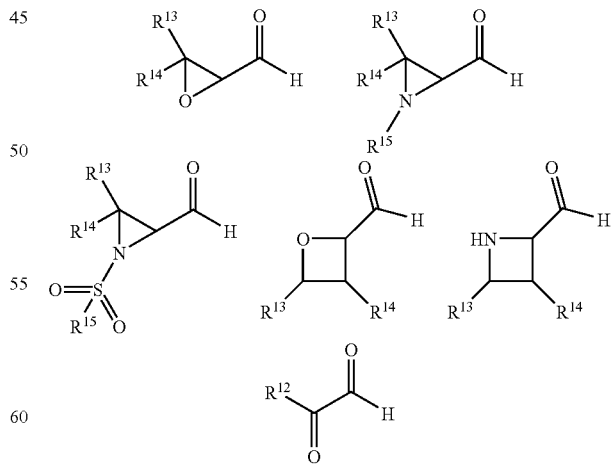

wherein $R^{12}$, $R^{13}$, $R^{14}$ and $R^{15}$ are as defined above.

Catalyst

In a second aspect, the invention provides compounds which have a structure according to Formula I.

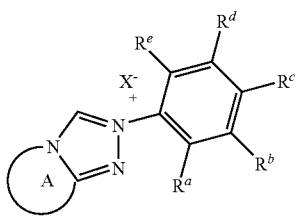

(I)

wherein A is present or absent and, if present, is a ring system selected from substituted or unsubstituted cycloalkyl and substituted or unsubstituted heterocycloalkyl. $R^a$ and $R^e$ are members independently selected from H, halogen, nitro, cyano, substituted or unsubstituted alkyl and substituted or unsubstituted heteroalkyl, substituted or unsubstituted cycloalkyl and substituted or unsubstituted heterocycloalkyl. In an exemplary embodiment, $R^a$ and $R^e$ are members independently selected from H, substituted or unsubstituted alkyl and substituted or unsubstituted heteroalkyl. $R^b$, $R^c$ and $R^d$ are members independently selected from H, halogen, nitro, cyano, substituted or unsubstituted alkyl and substituted or unsubstituted heteroalkyl, substituted or unsubstituted cycloalkyl and substituted or unsubstituted heterocycloalkyl. In an exemplary embodiment, $R^b$, $R^c$ and $R^d$ are members independently selected from H, substituted or unsubstituted alkyl and substituted or unsubstituted heteroalkyl. X is an anion. In an exemplary embodiment, the anion in a organic catalysts described herein is replaced with an H.

These compounds have a wide range of uses. One of these uses is as an organic catalyst for the reactions described herein.

In an exemplary embodiment, there is a proviso that $R^a$ and $R^e$ cannot both be H. In an exemplary embodiment, there is a proviso that $R^a$ and $R^e$ cannot both be halogen if $R^b$, $R^c$ and $R^d$ are halogen. In another exemplary embodiment, both provisos are present.

The triazolium counterion ($X^-$) can be any useful anion. Exemplary counterions include $Cl^-$, $Br^-$, $I^-$, triflate, sulfate, $BF_4^-$, $PF_6^-$, $SbF_6^-$, perchlorate, acetate, and the like.

In an exemplary embodiment, the compound has a structure according to the following formula:

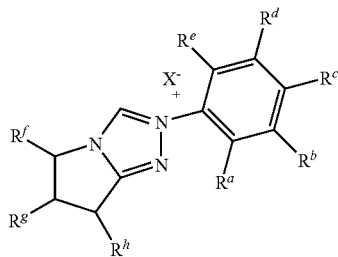

wherein each $R^f$, $R^g$ and $R^h$ are members individually selected from is a member selected from H, substituted or unsubstituted alkyl and substituted or unsubstituted heteroalkyl. The embodiment has the proviso that the proviso that $R^f$ and $R^g$ can be optionally joined to form a five to seven membered ring. The embodiment has the proviso that $R^g$ and $R^h$ can be optionally joined to form a five to seven membered ring. The five to seven membered ring is a member selected from substituted or unsubstituted cycloalkyl, substituted or unsubstituted heterocycloalkyl, substituted or unsubstituted aryl and substituted or unsubstituted heteroaryl. In an exemplary embodiment, said $R^f$, $R^g$ and $R^h$ are H.

In an exemplary embodiment, the compound has a structure according to the following formula:

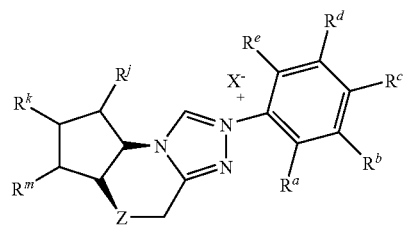

and

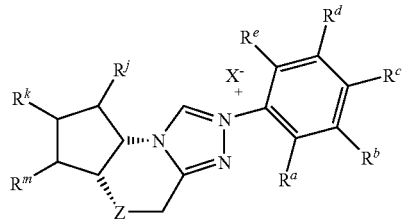

wherein Z is a member selected from O and S. Each $R^j$, $R^k$ and $R^m$ are members individually selected from is a member selected from H, substituted or unsubstituted alkyl and substituted or unsubstituted heteroalkyl. This embodiment has the proviso that $R^j$ and $R^k$ can be optionally joined to form a five to seven membered ring. This embodiment also has the proviso that $R^k$ and $R^m$ can be optionally joined to form a five to seven membered ring. The five to seven membered ring is a member selected from substituted or unsubstituted cycloalkyl, substituted or unsubstituted heterocycloalkyl, substituted or unsubstituted aryl and substituted or unsubstituted heteroaryl.

In another exemplary embodiment, the compound has a structure according to the following formula:

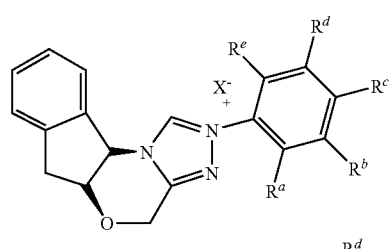

and

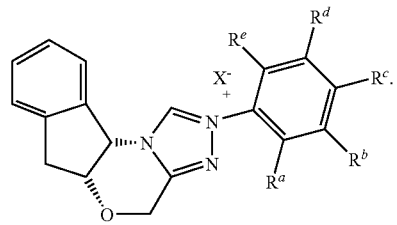

In another exemplary embodiment, $R^a$, $R^c$ and $R^e$ are each methyl. In another exemplary embodiment, $R^a$ and $R^e$ are members independently selected from H, substituted or unsubstituted alkyl and substituted or unsubstituted heteroalkyl. In another exemplary embodiment, $R^b$ is H. In another exemplary embodiment, $R^d$ is H. In another exemplary embodiment, $R^b$ and $R^d$ are H. In another exemplary embodiment, if one member of $R^a$ and $R^e$ is $C_1$-$C_6$ alkyl, then the other member is H. In another exemplary embodiment, $R^a$ and $R^e$ are each independently selected from $C_1$-$C_6$ alkyl. In another exemplary embodiment, $R^e$ is $C_1$-$C_6$ alkyl. In another exemplary embodiment, $R^e$ is a member selected from methyl, ethyl, propyl, isopropyl, butyl, isobutyl, pentyl, isopentyl and hexyl. In another exemplary embodiment, $R^a$, $R^c$ and $R^e$ are each methyl. In another exemplary embodiment, $R^d$ is substituted or unsubstituted heteroalkyl. In another exemplary embodiment, $R^b$ and $R^d$ are H. In another exemplary embodiment, $R^d$ is substituted or unsubstituted methoxy. In another exemplary embodiment, the compound is chiral. In another exemplary embodiment, the compound has a formula selected from:

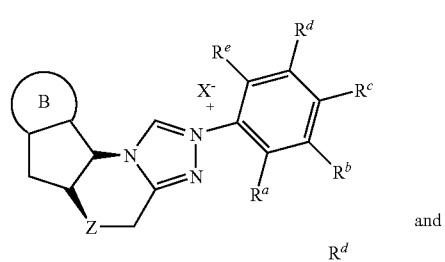

and wherein B is a ring system selected from substituted or unsubstituted aryl and substituted or unsubstituted heteroaryl. Z is a member selected from O and S. In an exemplary embodiment, B is substituted or unsubstituted phenyl.

In another exemplary embodiment, each compound has a formula which is a member selected from:

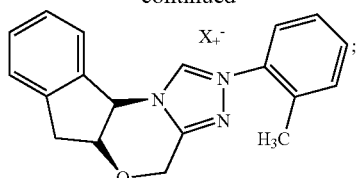

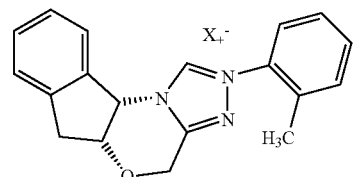

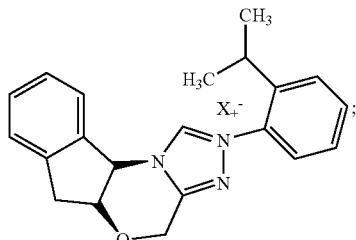

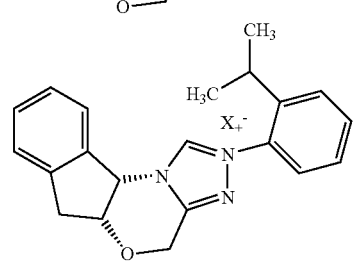

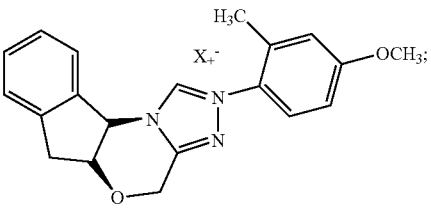

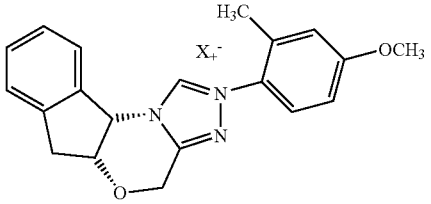

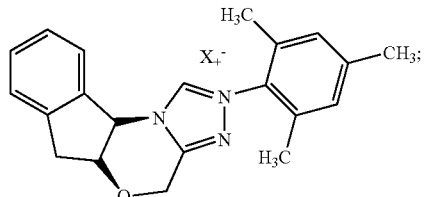

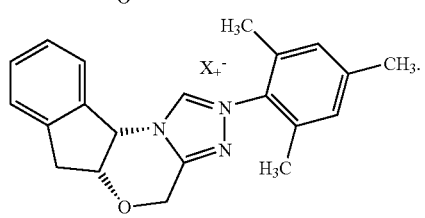

The catalyst is present in the reaction mixture in any useful amount. Determining an appropriate catalyst structure and an effective amount of the catalyst is well within the abilities of those of skill in the art. In an exemplary embodiment, the catalyst is present in the reaction mixture in an amount from about 0.001 equivalents to about 1 equivalent. Generally, it is preferred that the catalyst be present in an amount from about 0.01 equivalent to about 0.5 equivalents, more preferably about 0.05 to about 0.2 equivalents, and even more preferably about 0.1 to about 0.15 equivalents relative to the aldehyde reactant.

Solvent

In an exemplary embodiment, the reactants (e.g., imine and aldehyde) are contacted in the presence of an organic solvent. The method of the invention can be practiced using a variety of protic and aprotic organic solvents. Choice of an appropriate solvent for a particular reaction is well within the abilities of those of skill in the art. Exemplary organic solvents include DMF, ethylacetate (EtOAc), dichloromethane ($CH_2Cl_2$), dicholorethane, benzene, toluene, xylene, dioxane, tert-butyl alcohol, DMSO, acetonitrile ($CH_3CN$), chloroform, tetrahydrofuran (THF) and mixtures thereof. Preferred solvents include mixtures of toluene and THF.

The solvent and substrate are present in essentially any useful ratio. In an exemplary embodiment, the solvent and substrate are present in amounts that provide a substrate solution of from about 0.001 M to about 1 M, preferably, from about 0.01 M to about 0.1 M and, more preferably, from about 0.03 M to about 0.07 M.

Base

In an exemplary embodiment, the reactants are contacted in the presence of a base. In a preferred embodiment the base is an organic base, such as a tertiary amine. Exemplary organic bases include diisopropylethylamine (DIPEA), spartene (either enantiomeric form), imidazole, 4,4-dimethylamino pyridine, triethylamine, dicyclohexylethylamine and DBU. The amount of base in the reaction mixture may vary. In an exemplary embodiment, the base is present in an amount from about 0.001 equivalents to about 5.0 equivalents, preferably from about 0.01 equivalents to about 1 equivalent, more preferably from about 0.05 equivalents to 0.3 equivalents, and even more preferably about 0.1 equivalents relative to the aldehyde reactant.

Reaction Conditions

The reactions described herein can be carried out at any useful temperature. Choosing an appropriate reaction temperature is well within the abilities of those skilled in the art. In an exemplary embodiment, the method of the invention employs a reaction temperature from about −78° C. to about 100° C., preferably from about 0° C. to about 50° C. and more preferably from about 10° C. to about 30° C.

In another exemplary embodiment, the methods described herein employ a reaction time between about 0.1 hours to about 72 hours, preferably between about 1 hour and about 48 hours, more preferably between about 10 hours and about 30 hours. In a preferred embodiment, the reaction is carried out at ambient temperature for about 15 to about 24 hours.

The reactions can be carried out at any useful pressure. Choosing an appropriate reaction pressure is well within the abilities of those skilled in the art. In an exemplary embodiment, the method of the invention employs a reaction pressure of from about 0.1 atm to about 2 atm. In an exemplary embodiment, the method of the invention employs a reaction pressure of from about 0.1 atm to about 1 atm. In an exemplary embodiment, the method of the invention employs a reaction pressure of from about 0.5 atm to about 1.3 atm. In an exemplary embodiment, the method of the invention employs a reaction pressure of from about 0.8 atm to about 1.3 atm. In an exemplary embodiment, the method of the invention employs a reaction pressure of from about 1 atm. In an exemplary embodiment, the method of the invention employs a reaction pressure which is the ambient pressure of the surroundings.

The amount of the organic catalyst used in the reaction can vary. In an exemplary embodiment, the amount of organic catalyst used in a reaction described herein is from about 0.05 mol % to about 50 mol %, relative to the imine or the enone. In an exemplary embodiment, the amount of organic catalyst used in a reaction described herein is from about 8 mol % to about 20 mol %, relative to the imine or the enone. In an exemplary embodiment, the amount of organic catalyst used in a reaction described herein is from about 8 mol % to about 12 mol %, relative to the imine or the enone. In an exemplary embodiment, the amount of organic catalyst used in a reaction described herein is from about 10 mol %, relative to the imine or the enone. In an exemplary embodiment, the amount of organic catalyst used in a reaction described herein is from about 0.01 mol % to about 5 mol %, relative to the imine or the enone. In an exemplary embodiment, the amount of organic catalyst used in a reaction described herein is from about 0.01 mol % to about 2 mol %, relative to the imine or the enone. In an exemplary embodiment, the amount of organic catalyst used in a reaction described herein is from about 2 mol %, relative to the imine or the enone. In an exemplary embodiment, the amount of organic catalyst used in a reaction described herein is from about 0.001 mol % to about 1 mol %, relative to the imine or the enone. In an exemplary embodiment, the amount of organic catalyst used in a reaction described herein is from about 1 mol %, relative to the imine or the enone. In an exemplary embodiment, the amount of organic catalyst used in a reaction described herein is from about 0.001 mol % to about 0.05 mol %, relative to the imine or the enone. In an exemplary embodiment, the amount of organic catalyst used in a reaction described herein is from about 0.05 mol %, relative to the imine or the enone.

Reaction Products

The method of the invention can be used to prepare a variety of chiral heterocyclic compounds. In an exemplary embodiment those compounds have a formula selected from:

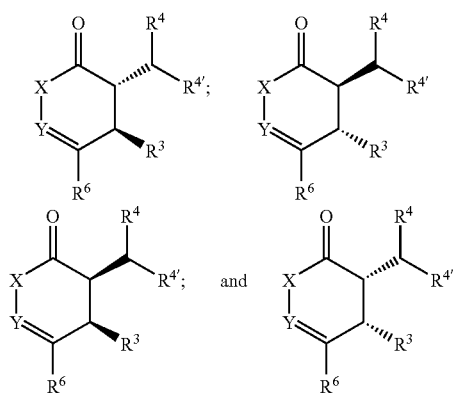

wherein X is a member selected from O and $NR^1$ and Y is a member selected from $CR^2$ and $NO^-$. $R^1$, $R^2$, $R^3$, $R^4$, $R^{4'}$ and $R^6$ are as defined herein.

In one exemplary embodiment, at least one of $R^4$ and $R^{4'}$ is a carboxylic acid ester. In an exemplary embodiment, Y is $CR^2$.

Exemplary chiral heterocyclic compounds that can be prepared by the methods described herein include:

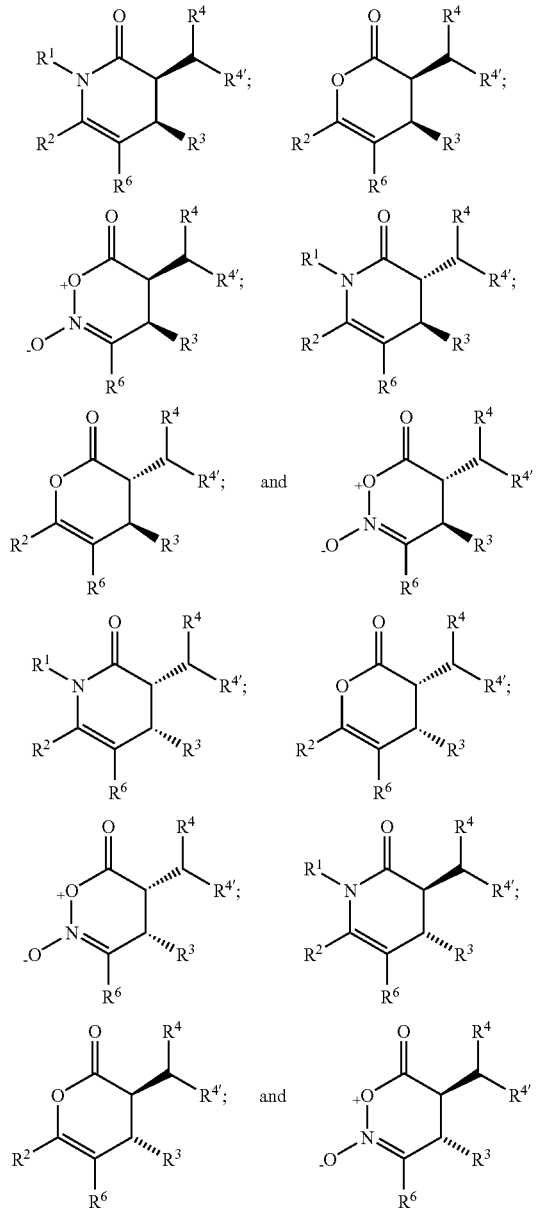

wherein $R^1$, $R^2$, $R^3$, $R^4$, $R^{4'}$ and $R^6$ are as defined above.

In one exemplary embodiment, in which the aldehyde reactant has the formula:

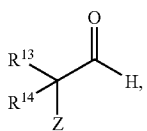

the resulting compound has the formula:

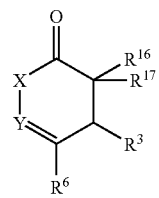

wherein $R^{16}$ and $R^{17}$ are members independently selected from H, substituted or unsubstituted alkyl and substituted or unsubstituted heteroalkyl.

Enantiomeric (Diastereomeric Excess)

In a preferred embodiment, the enantiomeric excess (ee) of a desired enantiomer or the diastereomeric excess of a desired diastereomer produced by the methods described herein is from about 60% ee (de) to about 99% ee (de), preferably from about 70% ee (de) to about 99% ee (de), more preferably from about 80% ee (de) to about 99% ee (de), still more preferably from about 90% ee (de) to about 99% ee (de), still more preferably from about 92% ee (de) to about 99% ee (de), still more preferably from about 94% ee (de) to about 99% ee (de), still more preferably from about 95% ee (de) to about 99% ee (de), still more preferably from about 96% ee (de) to about 99% ee (de), still more preferably from about 97% ee (de) to about 99% ee (de), still more preferably from about 98% ee (de) to about 99% ee (de).

In another preferred embodiment, the invention provides chiral reaction products having an enantiomeric (diastereomeric) excess of at least about 99%, preferably at least about 99.5%, and more preferably at least about 99.8%.

An exemplary method for the preparation of chiral heterocyclic compounds of the present invention is outlined in Scheme 1 below.

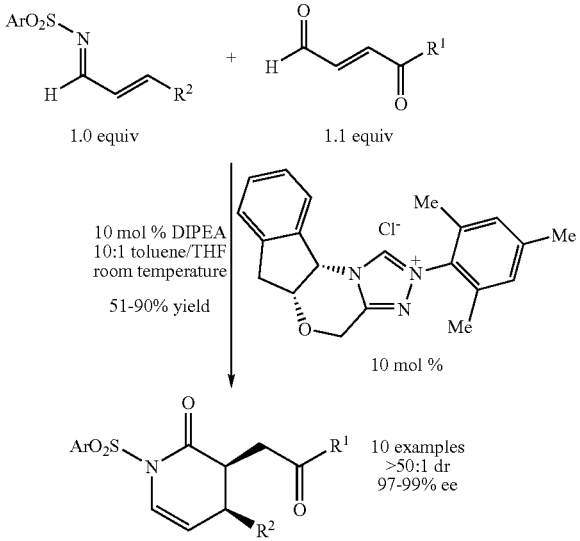

In Scheme 1 the imine is reacted with the aldehyde in the presence of 10 mol % of a chiral, organic catalyst as well as 10 mol % of diisopropylethylamine (DIPEA) as base at room temperature to form the corresponding dihydropyridinones in about 51 to about 90% yield and greater than about 95% ee.

In another exemplary embodiment, the imine is reacted with an aldehyde containing an alpha-heteroatom. An exemplary reaction is outlined in Scheme 2.

Scheme 2

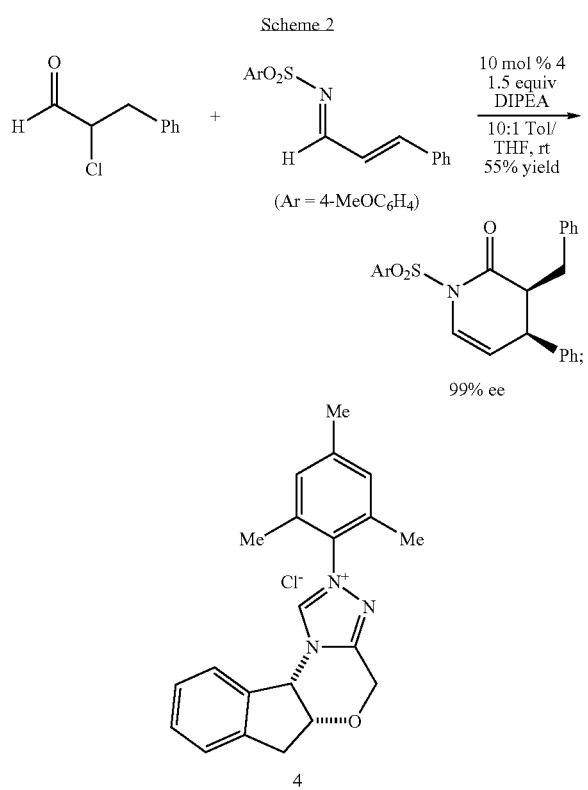

Compositions

In another aspect the invention provides a mixture containing an organic catalyst described herein and an aldehyde described herein, such as those described above. In another exemplary embodiment the organic catalyst has a structure according to Formula I. In an exemplary embodiment this mixture further contains a diene reactant described herein. In another exemplary embodiment the diene reactant is an imine described herein. In another exemplary embodiment the imine has a structure according to Formula II. In another exemplary embodiment the diene reactant is an enone described herein.

The following examples are provided to illustrate selected embodiments of the invention and are not to be construed as limiting its scope.

EXAMPLES

General Methods

All reactions utilizing air- or moisture-sensitive reagents were performed in dried glassware under an atmosphere of dry argon. Chlorobenzene and $CH_2Cl_2$ were distilled over $CaH_2$. Toluene and THF were dried by passage over activated alumina under Ar atmosphere. All aldehydes were purified by distillation prior to use. Diisopropylethylamine (DIPEA) was distilled from KOH. Other reagents were used without further purification. Thin layer chromatography (TLC) was performed on Merck precoated plates (silica gel 60 $F_{254}$, Art 5715, 0.25 mm) and were visualized by fluorescence quenching under UV light or by staining with phosphomolybdic acid. Silica-gel preparative thin-layer chromatography (PTLC) was performed using plates prepared from Merck Kieselgel 60 $PF_{254}$ (Art 7747). Column chromatography was performed on E. Merck Silica Gel 60 (230-400 Mesh) using a forced flow of 0.5-1.0 bar. $^1H$ NMR (400 MHz) and $^{13}C$ NMR (100 MHz) were measured on a Varian Unity 400 spectrometer. Chemical shifts are expressed in parts per million (PPM) downfield from residual solvent peaks and coupling constants are reported as Hertz (Hz). Splitting patterns are indicated as follows: br, broad; s, singlet; d, doublet; t, triplet; q, quartet; m, multiplet. Infrared (IR) spectra were recorded on a JASCO FT/IR-430 spectrophotometer and are reported as wavenumber ($cm^{-1}$). Optical rotations were measured on a Jasco DIP-1000 polarimeter operating at the sodium D line with a 100 mm path length cell, and are reported as follows: $[\alpha]^T$ (concentration (g/100 ml), solvent). HPLC Conditions: Column, Diacel Chiralpak AS-H, (4.6×250 mm) Eluent: hexanes/i-PrOH. Flow Rate 1.0 mL/min. Detection: 254 nm. Column, Diacel Chiralpak AD-H, (4.6×250 mm) Eluent: hexanes/iPrOH. Flow Rate 1.0 mL/min. Detection: 254 nm. Column, Diacel Chiralpak OD-H, (4.6×250 mm) Eluent: hexanes/iPrOH. Flow Rate 1.0 mL/min. Detection: 254 nm.

Example 1

General Procedure for NHC-Catalyzed, Enantioselective Azadiene Diels-Alder Reactions

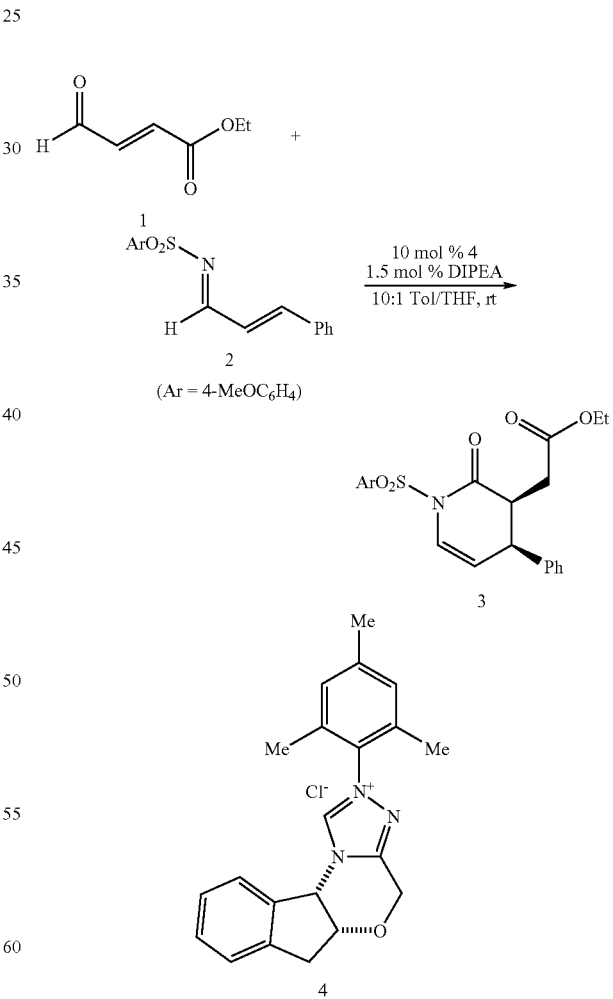

The reaction of enal 1 and imine 2 is representative. Into an oven dried 2.0 mL vial was added enal 1 (6.5 ml, 0.054 mmol, 1.1 equiv), imine 2 (14.7 mg, 0.049 mmol, 1.0 equiv) and catalyst 4 (1.8 mg, 0.005 mmol, 0.10 equiv). The vial was crimped with a Teflon-lined crimp seal. To this mixture was added 1.0 mL 10:1 toluene/THF (0.05 M), followed by diisopropylethylamine (0.8 ul, 0.005 mmol, 0.10 equiv). The resulting solution was stirred at room temperature for 23 h. The reaction mixture was concentrated under reduced pressure, and the residue was purified by preparative thin layer chromatography (2:1 hexanes/EtOAc) to afford the lactam product 3 as a white solid (19.8 mg, 90% yield).

TABLE 1

Development and optimization of NHC-catalyzed azadiene Diels-Alder reactions (Ar = MeOC$_6$H$_4$)

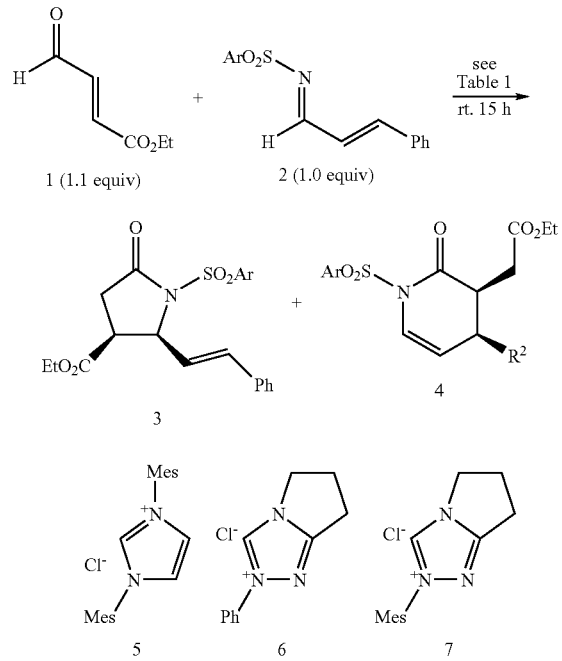

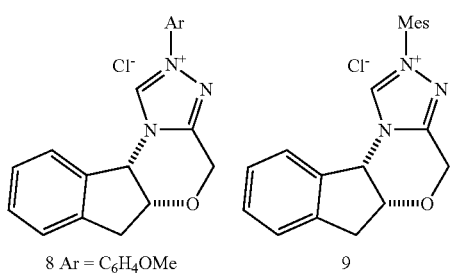

8 Ar = C$_6$H$_4$OMe     9

| entry | cat. (%) | conditions | 3:4[a] | % conv.[b] |
|---|---|---|---|---|
| 1 | 5 (15) | 10 mol % DBU, 0.1 M THF | >10:1 | 36 (7:1 dr) |
| 2 | 5 (15) | 10 mol % DIPEA, 0.1 M THF | >10:1 | 13 (2:1 dr) |
| 3 | 6 (15) | 10 mol % DBU, 0.1 M THF | — | — |
| 4 | 7 (15) | 10 mol % DBU, 0.1 M THF | 1:8 | 47 |
| 5 | 7 (15) | 10 mol % DBU, 0.1 M EtOAc | 1:5 | 38 |
| 6 | 7 (15) | 10 mol % DBU, 0.1 M toluene | 1:10 | 44 |
| 7 | 7 (15) | 10 mol % DIPEA, 0.1 M toluene | >1:20[c] | 44 |
| 8 | 7 (10) | 10 mol % DIPEA, 23 h 0.05 M 10:1 toluene:THF | >1:20[c] | 63 |
| 9 | 8 (10) | 10 mol % DIPEA, 23 h 0.05 M 10:1 toluene:THF | — | — |
| 10 | 9 (10) | 10 mol % DIPEA, 23 h 0.05 M 10:1 toluene:THF | >1:20[c] | 90% yield[d] 99.5% ee |

[a]Product ratios and diastereoselectivities determined by $^1$H NMR analysis of unpurified reaction mixtures.
[b]Ratio of lactam products relative to starting imine.
[c]Lactam 3 was not detected.
[d]Isolated yield after chromatography. DIPEA = N,N-diisopropylethylamine.

TABLE 2

Catalytic, enantioselective Diels-Alder reactions.[a]

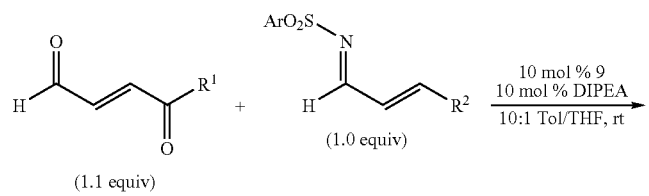

| entry | R$^1$ = | R$^2$ = | product | % yield[b] | % ee[d] |
|---|---|---|---|---|---|

TABLE 2-continued

| # | | | | Yield | er |
|---|---|---|---|---|---|
| 1 | OEt | Ph | 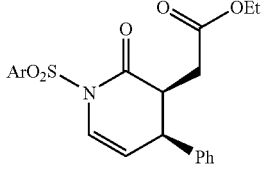 | 90 | 99 (S,S) |
| 2[c] | OEt | Ph | 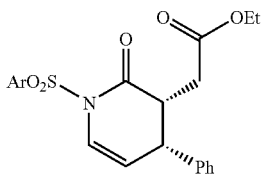 | 90 | 99 (R,R) |
| 3 | OEt | 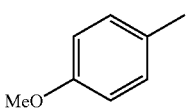 | 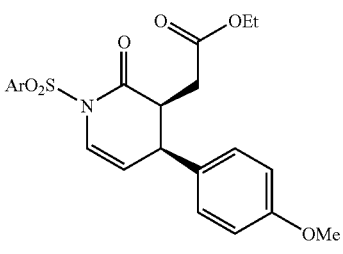 | 81 | 99 (S,S) |
| 4 | OEt | 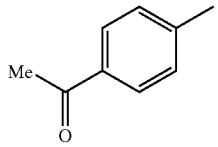 | 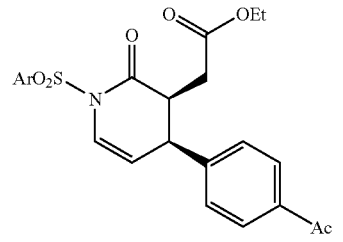 | 55 | 99 (S,S) |
| 5 | OEt | 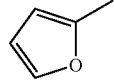 | 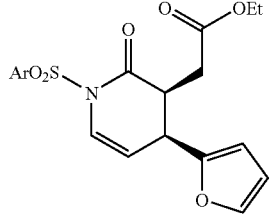 | 71 | 99 (S,S) |
| 6 | OEt | n-Pr | 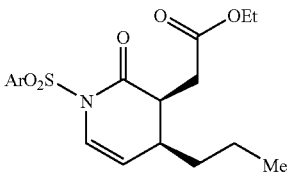 | 58 | 99 (S,S) |

[a] Ar = 4-MeOC$_6$H$_4$. All reactions were performed at 0.05 M for 23-48 h. In all cases only a single diastereomer was detected in unpurified reaction mixtures by $^1$H NMR or HPLC analysis

[b] Isolated yield after chromatography.

[c] 10 mol % ent-9 was used as the catalyst.

[d] Determined by HPLC analysis on Chiralpak AS (entries 1-3, 6), OD (entry 4) or AD (entry 5) columns. All enantiomeric ratios were >200:1 based on integration of the minor enantiomer or baseline.

TABLE 3

Variation of the enal substrate[a]

| entry | R[1] = | R[2] = | product | % yield[b] | % ee[d] |
|---|---|---|---|---|---|
| 1 | O$^t$Bu | Ph | *(structure)* | 70 | 97 (S,S) |
| 2[b] | Me | Ph | *(structure)* | 51 | 99 (S,S) |
| 3 | Me | n-Pr | *(structure)* | 71 | 98 (S,S) |
| 4 | Ph | *(4-methoxyphenyl)* | *(structure)* | (53) | 99 (S,S) |

[a] See Table 2 above for reaction conditions and notes.
[b] An additional 1.0 equiv portion of the enal was added after 15 h.
[c] Determined by HPLC analysis on Chiralpak AD (entry 2) and AS (entries 1, 3, 4) columns

Example 2

Synthesis of Ethyl 2-((3S,4S)-1-(4-methoxyphenylsulfonyl)-2-oxo-4-phenyl-1,2,3,4-tetrahydropyridin-3-yl)acetate (Table 2, entry 1)

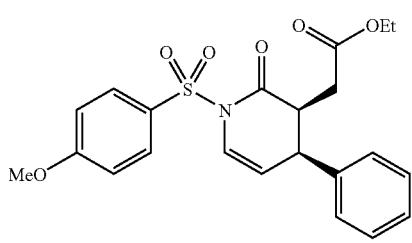

The title compound was prepared according to the general procedure from ethyl trans-4-oxo-2-butenoate and trans-N-(4-methoxybenzenesulfonyl)-3-phenyprop-2-ene-1-imine using 10 mol % 9 as the catalyst in 90% yield as a white solid. $[\alpha]_D^{20}$ (c 1.19, CHCl$_3$)=+105.2; mp=111-113° C.; $^1$H NMR (400 MHz, CDCl$_3$) δ 8.04 (dd, 2H, J=7.0, 2.1 Hz), 7.16-7.12 (m, 2H), 7.06-6.99 (m, 4H), 6.58 (dd, 2H, J=8.0, 1.1 Hz), 5.60 (dd, 1H, J=8.0, 6.5 Hz), 4.18-4.08 (m, 2H), 3.92 (s, 3H), 3.65 (t, 1H, J=6.9 Hz), 3.55-3.53 (m, 1H), 2.57 (dd, 1H, J=17.3, 6.1 Hz), 1.94 (dd, 1H, J=17.3, 7.5 Hz), 1.21 (t, 3H, J=7.0 Hz); $^{13}$C NMR (100 MHz, CDCl$_3$) δ 171.7, 169.0, 164.3, 136.8, 131.4, 129.2, 128.9, 127.7, 127.9, 124.6, 114.3, 113.6, 61.0, 56.0, 44.1, 42.0, 31.6, 14.3; IR (thin film) ν 3086, 2982, 1720, 1594, 1496, 1454, 1406, 1367, 1264, 1132, 1091, 1026 cm$^{-1}$; HRMS (ESI) calcd for C$_{22}$H$_{23}$NO$_6$S [M+Na]$^+$ 452.1138, found 452.1160; >99% ee (3R,4R)-isomer as determined by HPLC (AS-H, 9:1 hexanes/i-PrOH), t$_r$ (3S,4S)=53.9 min, t$_r$ (3R,4R)=39.2 min. For the (3R,4R) enantiomer (Table 2, entry 2), $[\alpha]_D^{20}$ (c 0.98, CHCl$_3$)=−112.7.

Example 3

Ethyl 2-((3S,4S)-4-(4-methoxyphenyl)-1-(4-methoxyphenylsulfonyl)-2-oxo-1,2,3,4-tetra-hydropyridin-3-yl)acetate (Table 2, entry 3)

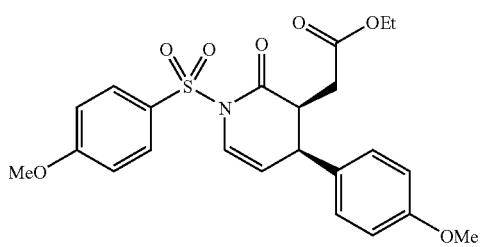

The title compound was prepared according to the general procedure from ethyl trans-4-oxo-2-butenoate and trans-N-(4-methoxybenzenesulfonyl)-3-(4-methoxyphenyl)prop-2-en-1-imine using 10 mol % 9 as the catalyst in 81% yield as a yellow solid. $[\alpha]_D^{20}$ (c 1.04, CHCl$_3$)=+143.6; mp=107-110° C.; $^1$H NMR (400 MHz, CDCl$_3$) δ 8.03 (dd, 2H, J=7.1, 1.8 Hz), 7.13 (d, 1H, J=8.1 Hz), 7.05 (dd, 2H, J=7.1, 1.8 Hz), 6.55-6.48 (m, 4H), 5.59 (dd, 1H, J=8.0, 6.6 Hz), 4.16-4.09 (m, 2H), 3.92 (s, 3H), 3.71 (s, 3H), 3.60 (t, 1H, J=6.9 Hz), 3.52-3.47 (m, 1H), 2.58 (dd, 1H, J=17.2, 6.0 Hz), 1.95 (dd, 1H, J=17.2, 7.7 Hz), 1.22 (t, 3H, J=7.0 Hz); $^{13}$C NMR (100 MHz, CDCl$_3$) δ 171.8, 169.1, 164.3, 159.2, 131.4, 129.2, 128.5, 124.3, 114.3, 114.3, 113.9, 113.6, 61.0, 56.0, 55.3, 44.3, 41.2, 31.5, 14.4; IR (thin film) ν 3055, 2840, 1720, 1647, 1511, 1498, 1463, 1442, 1366, 1263, 1167, 1090, 1028 cm$^{-1}$; HRMS (ESI) calcd for C$_{23}$H$_{25}$NO$_7$S [M+Na]$^+$ 482.1243, found 482.1253; >99% ee (3S,4S)-isomer as determined by HPLC (AS-H, 4:1 hexanes/i-PrOH), t$_r$ (3S,4S)=49.3 min, t$_r$ (3R,4R)=29.6 min.

Example 4

Ethyl 2-((3S,4S)-4-(4-acetylphenyl)-1-(4-methoxyphenylsulfonyl)-2-oxo-1,2,3,4-tetrahydro-pyridin-3-yl)acetate (Table 2, entry 4)

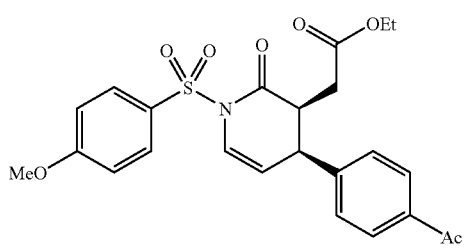 [SMILES: CCOC(=O)C[C@@H]1C(=O)N(S(=O)(=O)c2ccc(OC)cc2)C=C[C@@H]1c1ccc(C(C)=O)cc1]

Prepared according to the general procedure from ethyl trans-4-oxo-2-butenoate and trans-N-(4-methoxybenzenesulfonyl)-1-(4-(3-iminoprop-1-enyl)phenyl)ethanone using 10 mol % 9 as the catalyst in 55% yield as a yellow oil. $[\alpha]_D^{20}$ (c 1.22, CHCl$_3$)=+168.2; $^1$H NMR (400 MHz, CDCl$_3$) δ 8.04 (dd, 2H, J=6.9, 2.1 Hz), 7.59 (dd, 2H, J=6.5, 1.9 Hz), 7.19 (d, 1H, J=8.0 Hz), 7.07 (dd, 2H, J=6.9, 2.1 Hz), 6.69 (dd, 2H, J=6.6, 1.7 Hz), 5.59 (dd, 1H, J=8.0, 6.6 Hz), 4.14-4.11 (m, 2H), 3.95 (s, 3H), 3.74 (t, 1H, J=6.9 Hz), 3.58-3.53 (m, 1H), 2.58 (dd, 1H, J=17.4, 6.0 Hz), 2.52 (s, 3H), 1.90 (dd, 1H, J=17.4, 7.8 Hz), 1.22 (t, 3H, J=7.2 Hz); $^{13}$C NMR (100 MHz, CDCl$_3$) δ 197.5, 171.5, 168.6, 164.5, 142.3, 136.6, 131.4, 128.9, 128.2, 125.3, 114.3, 112.7, 94.6, 61.1, 56.1, 43.9, 41.7, 31.4, 26.7, 14.3; IR (thin film) ν 3020, 2983, 2842, 1723, 1682, 1594, 1497, 1363, 1267, 1167, 1091, 1024 cm$^{-1}$; HRMS (ESI) calcd for C$_{24}$H$_{25}$NO$_7$S [M+Na]$^+$ 494.1243, found 494.1265; >99% ee (3S,4S)-isomer as determined by HPLC(OD-H, 4:1 hexanes/i-PrOH), t$_r$ (3S,4S)=28.6 min, t$_r$ (3R,4R)=35.1 min.

Example 5

Ethyl 2-((3S,4S)-4-(furan-2-yl)-1-(4-methoxyphenylsulfonyl)-2-oxo-1,2,3,4-tetrahydro-pyridin-3-yl)acetate (Table 2, entry 5)

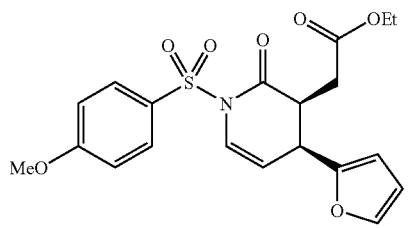 [SMILES: CCOC(=O)C[C@@H]1C(=O)N(S(=O)(=O)c2ccc(OC)cc2)C=C[C@@H]1c1ccco1]

The title compound was prepared according to the general procedure from ethyl trans-4-oxo-2-butenoate and trans-N-(4-methoxybenzenesulfonyl)-3-(furan-2-yl)prop-2-en-1-imine using 10 mol % 9 as the catalyst in 71% yield as a yellow solid. $[\alpha]_D^{20}$ (c 1.58, CHCl$_3$)=+125.7; mp=98-100° C.; $^1$H NMR (400 MHz, CDCl$_3$) δ 7.98 (dd, 2H, J=7.0, 1.9 Hz), 7.12 (d, 2H, J=8.0 Hz), 7.00 (dd, 21-1, J=7.0, 1.9 Hz), 6.87 (d, 1H, J=1.8 Hz), 6.11 (dd, 1H, J=3.2, 1.8 Hz), 5.82 (d, 1H, J=3.2 Hz), 5.51 (dd, 1H, J=8.0, 6.8 Hz), 4.15-4.10 (m, 2H), 3.90 (s, 3H), 3.75 (t, 1H, J=6.7 Hz), 3.45-3.40 (m, 1H), 2.72 (dd, 1H, J=17.3, 6.0 Hz), 2.52 (s, 3H), 2.04 (dd, 1H, J=17.3, 7.7 Hz), 1.22 (t, 3H, J=7.0 Hz); $^{13}$C NMR (100 MHz, CDCl$_3$) δ 171.7, 168.7, 164.2, 142.6, 131.4, 129.6, 125.7, 114.1, 110.4, 108.0, 61.0, 56.0, 43.2, 35.1, 31.5, 14.3; IR (thin film) ν 3114, 2982, 2843, 1724, 1595, 1498, 1363, 1263, 1167, 1133, 1092, 1025 cm$^{-1}$; HRMS (ESI) calcd for C$_{20}$H$_{21}$NO$_7$S [M+Na]$^+$ 494.1243, found 494.1265; >99% ee (3S,4S)-isomer as determined by HPLC (AD-H, 9:1 hexanes/i-PrOH), t$_r$ (3S,4S)=43.7 min, t$_r$ (3R,4R)=37.4 min.

Example 6

Ethyl 2-3S,4S)-1-(4-methoxyphenylsulfonyl)-2-oxo-4-propyl-1,2,3,4-tetrahydropyridin-3-yl)acetate (Table 1, entry 6)

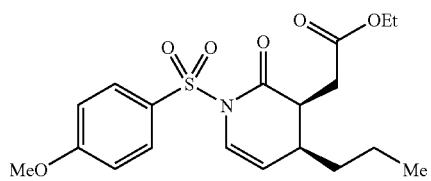 [SMILES: CCC[C@H]1C=CN(S(=O)(=O)c2ccc(OC)cc2)C(=O)[C@H]1CC(=O)OCC]

The title compound was prepared according to the general procedure from ethyl trans-4-oxo-2-butenoate and trans-N-(4-methoxybenzenesulfonyl)-hex-2-en-1-imine using 10 mol % 9 as the catalyst in 58% yield as a colorless oil. $[\alpha]_D^{20}$ (c 0.64, CHCl$_3$)=−17.3; $^1$H NMR (400 MHz, CDCl$_3$) δ 7.92 (dd, 2H, J=6.9, 2.0 Hz), 6.97 (dd, 2H, J=6.9, 2.0 Hz), 5.53 (dd, 1H, J=8.0, 6.6 Hz), 4.13-4.11 (m, 2H), 3.87 (s, 3H), 3.24 (q, 1H, J=6.3 Hz), 2.82 (dd, 1H, J=16.6, 7.2 Hz), 2.41-2.38 (m, 1H), 2.24 (dd, 1H, J=16.6, 7.0 Hz), 1.22 (t, 3H, J=7.2 Hz), 1.25-1.02 (m, 4H), 0.73 (t, 3H, J=7.2 Hz); $^{13}$C NMR (100 MHz, CDCl$_3$) δ 171.7, 170.2, 164.2, 131.1, 129.5, 124.2, 114.9, 114.1, 61.0, 55.9, 43.4, 34.5, 31.6, 31.4, 19.3, 14.3, 14.2; IR (thin film) ν 3046, 1723, 1595, 1506, 1418, 1358, 1271, 1133 cm$^{-1}$; HRMS (ESI) calcd for C$_{19}$H$_{25}$NO$_6$S [M+Na]$^+$ 418.1294, found 418.1287; >99% ee (3S,4S)-isomer as determined by HPLC (AS-H, 9:1 hexanes/i-PrOH), t$_r$ (3S,4S)=55.0 min, t$_r$ (3R,4R)=28.2 min.

Example 7 tert-Butyl 2-((3S,4S)-1-(4-methoxyphenylsulfonyl)-2-oxo-4-phenyl-1,2,3,4-tetrahydro-pyridin-3-yl)acetate (Table 3, entry 1)

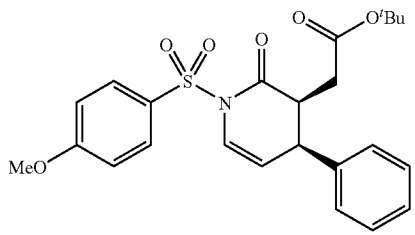 [SMILES: COc1ccc(S(=O)(=O)N2C=C[C@H](c3ccccc3)[C@H](CC(=O)OC(C)(C)C)C2=O)cc1]

The title compound was prepared according to the general procedure from tert-butyl trans-4-oxo-2-butenoate and trans-N-(4-methoxybenzenesulfonyl)-3-phenylprop-2-en-1-imine using 10 mol % 9 as the catalyst in 70% yield white solid. $[\alpha]_D^{20}$ (c 1.07, CHCl$_3$)=+90.4; mp=139-142° C.; $^1$H NMR (400 MHz, CDCl$_3$) 8.03 (dd, 21-1, J=6.9, 2.1 Hz), 7.16-7.13 (m, 2H), 7.05-7.00 (m, 4H), 6.60 (dd, 2H, J=8.2, 1.0 Hz), 5.59 (dd, 1H, J=8.1, 6.6 Hz), 3.92 (s, 3H), 3.66 (t, 1H, J=6.9 Hz), 3.49-3.43 (m, 1H), 2.57 (dd, 1H, J=17.3, 6.1 Hz), 1.94 (dd, 1H, J=17.3, 7.5 Hz), 1.41 (s, 9H); $^{13}$C NMR (100 MHz, CDCl$_3$) δ 171.0, 169.0, 164.3, 136.9, 131.4, 129.2, 128.9, 128.0, 127.8, 124.5, 114.2, 113.6, 81.1, 56.0, 44.2, 41.9, 32.5, 28.2; IR (thin film) ν 3086, 2976, 1715, 1594, 1496, 1364, 1264, 1167, 1080 cm$^{-1}$; HRMS (ESI) calcd for C$_{24}$H$_{27}$NO$_6$S [M+Na]$^+$ 480.1451, found 480.1456; 97% ee (3S,4S)-isomer as determined by HPLC (AS-H, 9:1 hexanes/i-PrOH), t$_r$ (3S, 4S)=19.4 min, t$_r$ (3R,4R)=14.1 min.

Example 8

(3S,4S)-1-(4-Methoxyphenylsulfonyl)-3-(2-oxopropyl)-4-phenyl-3,4-dihydropyridin-2(1H)-one (Table 3, entry 2)

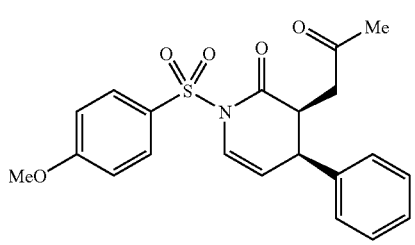 [SMILES: COc1ccc(S(=O)(=O)N2C=C[C@H](c3ccccc3)[C@H](CC(C)=O)C2=O)cc1]

Into an oven dried 2.0 mL vial was added (E)-4-oxopent-2-enal (10.0 mg 0.10 mmol, 1.0 equiv), trans-N-(4-methoxybenzenesulfonyl)-3-phenylprop-2-en-1-imine (30.1 mg, 0.10 mmol, 1.0 equiv) and chiral catalyst 9 (5.5 mg, 0.01 mmol, 0.10 equiv). The vial was crimped with a Teflon-lined crimp seal. To this mixture was added 2.0 mL 10:1 toluene/THF (0.05 M), followed by diisopropylethylamine (1.7 µL, 0.01 mmol, 0.10 equiv). The resulting solution was stirred at room temperature for 15 h before an additional 1.0 equiv of enal was added and the resulting solution was stirred for an additional 23 h. The reaction mixture was concentrated under reduced pressure, and the residue was purified by PTLC (2:1 hexane/EtOAc) to afford the lactam product as a white solid (20.4 mg, 51% yield). $[\alpha]_D^{20}$ (c 1.10, CHCl$_3$)=+186.4; mp=150-152° C.; $^1$H NMR (400 MHz, CDCl$_3$) δ 7.97 (dd, 2H, J=6.9, 2.0 Hz), 7.14 (d, 2H, J=8.2 Hz), 7.06-6.98 (m, 5H), 6.56 (dd, 2H, J=7.2, 1.1 Hz), 5.60 (dd, 1H, J=8.0, 6.2 Hz), 3.93 (s, 3H), 3.62-3.60 (m, 2H), 2.75 (dd, 1H, J=18.6, 5.2 Hz), 2.05 (s, 3H), 2.04 (dd, 1H, J=18.6, 6.9 Hz); $^{13}$C NMR (100 MHz, CDCl$_3$) δ 206.3, 169.5, 164.3, 137.4, 131.4, 129.0, 127.8, 124.4, 114.3, 113.7, 56.0, 43.0, 41.8, 40.1, 30.5; IR (thin film) ν 3111, 3028, 2842, 1713, 1594, 1496, 1362, 1264, 1167, 1091, 1024 cm$^{-1}$; HRMS (ESI) calcd for C$_{21}$H$_{21}$NO$_5$S [M+Na]$^+$ 422.1032, found 422.1034; >99% ee (3S,4S)-isomer as determined by HPLC (AD-H, 9:1 hexanes/i-PrOH), t$_r$ (3S,4S)=44.3 min, t$_r$ (3R,4R)=36.2 min.

Example 9

(3S,4S)-1-(4-Methoxyphenylsulfonyl)-3-(2-oxopropyl)-4-propyl-3,4-dihydropyridin-2(1H)-one (Table 3, entry 3)

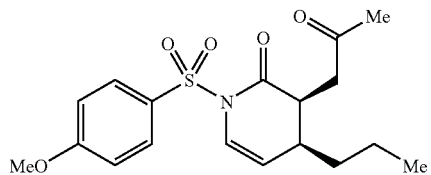 [SMILES: CCC[C@H]1C=CN(S(=O)(=O)c2ccc(OC)cc2)C(=O)[C@H]1CC(C)=O]

The title compound was prepared according to the general procedure from (E)-4-oxopent-2-enal and trans-N-(4-methoxybenzenesulfonyl)-hex-2-en-1-imine using 10 mol % 9 as the catalyst in 70% yield as a yellow oil. $[\alpha]_D^{20}$ (c 0.91, CHCl$_3$)=−5.7; $^1$H NMR (400 MHz, CDCl$_3$) δ 7.91 (dd, 2H, J=6.9, 2.0 Hz), 6.97 (dd, 2H, J=6.9, 2.0 Hz), 5.54 (dd, 1H, J=8.0, 6.6 Hz), 3.87 (s, 3H), 3.24 (q, 1H, J=6.3 Hz), 2.82 (dd, 1H, J=16.6, 7.2 Hz), 2.41-2.38 (m, 1H), 2.24 (dd, 1H, J=16.6, 7.0 Hz), 1.22 (t, 3H, J=7.2 Hz), 1.25-1.02 (m, 4H), 0.73 (t, 3H, J=7.2 Hz); $^{13}$C NMR (100 MHz, CDCl$_3$) δ 206.0, 170.7, 164.1, 131.0, 129.6, 128.8, 124.1, 115.1, 114.4, 114.1, 55.9, 42.4, 39.8, 34.7, 32.1, 30.6, 19.5, 14.3; IR (thin film) ν 3010, 2957, 1713, 1595, 1497, 1362, 1262, 1092, 1023 cm$^{-1}$; HRMS (ESI) calcd for C$_{18}$H$_{23}$NO$_5$S [M+Na]$^+$ 388.1189, found 388.1175; 98% ee (3S,4S)-isomer as determined by HPLC (AS-H, 9:1 hexanes/i-PrOH), t$_r$ (3S,4S)=68.1 min, t$_r$ (3R,4R)=55.1 min.

Example 10

(3S,4S)-4-(4-Methoxyphenyl)-1-(4-methoxyphenylsulfonyl)-3-(2-oxophenethyl)-3,4-dihydropyridin-2(1H)-one (Table 3, entry 4)

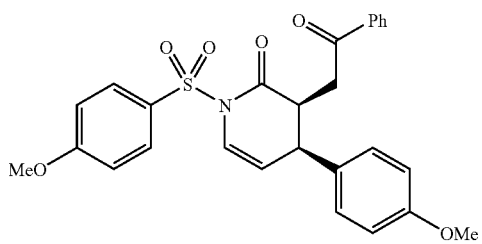 [SMILES: COc1ccc([C@H]2C=CN(S(=O)(=O)c3ccc(OC)cc3)C(=O)[C@H]2CC(=O)c2ccccc2)cc1]

The title compound was prepared according to the general procedure from (E)-4-oxo-4-phenylbut-2-enal and trans-N-(4-methoxybenzenesulfonyl)-3-(4-methoxyphenyl)prop-2-en-1-imine using 10 mol % 9 as the catalyst in 53% yield as a yellow solid. $[\alpha]_D^{20}$ (c 0.87, CHCl$_3$)=+232.3; mp=159-161° C.; $^1$H NMR (400 MHz, CDCl$_3$) δ 8.06 (dd, 2H, J=7.0, 2.0 Hz), 7.81 (dd, 1H, J=7.2, 1.4 Hz), 7.55-7.51 (m, 1H), 7.41-7.38 (m, 1H), 7.17 (d, 1H, J=8.1 Hz), 7.06 (dd, 2H, J=7.0, 2.0 Hz), 6.51-6.45 (m, 4H), 5.64 (dd, 1H, J=8.1, 6.3 Hz), 3.92 (s, 3H), 3.90-3.74 (m, 2H), 3.70 (s, 3H), 3.37 (dd, 1H, J=18.4, 3.5 Hz), 2.61 (dd, 1H, J=18.4, 8.0 Hz); $^{13}$C NMR (100 MHz, CDCl$_3$) δ 197.8, 169.8, 164.3, 159.1, 136.7, 133.5, 131.4, 129.3, 129.1, 128.9, 128.8, 128.2, 124.2, 114.3, 114.3, 114.2, 56.0, 55.3, 43.5, 40.7, 35.1; IR (thin film) ν 3025, 2987, 1716, 1684, 1495, 1510, 1361, 1264, 1166, 1091, 1028 cm$^{-1}$; HRMS (ESI) calcd for C$_{27}$H$_{25}$NO$_6$S [M+Na]$^+$ 514.1294, found 514.1307; >99% ee (3S,4S)-isomer as determined by HPLC (AS-H, 4:1 hexanes/i-PrOH), t$_r$ (3S,4S)=64.7 min, t$_r$ (3R,4R)=52.2 min.

Example 11

Ethyl 2-(3S,4S)-4-(4-bromophenyl)-1-(4-methoxyphenylsulfonyl)-2-oxo-1,2,3,4-tetrahydro-pyridin-3-yl)acetate

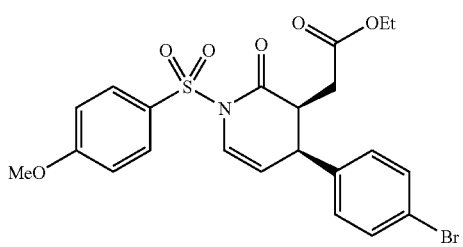

The title compound was prepared according to the general procedure from ethyl trans-4-oxo-2-butenoate and trans-N-(4-methoxybenzenesulfonyl)-3-(4-bromophenyl)prop-2-en-1-imine in 35% yield as a yellow solid. $[\alpha]_D^{20}$ (c 1.42, CHCl$_3$)=+151.4; mp=109-111° C.; $^1$H NMR (400 MHz, CDCl$_3$) δ 8.02 (dd, 2H, J=7.1, 2.1 Hz), 7.17-7.12 (m, 2H), 7.05 (dd, 2H, J=7.1, 2.2 Hz), 6.46 (dd, 2H, J=6.5, 2.1 Hz), 5.57 (dd, 1H, J=8.0, 6.6 Hz), 4.14-4.10 (m, 2H), 3.94 (s, 3H), 3.66-3.60 (m, 1H), 3.53-3.51 (m, 1H), 2.59 (dd, 1H, J=17.4, 6.0 Hz), 1.91 (dd, 1H, J=17.4, 7.9 Hz), 1.22 (t, 3H, J=7.4 Hz); $^{13}$C NMR (100 MHz, CDCl$_3$) δ 171.6, 168.7, 164.4, 135.8, 132.1 131.4, 129.6, 128.8, 125.0, 121.8, 114.4, 114.4, 113.0, 61.1, 56.1, 43.9, 41.3, 31.4, 14.3; IR (thin film) ν 3087, 2978, 1719, 1594, 1496, 1365, 1263, 1190, 1166, 1091, 1025 cm$^{-1}$; HRMS (ESI) calcd for C$_{22}$H$_{22}$BrNO$_6$S [M+Na]$^+$ 530.0248, found 530.0254; >99% ee (3S,4S)-isomer as determined by HPLC (AS-H, 9:1 hexanes/i-PrOH), t$_r$ (3S,4S)=65.6 min, t$_r$ (3R,4R)=44.6 min.

Example 12 cis-3-Benzyl-1-(4-methoxyphenylsulfonyl)-4-phenyl-3,4-dihydropyridin-2(1H)-one (14)

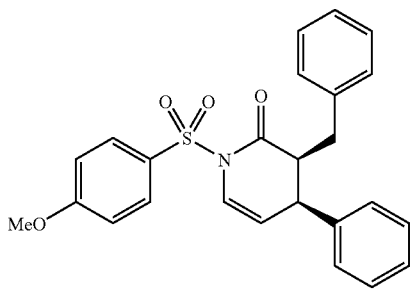 [SMILES: COc1ccc(S(=O)(=O)N2C=C[C@H](c3ccccc3)[C@H](Cc3ccccc3)C2=O)cc1]

The title compound was prepared according to the general procedure from 2-chloro-3-phenylpropanal and trans-N-(4-methoxybenzenesulfonyl)-3-phenyprop-2-ene-1-imine using 10 mol % 7 and 1.5 equiv DIPEA in 40% yield. $^1$H NMR (400 MHz, CDCl$_3$) δ 8.02 (dd, 2H, J=7.0, 2.1 Hz), 7.24-7.10 (m, 4H), 7.09-6.94 (m, 7H), 6.47 (dd, 2H, J=8.0, 1.0 Hz), 5.48 (dd, 1H, J=8.0, 6.3 Hz), 3.90 (s, 3H), 3.33-3.30 (m, 1H), 3.27-3.21 (m, 1H), 3.15 (dd, 1H, J=14.6, 4.3 Hz), 2.10 (dd, 1H, J=14.6, 9.0 Hz); $^{13}$C NMR (100 MHz, CDCl$_3$) δ 170.2, 164.3, 138.8, 137.4, 131.5, 129.2, 129.1, 128.8, 128.7, 128.2, 127.7, 126.6, 124.1, 114.4, 114.3, 56.0, 48.9, 41.1, 31.5; IR (thin film) ν 3062, 3029, 2926, 1721, 1594, 1496, 1362, 1263, 1167, 1091, 1027 cm$^{-1}$; HRMS (ESI) calcd for C$_{25}$H$_{23}$NO$_4$S [M+Na]$^+$ XX, found XX.

Example 13

Preparation of Enals

All enals were prepared according to the literature procedures (Klei, A.; Jong, R. L. P.; Lugtenburg, J.; Tielens, A. G. M. *Eur. J. Org. Chem.* 2002, 3015-3023; Satoh, T.; Hanaki, N.; Kuramochi, Y.; Inoue, Y.; Hosoya, K.; Sakai, K. *Tetrahedron,* 2002, 58, 2533-2549).

13.1. (E)-tert-Butyl 4-oxobut-2-enoate

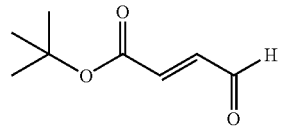

$^1$H NMR (400 MHz, CDCl$_3$) δ 9.58 (d, 1H, J=7.4 Hz), 6.71 (dd, 1H, J=15.9, 7.4 Hz), 6.51 (d, 1H, J=15.9 Hz), 1.36 (s,

12H); $^{13}$C NMR (100 MHz, CDCl$_3$) δ 192.8, 141.7, 139.6, 82.4, 27.9.

13.2. (E)-4-Oxopent-2-enal

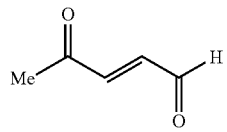

$^1$H NMR (400 MHz, CDCl$_3$) δ 9.77 (d, 1H, J=7.1 Hz), 6.83 (d, 1H, J=16.3 Hz), 6.72 (dd, 1H, J=16.3, 7.0 Hz), 2.40 (s, 311); $^{13}$C NMR (100 MHz, CDCl$_3$) δ 198.1, 193.7, 145.5, 138.3, 28.1.

13.3. (E)-4-Oxo-4-phenylbut-2-enal

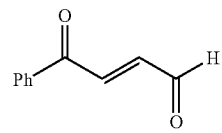 [SMILES: O=C/C=C/C(=O)c1ccccc1]

$^1$H NMR (400 MHz, CDCl$_3$) δ 9.89 (d, 1H, J=7.5 Hz), 8.00-7.99 (m, 2H), 7.74-7.64 (m, 2H), 7.56-7.52 (m, 2H), 6.99 (dd, 1H, J=15.8, 7.5 Hz); $^{13}$C NMR (100 MHz, CDCl$_3$) δ 193.0, 190.0, 142.3, 139.4, 136.4, 134.4, 129.2, 129.2.

Example 14

General Procedure for the Preparation of Imines

All imines were prepared according to literature protocols (He, M; Bode, J. W. *Org. Lett.* 2005, 7, 3131-3134). The corresponding dimethyl acetal (1.0 equiv) and the arylsulfonamide (1.0 equiv) were mixed in a flask equipped with a Dean-Stark condenser. The neat mixture was heated to 180° C. for 30 min. The resulting melt was cooled to room temperature and the solid was crystallized from toluene to yield the product.

14.1. trans-N-(4-Methoxybenzenesulfonyl)-3-phenylprop-2-en-1-imine

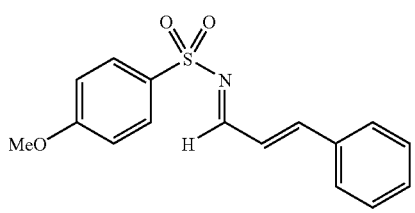 [SMILES: COc1ccc(S(=O)(=O)/N=C/C=C/c2ccccc2)cc1]

$^1$H NMR (400 MHz, CDCl$_3$) δ 8.74 (d, 1H, J=9.5 Hz), 7.89 (d, 2H, J=8.9 Hz), 7.54-7.40 (m, 6H), 7.00-6.93 (m, 3H), 3.85 (s, 3H); $^{13}$C NMR (100 MHz, CDCl$_3$) δ 170.5, 163.7, 153.8, 134.2, 131.7, 130.2, 129.7, 129.3, 128.7, 124.7, 114.5, 55.8.

14.2. trans-N-(4-Methoxybenzenesulfonyl)-3-(4-methoxyphenyl)prop-2-en-1-imine

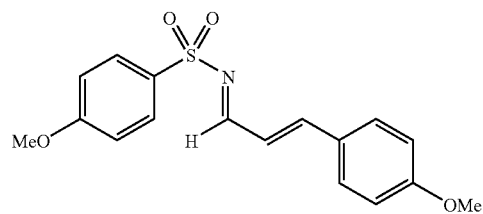 [SMILES: COc1ccc(/C=C/C=N/S(=O)(=O)c2ccc(OC)cc2)cc1]

Yellow solid; mp=116-118° C.; $^1$H NMR (400 MHz, CDCl$_3$) δ 8.67 (d, 1H, J=9.5 Hz), 7.84 (dd, 2H, J=6.9, 1.8 Hz), 7.46 (d, 2H, J=8.8 Hz), 7.37 (d, 1H, J=15.6 Hz), 6.95 (dd, 2H, J=6.9, 1.8 Hz), 6.88 (d, 2H, J=8.8 Hz), 6.81 (dd, 1H, J=15.6, 9.5 Hz), 3.82 (s, 3H), 3.81 (s, 3H); $^{13}$C NMR (100 MHz, CDCl$_3$) δ 170.9, 163.7, 162.7, 153.9, 130.8, 130.2, 127.2, 122.5, 114.9, 114.6, 55.9, 55.7; IR (thin film) ν 3007, 2938, 2840, 1596, 1573, 1319, 1259, 1166, 1151, 1090, 1025 cm$^{-1}$; HRMS (ESI) calcd for C$_{17}$H$_{17}$NO$_4$S [M+Na]$^+$ 354.0770, found 354.0766.

14.3. trans-N-(4-Methoxybenzenesulfonyl)-1-(4-(3-iminoprop-1-enyl)phenyl)ethanone

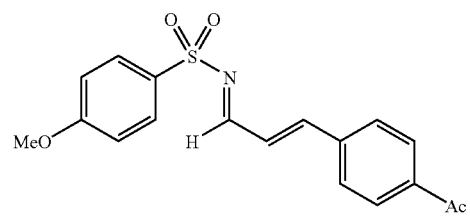 [SMILES: COc1ccc(S(=O)(=O)/N=C/C=C/c2ccc(C(C)=O)cc2)cc1]

Yellow solid; mp=173-176° C.; $^1$H NMR (400 MHz, CDCl$_3$) δ 8.72 (d, 1H, J=9.3 Hz), 7.94 (d, 2H, J=8.3 Hz), 7.85 (dd, 2H, J=7.0, 2.0 Hz), 7.58 (d, 2H, J=8.3 Hz), 7.45 (d, 1H, J=15.8 Hz), 7.00 (dd, 1H, J=15.8, 9.3 Hz), 6.96 (dd, 2H, J=7.0, 2.0 Hz), 3.83 (s, 3H), 2.57 (s, 3H); $^{13}$C NMR (100 MHz, CDCl$_3$) δ 197.4, 170.0, 164.0, 151.5, 138.9, 138.4, 130.5, 129.5, 129.2, 128.8, 127.2, 114.7, 114.4, 55.9, 27.0; IR (thin film) ν 3009, 2840, 1682, 1623, 1579, 1498, 1266, 1151, 1091, 1023 cm$^{-1}$; HRMS (ESI) calcd for C$_{18}$H$_{17}$NO$_4$S [M+Na]$^+$ 366.0770, found 366.0780.

14.4. trans-N-(4-Methoxybenzenesulfonyl)-3-(furan-2-yl)prop-2-en-1-imine

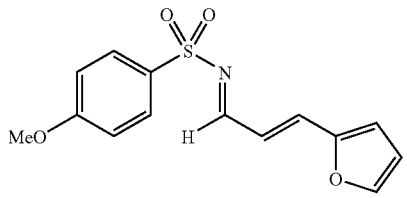 [SMILES: COc1ccc(S(=O)(=O)/N=C/C=C/c2ccco2)cc1]

Brown solid; mp=100-103° C.; $^1$H NMR (400 MHz, CDCl$_3$) δ 8.67 (d, 1H, J=9.7 Hz), 7.89 (dd, 2H, J=6.9, 2.0 Hz), 7.57 (d, 1H, J=1.9 Hz), 7.21 (d, 1H, J=15.5 Hz), 7.00 (dd, 2H, J=6.9, 2.0 Hz), 6.83 (dd, 1H, J=15.5, 9.7 Hz), 6.77 (d, 1H, J=3.5 Hz), 6.54 (dd, 1H, J=3.5, 1.9 Hz), 3.87 (s, 3H); $^{13}$C NMR (100 MHz, CDCl$_3$) 170.0, 163.7, 151.1, 146.7, 138.6, 130.3, 128.8, 122.5, 117.7, 114.6, 114.4, 113.3, 55.9, 55.8; IR (thin film) ν 3127, 2842, 1623, 1581, 1463, 1261, 1150, 1090, 1020 cm$^{-1}$; HRMS (ESI) calcd for C$_{14}$H$_{13}$NO$_4$S [M+Na]$^+$ 314.0457, found 314.0463.

14.5. trans-N-(4-Methoxybenzenesulfonyl)-hex-2-en-1-imine

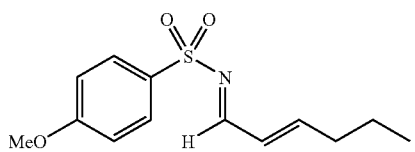 [SMILES: CCC/C=C/C=N/S(=O)(=O)c1ccc(OC)cc1]

Yellow solid; mp=45-48° C.; $^1$H NMR (400 MHz, CDCl$_3$) δ 8.57 (d, 1H, J=9.4 Hz), 7.05 (dd, 2H, J=6.7, 2.0 Hz), 7.00 (dd, 2H, J=6.7, 2.0 Hz), 6.87 (dt, 1H, J=15.4, 7.0 Hz), 6.35 (dd, 1H, J=15.4, 9.4 Hz), 3.87 (s, 3H), 2.35-2.29 (m, 2H), 1.53 (q, 2H, J=7.3 Hz), 0.94 (t, 3H, J=7.4 Hz); $^{13}$C NMR (100 MHz, CDCl$_3$) δ 171.0, 163.7, 160.6, 130.2, 129.6, 128.5, 114.5, 114.5, 55.8, 35.6, 21.2, 13.7; IR (thin film) ν 3087, 2963, 2934, 2874, 1636, 1595, 1498, 1323, 1262, 1154, 1092, 1023 cm$^{-1}$; HRMS (ESI) calcd for C$_{13}$H$_{17}$NO$_3$S [M+Na]$^+$ 290.0821, found 290.0815.

14.6. trans-N-(4-Methoxybenzenesulfonyl)-3-(4-bromophenyl)prop-2-en-1-imine

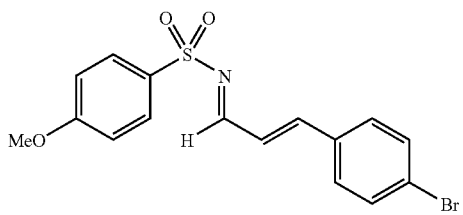

Yellow solid; mp=170-173° C.; $^1$H NMR (400 MHz, CDCl$_3$) δ 8.74 (d, 1H, J=9.4 Hz), 7.90 (d, 2H, J=8.9 Hz), 7.56 (d, 2H, J=8.9 Hz), 7.43-7.39 (m, 3H), 7.02-6.99 (m, 3H), 3.88 (s, 3H); $^{13}$C NMR (100 MHz, CDCl$_3$) δ 170.2, 164.0, 152.0, 133.3, 132.7, 130.4, 130.0, 129.7, 126.3, 125.5, 114.7, 55.9; IR (thin film) ν 3028, 2840, 1620, 1594, 1575, 1320, 1261, 1152, 1091, 1024 cm$^{-1}$; HRMS (ESI) calcd for C$_{16}$H$_{14}$BrNO$_3$S [M+Na]$^+$ 401.9769, found 401.9786.

Example 15

Preparation of the Triazolium Salt Precatalysts

15.1. (Z)-1-mesityl-2-((4aS,9aR)-4,4-a,9,9a-tetrahydroindeno[2,1-b][1,4]oxazin-3(2H)-ylidene)hydrazine hydrochloride

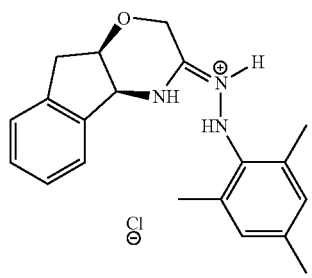 [SMILES: Cc1cc(C)c(N/[NH+]=C2/CO[C@@H]3Cc4ccccc4[C@@H]3N2)c(C)c1 ; [Cl-]]

The title compound was prepared by a modification of a literature route to a similar compound (Kerr, M. S.; Read de Alaniz, J.; Rovis, T. *J. Org. Chem.* 2005, 70, 5725-5728). To a 10 mL round bottom flask was added (4aR,9bR)-2-methoxy-4,4-a,5,9b-tetrahydro-3H-indeno[1,2-b]pyridine (0.15 g, 0.74 mmol, 1.00 equiv), 1-mesitylhydrazine hydrochloride (0.14 g, 0.74 mmol, 1.00 equiv), followed by 3.0 mL of MeOH. The mixture was stirred at room temperature under Ar until all solids were dissolved. Next, anhydrous HCl (4M in dioxane) was added (0.015 mL, 0.074 mmol, 0.10 equiv) and the flask equipped with a water-jacketed condenser. The orange solution was heated at 60° C. under Ar for 48 hours. Upon cooling to room temperature the solution was concentrated in vacuo to afford a tan solid. The solid was dissolved in 5 mL CH$_2$Cl$_2$ and diethyl ether added slowly with swirling until the solution became cloudy. Another 20 mL of diethyl ether was added slowly and the two-layer mixture was allowed to stand several hours at 0° C. The tan solid was collected by vacuum filtration. The filtrate was then filtered and the process repeated to afford (Z)-1-mesityl-2-((4aS,9aR)-4,4-a,9,9a-tetrahydroindeno[2,1-b][1,4]oxazin-3(2H)-ylidene)hydrazine hydrochloride (0.18 g, 0.57 mmol, 77%) as a tan solid.

15.2. 2-Mesityl-6,10b-dihydro-4H,5aH-(5S)-oxa-3,10c-diaza-(2R)-azoniacyclopenta[c]fluorene

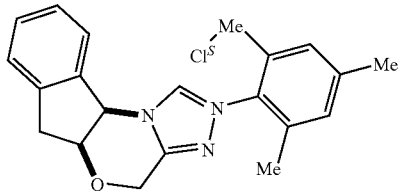

A 100 mL sealed tube flask was charged with (Z)-1-mesityl-2-((4aS,9aR)-4,4-a,9,9a-tetrahydroindeno[2,1-b][1,4]oxazin-3(2H)-ylidene)hydrazine hydrochloride (0.354 g, 1.75 mmol, 1.00 equiv), triethylorthoformate (2.40 mL, 17.5 mmol, 10.0 equiv), chlorobenzene (1.80 mL, 17.5 mmol, 10.0 equiv), and anhydrous HCl (4.0 M in dioxane; 0.44 mL, 1.75 mmol, 1.0 equiv). The flask was evacuated and then backfilled with dry Ar two times. The reaction mixture was heated to 120° C. for 1 h. Upon cooling to room temperature, the brown solution was transferred to 100 mL RB flask, the reaction flask washed 3×5 mL $CH_2Cl_2$, and the combined solutions concentrated in vacuo to a brown oil. The brown oil was twice azeotroped with 3 mL of toluene and concentrated to a light tan solid. The tan solid was refluxed in toluene (0.3M) and diethyl ether slowly added until the solution became slightly cloudy. The solution was slowly cooled to RT, 0° C., then −23° C. A white crystalline solid was collected (0.45 g, 78%). White solid; $[\alpha]_D^{20}$ (c 1.00, EtOH)=+129.3; $^1$H NMR (400 MHz, DMSO) δ 11.46 (s, 1H), 7.67 (d, 1H, J=7.3 Hz), 7.45-7.33 (m, 3H), 7.21 (s, 2H), 6.14 (d, 1H, J=3.8 Hz), 5.26 (d, 1H, J=16.0 Hz), 5.08 (d, 11-1, J=16.0 Hz), 4.99 (t, 1H, J=4.3 Hz), 3.49 (dd, 1H, J=4.9 Hz, 17.1 Hz), 3.16 (d, 1H, J=17.1 Hz), 2.37 (s, 3H), 2.12 (s, 6H); $^{13}$C NMR (100 MHz, DMSO) δ 150.2, 144.7, 141.5, 140.7, 136.1, 134.9, 131.3, 129.4, 129.3, 127.3, 125.5, 124.0, 76.9, 61.2, 59.8, 37.1, 20.7, 17.0; IR (thin film) ν 2923, 2853, 1580, 1460, 1222, 1099 cm$^{-1}$; HRMS (ESI) calcd for $C_{21}H_{22}N_3O^+$ [M]$^+$ 332.1757, found 332.1754. For the (S,R)-enantiomer: $[\alpha]_D^{20}$ (c 1.00, EtOH)=−129.4.

Example 16

Determination of the Relative and Absolute Stereochemistry of the Dihydropyridinone Products The stereochemistry was determined by single crystal x-ray analysis of the product derived from 4-bromo-cinnamaldehyde imine (see above for characterization details): A colorless crystal of approximate dimensions 0.3*0.2*0.09 mm was mounted on a glass fiber and transferred to a Bruker CCD platform diffractometer. The SMART program (SMART Software Users Guide, Version 5.1, Bruker Analytical X-ray Systems, Inc., Madison, Wis. 1999) was used to determine the unite cell parameters and data collection (20 sec/frame, 0.3 deg./frame for a sphere of diffraction data). The data were collected at room temperature. The raw frame data were processed using SAINT program (SAINT Software Users Guide, Version 5.1, Bruker Analytical X-ray Systems, Inc., Madison, Wis. 1999). The absorption correction was applied using program SADABS (Sheldrick, G. M. SADABS, Version 2.05, Bruker Analytical X-ray Systems, Inc.; Madison, Wis. 2001). The structure was solved by direct methods and refined on F2 by full-matrix least-squares techniques. Hydrogen atoms were theoretically added. At convergence, GOF=1.099 for 288 variables refined to R1=0.0822 for 1517 reflections with I>2σ(I). The absolute structure was determined from the Flack parameters (Flack, H. D., *Acta Cryst. A39* (1983) 876-881). The two enantiomers gave the Flack parameters −0.03(2) and 1.04(0.03), respectively.

Example 17

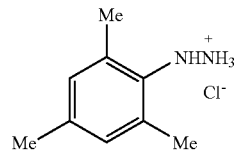

Mesityl Hydrazine Hydrochloride

A 3.0 L, 3-neck round bottom flask equipped with a mechanical stirrer and an addition funnel was charged with concentrated hydrochloric acid (0.125 L) and deionized water (0.100 L). The solution was cooled to −5° C. in an ice/salt water bath, and 2,4,6-trimethylaniline (70 mL, 0.50 mol, 1.0 equiv.) was added dropwise over 30 minutes; during this time a white precipitate formed. The mixture was stirred for an additional 15-20 minutes before 52.5 mL of a 9.5 M aq. solution of sodium nitrite (70 mL, 0.50 mol, 1.0 equiv.) was added dropwise over 30-45 minutes. The resulting brown solution was allowed to stir for 30 minutes before a 3.3 M solution of stannous chloride dihydrate in 1:1 concentrated HCl:$H_2O$ (0.455 L, 1.5 mol, 2.5 equiv.) was added over 4 hours with vigorous stirring. (Upon addition of the stannous chloride solution a thick light orange slurry had formed which sometimes caused seizure of the mechanical stirrer. Addition small amounts of deionized water helped to facilitate stirring again.) The mixture was allowed to warm to room temperature and stirred vigorously for 16 hours. The mixture was cooled to 0° C. for 1 hour before filtering through a fine porosity glass fritted buchner funnel, and the collected orange solid washed with brine and diethyl ether. This orange solid was added to a 2-L round-bottom charged with 10 M NaOH (aq) (1.0 L) and diethyl ether (0.700 L) and cooled to −5° C. Once nearly all of the solid had dissolved (ca. 1 h), the organic layer was removed, and the aqueous layer extracted with diethyl ether (2×0.400 L). The combined organic fractions were dried over $Na_2SO_4$, filtered into a flame-dried 2.0 L round-bottom flask, placed under an atmosphere of $N_2(g)$, cooled to 0° C., and treated with 4 M HCl in 1,4-dioxane (0.125 L). A white precipitate formed, was collected by vacuum filtration, washed with diethyl ether, and recrystallized from 200 proof EtOH to afford the title compound (50 g, 0.27 mol, 54%) as a white powder. $^1$H NMR (400 MHz, DMSO) δ 9.57 (3H, s, br, NH, varies), 6.89 (s, 2H), 2.33 (s, 6H), 2.21 (s, 3H); $^{13}$C NMR (100 MHz, DMSO) δ 138.06, 136.20, 135.01, 129.17, 20.54, 17.95; IR (thin film) ν 3294, 3002, 2964, 2911, 2680, 1564, 1513, 1481, 852, 825, 753 cm$^{-1}$; HRESI+/TOF-MS calcd for $C_9H_{15}N_2^+$ [M]$^+$ 151.1230, found 134.0921 for aniline anion radical (134.0975).

Synthesis of 1

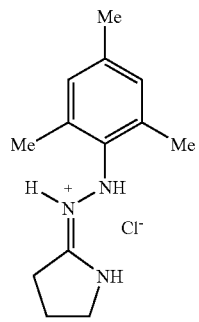

1

A flame dried flask was charged with a 0.5 M solution of 5-methoxy-3,4-dihydro-2H-pyrrole (which had been passed through a plug of $Na_2SO_4$ prior to its usage) (1.00 g, 10.1 mmol, 1.01 equiv.) in anhydrous methanol and mesityl hydrazine hydrochloride (1.87 g, 10.0 mmol, 1.00 equiv.) was added. The solution was heated to 50° C. and conversion to the product monitored by 1HNMR, (ca 30 min.), during this time it had became deep red in color. The solution was cooled to room temperature and concentrated in vacuo to the crude solid which was subsequently twice recrystallized from 200 proof EtOH to afford the title compound as a white powder (1.64 g, 6.5 mmol, 65% yield). $^1$H NMR (400 MHz, DMSO) δ 10.87 (s, 1H), 10.08 (s, 1H), 7.14 (s, 1H), 6.86 (s, 2H), 3.63 (t, 2H, J=8.0 Hz), 2.81 (t, 2H, J=8.0 Hz), 2.19 (s, 6H), 2.18 (s, 3H), 2.15 (shoulder, m, 2H); HRESI+/TOF-MS calcd for $C_{13}H_{20}N_3^+$ [M]$^+$ 218.1652; found, 218.1646

Synthesis of 2

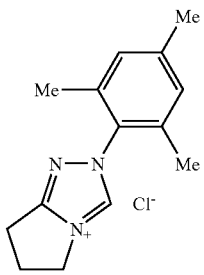

2

To a flame dried sealed tube flask charged with a magnetic stir bar charged with of 2-mesityl-1-(pyrrolidin-2-ylidene) hydrazinium chloride (0.90 g, 3.5 mmol, 1 equiv.) under a blanket of $N_2$(g) was added chlorobenzene (3.6 mL, 35 mmol, 10 equiv.), of triethylorthoformate (4.7 mL, 35 mmol, 10 equiv.) and 4 M HCl in 1,4-dioxane (0.88 mL, 3.5 mmol, 1.0 equiv.). The mixture was heated to 120° C. until all of the solid starting material had dissolved (ca 1 h). The tan solution was cooled to room temperature and concentrated in vacuo. The resultant oil was azeotroped twice with toluene to afford a crude brown solid which was recrystallized from toluene to give the title compound as a crystalline white solid (580 mg, 2.0 mmol, 63% yield). $^1$H NMR (400 MHz, MeOD) δ 4.54 (t, 2H, J=7.4 Hz), 3.26 (t, 2H, J=7.4 Hz), 2.93-2.87 (m, 2H), 2.37 (s, 3H), 2.11 (s, 6H); $^{13}$C NMR (100 MHz, MeOD) δ 165.2, 143.4, 136.7, 133.6, 130.7, 48.7, 27.8, 22.7, 21.3, 17.4 IR (thin film) ν 2978, 1591, 1448, 1388, 1294, 1084, 1033, 855 cm$^{-1}$; HRESI+/TOF-MS calcd for $C_{14}H_{18}N_3^+$ [M]$^+$ 228.1495, found 228.1489.

Synthesis of 3

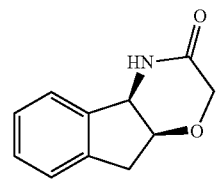

3

To a flame dried 3.0 L flask with a magnetic stir bar was added sodium hydride (7.1 g, 168 mmol, 1.25 equiv., 57-61% oil dispersion). The sodium hydride was washed twice with 200 mL of dry pentane, which was removed each time via cannula. Anhydrous THF (2.0 L) was added and the mixture cooled to 0° C. in an ice bath. To the stirring mixture was added (1S,2R)-(−)-cis-1-amino-2-indanol (20 g, 0.134 mol, 1 equiv.) in two equal portions 15 minutes apart. The flask was equipped with a reflux condenser and the mixture heated to 70° C. for 40 minutes, during which time the mixture became light purple in color. The mixture was cooled again to 0° C. and ethyl chloroacetate (18.5 mL, 0.134 mol, 1 equiv.) was added dropwise over 30 minutes. The resulting dark purple solution was then refluxed for 2 hours under $N_2$(g). After cooling to room temperature, the solution washed with brine (2×700 mL). The combined aqueous fractions were back extracted with ethyl acetate (2×500 mL). The combined organic fractions were stirred vigorously over $MgSO_4$ (150 g) for 12 hours. The mixture was then filtered and concentrated in vacuo to afford the crude product as a light tan or grey solid in quantitative yield. The product was suitable for the next reaction without further purification. The opposite enantiomer was prepared in the same manner.

Synthesis of 4

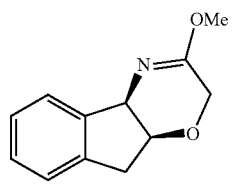

4

Trimethyloxonium tetrafluoroborate (21.4 g, 0.145 mol, 1.1 equiv.) was added to a 0.25 M solution of 4,4a,9,9a-Tetrahydro-1-oxa-4-aza-fluoren-3-one (25 g, 0.13 mol, 1 equiv.) in anhydrous dichloromethane (0.53 L). The resulting solution was stirred at room temperature under $N_2$(g) for 16 hours. The solution was cooled to 0° C. and sat. $NaHCO_3$(aq) (500 mL) was added over 2 hours. The mixture was transferred to a seperatory funnel, the organic layer removed, and the aqueous layer extracted with dichloromethane (2×300 mL). The combined organics were dried over $Na_2SO_4$, filtered, and concentrated in vacuo. The crude product was purified by flash column chromatography (95:5 Hexanes:Isopropanol) to afford the desired compound as a crystalline white solid (18.4 g, 0.090 mol, 68% yield). The opposite enantiomer was prepared in the same manner.

Synthesis of 5

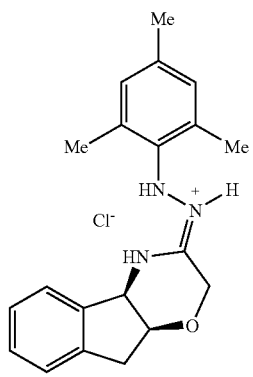

5

To a 0.25 M solution of 4 (18.35 g, 90.0 mmol, 1.00 equiv.) in anhydrous methanol (360 mL) was added mesityl hydrazine hydrochloride (16.9 g, 90.0 mmol, 1.00 equiv.) and 4 M HCl in 1,4-dioxane (2.25 mL, 9.00 mmol, 0.100 equiv.). The flask was equipped with a water-jacketed reflux condenser and the red solution heated at 60° C. for 48 hours under an atmosphere of $N_2(g)$. The solution was allowed to cool to room temperature and then concentrated in vacuo to give a crude orange solid. To the solid was added anhydrous ethyl acetate (10 mL/1 g) which then formed an insoluble oil. The mixture was heated to reflux (100° C.) with vigorous stirring. Once the oil precipitated as a tan solid, the mixture was allowed to cool to room temperature, and the precipitate collected by vacuum filtration and washed with anhydrous ethyl acetate to give the title compound (27.9 g, 88.3 mmol, 98% yield). The opposite enantiomer was prepared in the same manner. $^1$H NMR (400 MHz, DMSO) δ 11.26 (s, 1H), 11.09 (d, 1H, J=3.4 Hz), 9.60 (s, 1H), 7.69 (m, 1H), 7.30 (m, 3H), 7.12 (s, 1H), 6.87 (s, 2H), 4.99 (t, 1H, J=3.7 Hz), 4.72 (t, 1H, J=4.6 Hz), 4.62 (d, 1H, J=16.5 Hz), 4.51 (d, 1H, J=16.6 Hz), 3.29 (dd, 1H, J=4.6 Hz, 16.9 Hz), 2.96 (d, 1H, 16.9 Hz), 2.33 (s, 3H), 2.20 (s, 6H); $^{13}$C NMR (100 MHz, DMSO) 159.4, 140.2, 139.8, 138.3, 137.9, 136.4, 135.1, 134.0, 131.2, 129.5, 129.2, 128.2, 126.8, 124.9, 77.0, 60.1, 56.2, 37.2, 20.5, 20.4, 17.9, 17.9; IR (thin film) ν 3294, 3119, 2997, 2966, 2951, 2918, 2731, 2692, 1676, 1514, 1483, 1335, 739 cm$^{-1}$; HRMS (ESI) calcd for $C_{20}H_{24}N_3O^+$ [M]$^+$ 322.1914, found 322.1912.

Synthesis of 6

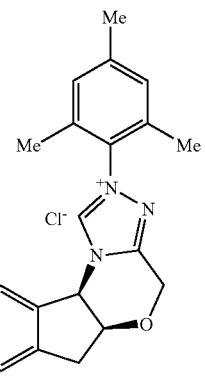

6

To a flame-dried sealed tube flask charged with a magnetic stir bar and 5 (28 g, 88 mmol, 1.0 equiv.) under an atmosphere of $N_2(g)$ was added chlorobenzene (90 mL, 880 mmol, 10 equiv.), of triethylorthoformate (120 mL, 880 mmol, 10 equiv.) and 4 M HCl in 1,4-dioxane (22 mL, 88 mmol, 1.0 equiv.). The mixture was heated to 120° C. until all of the solid starting material had dissolved (ca 1 h). The tan solution was cooled to rt and concentrated in vacuo. The resultant oil was azeotroped twice with toluene to afford a crude brown solid that was suspended in hot toluene with vigorous stirring (excessive heating above 100° C. often resulted in decomposition of the product and thus decreased yield). The product solid product was collected by vacuum filtration and washed with diethyl ether to afford the title compound as a white powder (19 g, 58 mmol, 66% yield). $[\alpha]_D^{20}$ (c 1.00, EtOH)=−129.4; NMR (400 MHz, DMSO) δ 11.53 (s, 1H), 7.69 (d, 1H, J=7.3 Hz), 7.44-7.34 (m, 3H), 7.20 (s, 2H), 6.16 (d, 1H, J=3.5 Hz), 5.25 (d, 1H, J=16.0 Hz), 5.09 (d, 1H, J=16.0 Hz), 5.00 (t, 1H, J=4.1 Hz), 3.49 (dd, 1H, J=4.9 Hz, 16.9 Hz), 3.15 (d, 1H, J=16.9 Hz), 2.37 (s, 3H), 2.12 (s, 6H); $^{13}$C NMR (100 MHz, DMSO) δ 150.2, 141.6, 140.8, 136.2, 135.0, 131.3, 129.5, 129.4, 129.4, 127.4, 125.6, 124.2, 77.0, 61.3, 59.9, 37.1, 20.8, 17.1; IR (thin film) ν 2923, 2853, 1581, 1460, 1223, 1099 cm$^{-1}$; HRESI+/TOF-MS calcd for $C_{21}H_{22}N_3O^+$ [M]$^+$ 332.1757, found 332.1760.

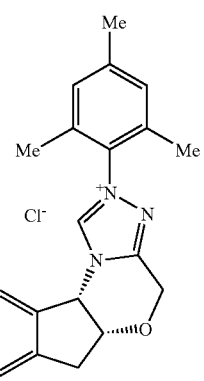

Prepared according to the procedure for 6. $[\alpha]_D^{20}$ (c 1.00, EtOH)=+129.3; $^1$H NMR (400 MHz, DMSO) δ 11.46 (s, 1H), 7.67 (d, 1H, J=7.3 Hz), 7.45-7.33 (m, 3H), 7.21 (s, 2H), 6.14 (d, 1H, J=3.8 Hz), 5.26 (d, 1H, J=16.0 Hz), 5.08 (d, 1H, J=16.0 Hz), 4.99 (t, 1H, J=4.3 Hz), 3.49 (dd, 1H, J=4.9 Hz, 17.1 Hz), 3.16 (d, 1H, J=17.1 Hz), 2.37 (s, 3H), 2.12 (s, 6H); $^{13}$C NMR (100 MHz, DMSO) δ 150.2, 144.7, 141.5, 140.7, 136.1, 134.9, 131.3, 129.4, 129.3, 127.3, 125.5, 124.0, 76.9, 61.2, 59.8, 37.1, 20.7, 17.0; IR (thin film) ν 2923, 2853, 1580, 1460, 1222, 1099 cm$^{-1}$; HRESI+/TOF-MS calcd for $C_{21}H_{22}N_3O^+$ [M]$^+$ 332.1757, found 332.1754

Example 17

Synthesis of 7

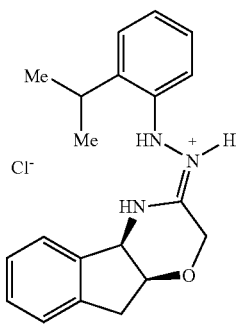

7

To a 0.25 M solution of 4 (0.250 g, 1.23 mmol, 1.00 equiv.) in anhydrous methanol (5.6 mL) was added o-isopropyl hydrazine hydrochloride (0.230 g, 1.23 mmol, 1.00 equiv.) and 4 M HCl in 1,4-dioxane (0.031 mL, 0.123 mmol, 0.123 equiv.). The flask was equipped with a water-jacketed reflux condenser and the red solution heated at 60° C. for 48 hours under an atmosphere of N$_2$(g). The solution was allowed to cool to room temperature and then concentrated in vacuo to give a crude orange solid. The crude solid was recrystallized from 200 proof EtOH to give the title compound (0.440 g, 1.23 mmol, 100% yield). $^1$H NMR (400 MHz, DMSO) δ 11.31 (s, 1H), 10.84 (s, 1H), 9.87 (s, 1H), 7.51-7.46 (m, 1H), 7.32-7.08 (m, 5H), 6.99-6.91 (m, 1H), 6.84 (dd, 1H, J=11.7, 8.1), 4.92 (t, 1H, J=4.3 Hz), 4.75-4.71 (m, 2H), 4.56 (d, 1H, J=16.6 Hz), 3.29 (d, 1H, J=16.9 Hz, shoulder HOD), 3.14-3.05 (m, 1H), 2.95 (d, 1H, J=16.9 Hz), 1.23-1.28 (m, 61-1).

Synthesis of 8

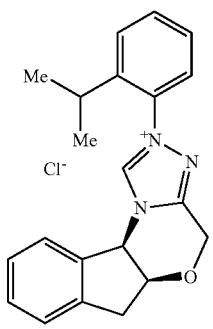

8

To a flame-dried sealed tube flask charged with a magnetic stir bar and 7 (0.880 g, 2.46 mmol, 1.00 equiv.) under an atmosphere of N$_2$(g) was added chlorobenzene (2.50 mL, 24.6 mmol, 10.0 equiv.), of triethylorthoformate (3.30 mL, 24.6 mmol, 10.0 equiv.) and 4 M HCl in 1,4-dioxane (0.62 mL, 2.46 mmol, 1.00 equiv.). The mixture was heated to 120° C. for 1.0 hour. The tan solution was cooled to rt and concentrated in vacuo. The resultant oil was azeotroped with toluene to afford a crude brown solid that was recrystallized from toluene. The solid wad dissolved from the filter with MeOH and then concentrated to a tan solid as the title compound (0.39 g, 1.1 mmol, 43% yield). $^1$H NMR (400 MHz, DMSO) δ 11.23 (s, 1H), 7.72 (d, 2H, J=4.0 Hz), 7.67 (d, 2H, J=7.8 Hz), 7.54-7.49 (m, 1H), 7.45-7.33 (m, 3H), 6.06 (d, 1H, J=3.7 Hz), 5.29 (d, 1H, J=16.2 Hz), 5.08 (d, 1H, J=16.2 Hz), 4.96 (t, 1H, J=4.3 Hz), 3.48 (dd, 1H, J=16.8, 5.2 Hz), 3.16 (d, 1H, J=5.2 Hz), 2.93-2.88 (m, 1H), 1.21 (dd, 6H, J=16.5, 6.8 Hz).

Example 19

Synthesis of 9

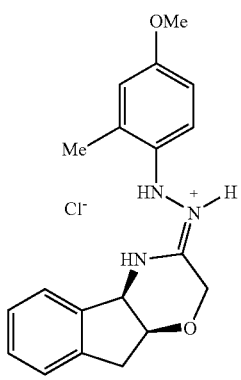

9

To a 0.25 M solution of 4 (0.30 g, 1.5 mmol, 1.0 equiv.) in anhydrous methanol (6.8 mL) was added o-methyl-p-methoxy hydrazine hydrochloride (0.28 g, 1.5 mmol, 1.0 equiv.). The flask was equipped with a water-jacketed reflux condenser and the orange solution heated at 60° C. for 1.5 hours under an atmosphere of N$_2$(g). The solution was allowed to cool to room temperature and then concentrated in vacuo to give a crude solid. The crude solid was recrystallized from EtOAc to give the title compound (0.42 g, 1.2 mmol, 77% yield). $^1$H NMR (200 MHz, DMSO) δ 11.33 (s, 1H), 10.86 (s, 1H), 7.67 (s, 1H), 7.56-7.54 (m, 2H), 7.32-7.22 (m, 3H), 6.84-6.69 (m, 3H), 4.93-4.55 (m, 4H), 3.69 (s, 3H), 3.30-3.20 (m, 1H, shoulder HOD), 2.97 (d, 1H, J=16.8 Hz), 2.25 (s, 1H).

Synthesis of 10

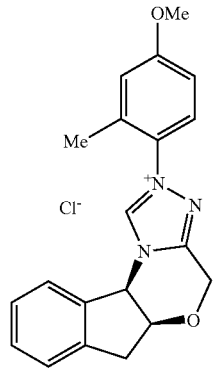

To a flame-dried sealed tube flask charged with a magnetic stir bar and X (0.42 g, 1.2 mmol, 1.0 equiv.) under an atmosphere of $N_2(g)$ was added chlorobenzene (1.2 mL, 12 mmol, 10 equiv.), of triethylorthoformate (1.6 mL, 12 mmol, 10.0 equiv.) and 4 M HCl in 1,4-dioxane (0.29 mL, 1.2 mmol, 1.0 equiv.). The mixture was heated to 120° C. for 1.0 hour. The tan solution was cooled to rt and concentrated in vacuo. The resultant oil was azeotroped with toluene to afford a crude brown solid that was recrystallized from toluene. (0.27 g, 0.73 mmol, 62% yield). $^1$H NMR (400 MHz, DMSO) δ 11.14 (s, 1H), 7.68 (d, 1H, J=7.2 Hz), 7.61 (d, 1H, J=8.7 Hz), 7.42-7.35 (m, 3H), 7.12 (d, 1H, J=2.6 Hz), 7.06 (dd, 1H, J=8.7, 2.9 Hz), 6.02 (d, 1H, J=4.0 Hz), 5.27 (d, 1H, J=16.2 Hz), 5.06 (d, 1H, J=16.2 Hz), 4.94 (t, 1H, J=4.6 Hz), 3.86 (s, 3H), 3.48 (dd, 1H, J=16.9, 4.6), 3.16 (d, 1H, J=16.9 Hz), 2.31 (s, 3H).

Example 20

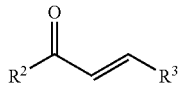

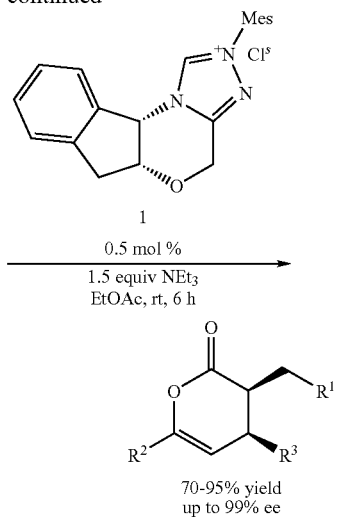

We now document chiral NHC-catalyzed, highly enantioselective 1-oxodiene Diels-Alder reactions of a broad range of enones, using racemic α-chloroaldehydes as the dienophile precursors. This process affords a diverse set of non-racemic, 3,4,6-trisubstituted dihydropyran-2-ones from readily available starting materials under mild, simple conditions (rt, 1.5 equiv $NEt_3$, 6 h). Significantly, when the NHC-catalyzed oxo-diene Diels-Alder reactions are performed in EtOAc, the loading of the chiral organocatalyst can be reduced to 0.5 mol % without compromising the reaction rate, enantioselectivity, or chemical yield. This is an unparalleled example of a highly enantioselective, intermolecular C—C bond-forming reaction catalyzed by less than 1 mol % of a small organic molecule.

Using our recently reported chiral triazolium salt 1 as a precatalyst, we screened an assortment of bases, solvents, and reaction stoichiometries. The reaction proceeded cleanly under a number of conditions, although annulations performed in ethyl acetate with $NEt_3$ were notably faster and higher yielding. Significantly, this finding allowed us to identify useful conditions (1.6 equiv aldehyde, 1.5 equiv $NEt_3$, 0.2 M EtOAc, rt) for oxodiene Diels-Alder reactions employing only 0.5 mol % of chiral organocatalyst 1.

A range of enones bearing an electron-withdrawing group were viable reaction partners (Table 1).

TABLE 1

Catalytic, asymmetric oxodiene Diels-Alder reactions.[a]

| | | | | | | |
|---|---|---|---|---|---|---|
| entry | $R^1$ = | $R^2$ = | product | d.r. | % yield[b] | % ee[c] |
| 1 | Ph | Me | 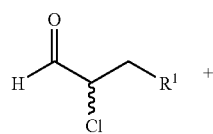 | >20:1[d] | 88 | 99 (S,S) |

TABLE 1-continued

| | | | | | | |
|---|---|---|---|---|---|---|
| 2 | Ph | Ph | 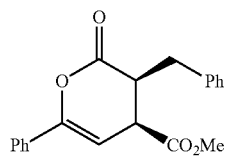 | 8:1 | 91 | 99 (S,S) |
| 3[e] | Ph | Ph | | 15:1 | 98 (70)[f] | 99 (S,S) |
| 4 | Ph | p-Br—C$_6$H$_4$ | 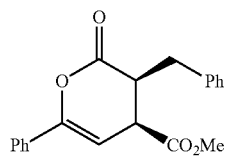 | 6:1 | 80 | 99 (S,S) |
| 5[g] | Ph | c-Hex | 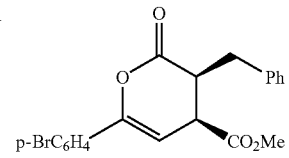 | >20:1[d] | 76 | 86 (S,S) |
| 6 | Ph | Furyl | 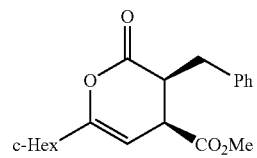 | 8:1[d] | 94 | 99 (S,S) |
| 7 | n-C$_9$H$_{19}$ | Me | 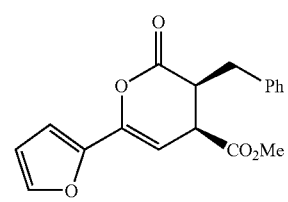 [SMILES: COC(=O)[C@H]1C=C(c2ccco2)OC(=O)[C@H]1Cc1ccccc1] | >20:1[d] | 71 | 99 (S,S) |
| 8 | n-C$_9$H$_{19}$ | Ph | 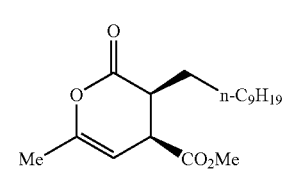 | >20:1[d] | 90 | 99 (S,S) |
| 9 | OTBS | Ph | 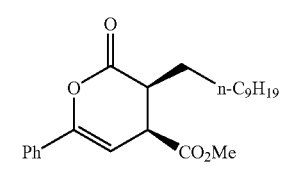 | 3:1 | 80 | 97 (R,S) |

[a]All reactions were performed on a 0.5 mmol scale for 2-8 h.
[b]Yield of diastereomeric mixtures after chromatography.
[c]Determined by HPLC analysis on Chiralpak columns (see Supporting Information).
[d]A single diastereomer was detected by $^1$H NMR of unpurified reaction mixtures.
[e]24 mmol scale, 2 h;
[f]Isolated yield of >50:1 d.r. material obtained by crystallization of the unpurified product.

Our studies focused on the use of either aromatic or aliphatic substituted 4-oxo-enoates, which in all cases tested afforded the desired product in good yield and with outstanding enantioselectivity. A sole exception was a hindered ketone, which required a longer reaction time and gave the product in lower than usual enantioselectivity (entry 5). The lower diastereoselectivities observed with the aryl ketone derivatives (entries 2, 4, 6, 9) appear to result from epimerization of the initially formed cis-annulation products. A variety of α-chloroaldehydes were efficient precursors (entries 7-9).

Alternatively, b,γ-unsaturated, α-ketoesters proved to be highly reactive substrates and afforded synthetically valuable products in excellent yields and stereoselectivities (Table 2).

TABLE 2

NHC-catalyzed reactions of unsaturated-α-ketoesters.[a]

| entry | R[1] = | R[2] = | product | % yield[b] | % ee[c] |
|---|---|---|---|---|---|
| 1 | Ph | p-Tol | | 74 | 97 (S,S) |
| 2 | Ph | n-Pr | | 84 | 98 (S,S) |
| 3 | Ph | c-Hex | | 85 | 95 (S,S) |
| 4 | n-C$_9$H$_{19}$ | p-Tol | | 70 | 99 (S,S) |
| 5 | OTBS | p-Tol | | 83 | 95 (R,S) |

[a]All reactions were performed at on a 0.2 mmol scale for 6-8 h. In all cases, only a single diastereomer was detected in unpurified reaction mixtures.
[b]Isolated yield after chromatography.
[c]Determined by HPLC analysis on Chiralpak columns.

These reactions could proceed with less than 1 mol % catalyst, but the 2 mol % loading proved optimal in chemical yield and enantioselectivity. This variant also tolerated a wide scope of enones, including both aromatic and aliphatic substitution.

The use of readily prepared racemic α-chloroaldehydes as enolate precursors greatly expands the scope of enantioselective N-heterocyclic carbene-catalyzed Diels-Alder reactions. It also makes possible, for the first time, asymmetric annulations with exceptional enantioselectivities under reliable conditions with less than 1 mol % of a chiral NHC-catalyst.

Example 21

Preparative Scale Enantioselective Oxodiene Diels-Alder Reactions

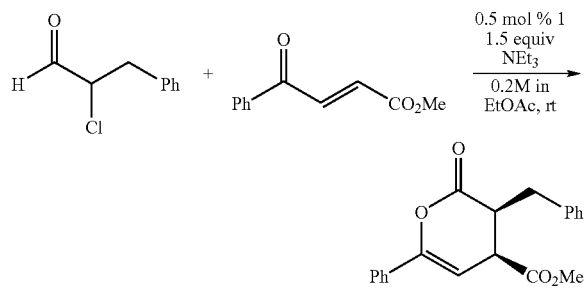

Into an oven dried 200 ml round-bottom flask was added 2-chloro-hydrocinnamaldehyde (6.40 g, 38.0 mmol, 1.6 equiv) and (E)-methyl 4-oxo-4-phenylbut-2-enoate (4.51 g, 23.7 mmol, 1.0 equiv). To this mixture was added 120 ml EtOAc (0.2 M), followed by addition of triazolium salt (He, M.; Struble, J. R.; Bode, J. W. *J. Am. Chem. Soc.* 2006, 128, 8418-8420), (See catalyst in Example 20) (44 mg, 0.12 mmol, 0.5 mol %) and $NEt_3$ (5.0 ml, 36 mmol, 1.5 equiv). The white $NEt_3 \cdot HCl$ salt precipitated in 2-5 minutes. The reaction was stirred under Ar for 2 hours. Water was added to the vial and the mixture was extracted with EtOAc (3×100 ml). The combined EtOAc extract was washed with brine and dried over anhydrous $NaSO_4$. The solution was concentrated under reduced pressure, and the resulting pale yellow solid was recrystallized from 10:1 hexane/EtOAc to afford 5.29 g white solid as a single diasteromer. The residue was purified by silica gel chromatography (10:1 hexane/EtOAc) to afford another 2.19 g as a 4:1 mixture of diastereomers. The combined yield was 98% with 15:1 dr (7.48 g, 23.2 mmol).

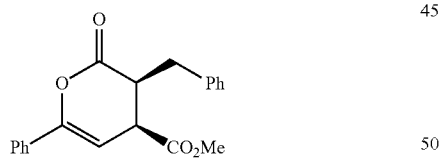

(3S,4S)-Methyl 3-benzyl-6-phenyl-2-oxo-3,4-dihydro-2H-pyran-4-carboxylate (Table 1, entry 3) $[\alpha]_D^{20}$ (c 1.20, $CHCl_3$)=+151.2; mp=105-106° C.; $^1H$ NMR (400 MHz, $CDCl_3$) δ 7.63-7.61 (m, 2H), 7.39-7.27 (m, 6H), 7.27-7.17 (m, 2H), 5.81 (d, 1H, J=7.0 Hz), 3.76 (s, 3H), 3.55 (dd, 1H, J=14.3, 4.6 Hz), 3.31-3.28 (m, 1H), 3.04-2.99 (m, 1H), 2.76 (dd, 1H, J=14.3, 10.1 Hz); $^{13}C$ NMR (100 MHz, $CDCl_3$) δ 170.9, 168.9, 152.6, 138.2, 131.8, 129.8, 129.2, 129.1, 128.8, 127.1, 125.0, 98.1, 52.8, 42.8, 40.6, 33.4; IR (thin film) ν 3061, 3028, 2952, 1777, 1733, 1496, 1448, 1173, 1069 $cm^{-1}$; HRMS (ESI) calcd for $C_{20}H_{18}O_4$ $[M+Na]^+$ 345.1097, found 345.1094; >99% ee (3S,4S)-isomer as determined by HPLC (AD-H, 9:1 hexanes/i-PrOH), $t_r$ (3S,4S)=32.4 min, $t_r$ (3R,4R)=20.3 min.

Example 22

General Procedure for NHC-Catalyzed, Enantioselective Oxodiene Diels-Alder Reactions

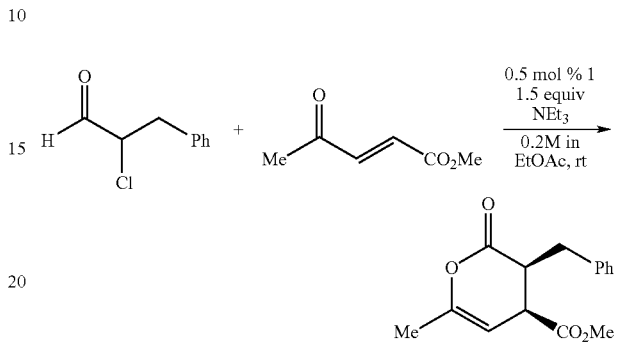

The reaction of 2-chloro-hydrocinnamaldehyde and (E)-methyl 4-oxopent-2-enoate is representative: Into an oven dried 4.0 mL vial was added 2-chloro-hydrocinnamaldehyde (146.0 mg, 0.87 mmol, 1.6 equiv), (E)-methyl 4-oxopent-2-enoate (77.8 mg, 0.54 mmol, 1.0 equiv) and (See catalyst in Example 20) (1.0 mg, 0.5 mol %). To this mixture was added 2.7 mL EtOAc (0.2 M), followed by $NEt_3$ (112 μL, 0.82 mmol, 1.5 equiv). The vial was capped and the white $NEt_3 \cdot HCl$ salt precipitated in 2~5 minutes. The mixture was stirred at rt for 6 h. Water was added to the vial and the mixture was extracted with EtOAc (2×5 ml). The combined EtOAc extract was washed with brine and dried over anhydrous $NaSO_4$. The solution was concentrated under reduced pressure, and the residue was purified by silica gel chromatography (10:1 hexane/EtOAc) to afford the product as a single diastereomer (123.2 mg, 88% yield).

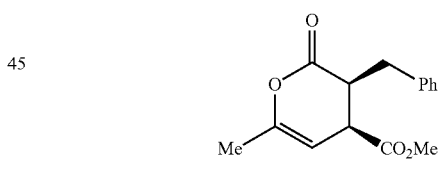

(3S,4S)-Methyl 3-benzyl-6-methyl-2-oxo-3,4-dihydro-2H-pyran-4-carboxylate (Table 1, entry 1)

Prepared according to the general procedure from 2-chloro-hydrocinnamaldehyde and (E)-methyl 4-oxopent-2-enoate using 0.5 mol % 1 as the catalyst in 88% yield as a single diasteromer (colorless oil). $[\alpha]_D^{20}$ (c 1.10, $CHCl_3$)=+218.7; $^1H$ NMR (400 MHz, $CDCl_3$) δ 7.32-7.23 (m, 3H), 7.12 (d, 2H, J=7.2 Hz), 5.02 (d, 1H, J=7.2 Hz), 3.73 (s, 3H), 3.48 (dd, 1H, J=14.3, 4.6 Hz), 3.02 (t, 1H, J=6.0 Hz), 2.89-2.84 (m, 1H), 2.66 (dd, 1H, J=14.3, 10.1 Hz), 1.89 (s, 3H); $^{13}C$ NMR (100 MHz, $CDCl_3$) δ 171.3, 169.3, 152.6, 138.3, 129.2, 129.0, 127.0, 98.7, 52.6, 42.8, 40.3, 33.4, 19.0; IR (thin film) ν 3062, 2954, 1780, 1732, 1496, 1435, 1362, 1164 $cm^{-1}$; HRMS (ESI) calcd for $C_{15}H_{16}O_4$ $[M+Na]^+$ 283.0940, found 283.0944; 99% ee (3S,4S)-isomer as determined by HPLC (AD-H, 9:1 hexanes/i-PrOH), $t_r$ (3S,4S)=12.0 min, $t_r$ (3R,4R)= 9.40 min.

Example 23

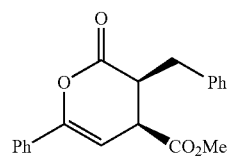 [SMILES: COC(=O)[C@H]1C=C(c2ccccc2)OC(=O)[C@H]1Cc1ccccc1]

(3S,4S)-Methyl 3-benzyl-6-phenyl-2-oxo-3,4-dihydro-2H-pyran-4-carboxylate (Table 1, entry 2)

Prepared according to the general procedure from 2-chloro-hydrocinnamaldehyde and (E)-methyl 4-oxo-4-phenylbut-2-enoate using 0.5 mol % 1 as the catalyst in 91% yield as a 8:1 mixture of diastereomers (white solid). $[\alpha]_D^{20}$ (c 1.16, CHCl$_3$)=+130.4; mp=103-106° C.; $^1$H NMR (400 MHz, CDCl$_3$) δ 7.67-7.61 (m, 2H), 7.41-7.27 (m, 6H), 7.27-7.17 (m, 2H), 5.82 (d, 1H, J=7.0 Hz), 5.75* (d, 1H, J=5.7 Hz), 3.77 (s, 3H), 3.69* (s, 3H), 3.61-3.58* (m, 1H), 3.56 (dd, 1H, J=14.3, 4.6 Hz), 3.42-3.37* (m, 1H), 3.32-3.28 (m, 1H), 3.17* (dd, 1H, J=13.8, 5.7 Hz), 3.04-2.99 (m, 1H), 2.92* (dd, 1H, J=13.8, 9.2 Hz), 2.77 (dd, 1H, J=14.3, 10.1 Hz); $^{13}$C NMR (100 MHz, CDCl$_3$) δ 170.8, 168.9, 152.6, 138.2, 131.8, 129.8, 129.4, 129.2, 129.0, 128.8, 127.4, 127.1, 125.0, 98.1, 95.9, 52.9, 52.8, 42.8, 42.3, 41.2, 40.6, 35.5, 33.4; IR (thin film) ν 3061, 3028, 2952, 1777, 1733, 1496, 1448, 1173, 1069 cm$^{-1}$; HRMS (ESI) calcd for C$_{20}$H$_{18}$O$_4$ [M+Na]$^+$ 345.1097, found 345.1094; >99% ee (3S,4S)-isomer as determined by HPLC (AD-H, 9:1 hexanes/i-PrOH), $t_r$ (3S,4S)=32.4 min, $t_r$ (3R,4R)=20.3 min.

Example 24

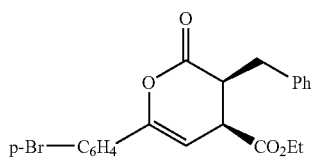

(3S,4S)-Methyl 3-benzyl-6-(4-bromophenyl)-2-oxo-3,4-dihydro-2H-pyran-4-carboxylate (Table 1, entry 4)

Prepared according to the general procedure from 2-chloro-hydrocinnamaldehyde and (E)-methyl 4-oxo-4-(4-bromophenyl)but-2-enoate using 0.5 mol % 1 as the catalyst in 80% yield as a 6:1 mixture of diastereomers (white solid). $[\alpha]_D^{20}$ (c 1.23, CHCl$_3$)=+112.1; mp=139-141° C.; $^1$H NMR (400 MHz, CDCl$_3$) δ 7.53-7.47 (m, 4H), 7.35-7.25 (m, 5H), 7.19-7.17 (m, 2H), 5.81 (d, 1H, J=7.1 Hz), 5.74* (d, 1H, J=5.6 Hz), 4.23 (q, 2H, J=7.0 Hz), 4.13* (q, 2H, J=7.2 Hz), 3.55 (dd, 1H, J=14.4, 4.7 Hz), 3.40-3.35* (m, 1H), 3.27-3.24* (m, 1H), 3.25 (dd, 1H, J=7.1, 5.8 Hz), 3.14* (dd, 1H, J=13.8, 5.7 Hz), 3.03-2.97 (m, 1H), 2.91* (dd, 1H, J=13.8, 8.8 Hz), 2.77 (dd, 1H, J=14.3, 10.0 Hz), 1.30 (t, 3H, J=7.0 Hz), 1.24* (t, 3H, J=7.2 Hz); $^{13}$C NMR (100 MHz, CDCl$_3$) δ 170.2, 168.7, 151.7, 138.1, 131.9, 130.9, 1294, 129.2, 129.0, 127.4, 127.1, 126.5, 124.0, 98.7, 96.7, 66.1, 62.1, 61.9, 42.8, 42.2, 41.5, 40.7, 35.5, 33.3, 15.5, 14.3, 14.2; IR (thin film) ν 3087, 3027, 2980, 1778, 1731, 1489, 1455, 1176, 1069, 1009 cm$^{-1}$; HRMS (ESI) calcd for C$_{21}$H$_{19}$BrO$_4$ [M+Na]$^+$ 437.0358, found 437.0359; 99% ee (3S,4S)-isomer as determined by HPLC (AD-H, 9:1 hexanes/i-PrOH), $t_r$ (3S,4S)=57.6 min, $t_r$ (3R,4R)=25.4 min.

Example 25

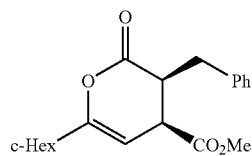

(3S,4S)-Methyl 3-benzyl-6-cyclohexyl-2-oxo-3,4-dihydro-2H-pyran-4-carboxylate (Table 1, entry 5)

Prepared according to the general procedure from 2-chloro-hydrocinnamaldehyde and (E)-methyl 4-oxo-4-cyclohexylbut-2-enoate using 0.5 mol % 1 as the catalyst in 76% yield as a single diasteromer (white solid). $[\alpha]_D^{20}$ (c 1.06, CHCl$_3$)=+178.6; mp=87-89° C.; $^1$H NMR (400 MHz, CDCl$_3$) δ 7.32-7.25 (m, 3H), 7.15-7.13 (m, 2H), 4.98 (d, 1H, J=6.9 Hz), 3.73 (s, 3H), 3.47 (dd, 1H, J=14.3, 4.8 Hz), 3.06 (t, 1H, J=6.3 hz), 2.86-2.81 (m, 1H), 2.67 (dd, 1H, J=14.3, 10.1 Hz), 2.06-2.03 (m, 1H), 1.88-1.83 (m, 5H), 1.28-1.13 (m, 5H); $^{13}$C NMR (100 MHz, CDCl$_3$) δ 171.4, 169.6, 170.3, 138.3, 129.1, 128.9, 127.0, 96.2, 52.6, 43.0, 41.0, 40.0, 33.4, 30.2, 30.0, 26.1, 26.0, 25.9; IR (thin film) ν 3086, 3027, 2929, 2854, 1773, 1737, 1452, 1436, 1155, 1056 cm$^{-1}$; HRMS (ESI) calcd for C$_{20}$H$_{24}$O$_4$ [M+Na]$^+$ 351.1566, found 351.1574; 86% ee (3S,4S)-isomer as determined by HPLC (OD-H, 9:1 hexanes/i-PrOH), $t_r$ (3S,4S)=8.5 min, $t_r$ (3R,4R)=7.7 min.

Example 26

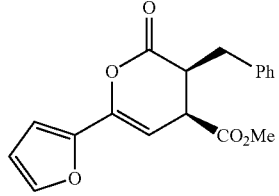 [SMILES: COC(=O)[C@H]1C=C(c2ccco2)OC(=O)[C@H]1Cc1ccccc1]

(3S,4S)-Methyl 3-benzyl-6-furanyl-2-oxo-3,4-dihydro-2H-pyran-4-carboxylate (Table 1, entry 6)

Prepared according to the general procedure from 2-chloro-hydrocinnamaldehyde and (E)-methyl 4-oxo-4-furanylbut-2-enoate using 0.5 mol % 1 as the catalyst in 94% yield as an 8:1 mixture of diastereomers (brown oil). $[\alpha]_D^{20}$ (c 1.03, CHCl$_3$)=+119.5; $^1$H NMR (400 MHz, CDCl$_3$) δ 7.41-7.29 (m, 4H), 7.18-7.16 (m, 2H), 6.67 (d, 1H, J=3.4 Hz), 6.47* (dd, 1H, J=3.2, 2.0 Hz), 6.45 (dd, 1H, J=3.2, 1.6 Hz), 5.74 (d, 1H, J=7.0 Hz), 5.70* (d, 1H, J=6.0 Hz), 3.77 (s, 3H), 3.68* (s, 3H), 3.55 (dd, 1H, J=14.3, 4.7 Hz), 3.52-3.46* (m, 1H), 3.40-3.35* (m. 1H), 3.29-3.26 (m, 1H), 3.15* (dd, 1H, J=13.6, 5.6 Hz), 3.03-2.97 (m, 1H), 2.90* (dd, 1H, J=13.6, 10.0 Hz), 2.74 (dd, 1H, J=14.3, 10.1 Hz); $^{13}$C NMR (100 MHz, CDCl$_3$) δ 170.8, 168.4, 146.5, 145.3, 143.7, 138.0, 131.6, 129.6, 129.4, 128.9, 128.8, 127.4, 127.1, 111.8, 109.0, 108.9, 96.4, 94.0, 53.6, 52.9, 52.8, 43.0, 42.6, 40.8, 40.2, 35.5, 33.4; IR (thin film) ν 3063, 3029, 2953, 1781, 1734, 1495, 1455, 1264, 1225, 1201, 1174, 1085, 1009 cm$^{-1}$; HRMS (ESI) calcd for C$_{18}$H$_{16}$O$_5$ [M+Na]$^+$ 335.0889, found 335.0890; 99% ee (3S,4S)-isomer as determined by HPLC (AD-H, 20:1 hexanes/i-PrOH), t$_r$ (3S,4S)=31.9 min, t$_r$ (3R, 4R)=22.6 min.

Example 27

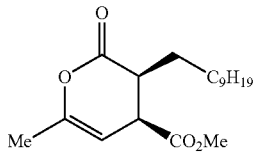

(3S,4S)-Methyl 3-decyl-6-methyl-2-oxo-3,4-dihydro-2H-pyran-4-carboxylate (Table 1, entry 7)

Prepared according to the general procedure from 2-chlorododecanal and (E)-methyl 4-oxopent-2-enoate using 0.5 mol % 1 as the catalyst in 71% yield as a single diastereomer (white solid). [α]$_D^{20}$ (c 1.20, CHCl$_3$)=+204.8; mp=40-42° C.; $^1$H NMR (400 MHz, CDCl$_3$) δ 5.09 (dd, 1H, J=6.3, 1.1 Hz), 3.68 (s, 3H), 3.30 (dt, 1H, J=6.3, 1.0 Hz), 2.66 (dd, 1H, J=7.0, 6.3 Hz), 1.90 (t, 3H, J=1.0 Hz), 1.35-1.24 (m, 18H), 0.86 (t, 3H, J=6.8 Hz); $^{13}$C NMR (100 MHz, CDCl$_3$) δ 171.4, 169.8, 152.3, 98.4, 52.5, 41.5, 40.6, 32.0, 29.7, 29.7, 29.5, 29.5, 27.3, 27.2, 22.8, 18.9, 14.3; IR (thin film) ν 3062, 2925, 2854, 1777, 1740, 1463, 1436, 1383, 1167, 1142 cm$^{-1}$; HRMS (ESI) calcd for C$_{18}$H$_{30}$O$_4$ [M+Na]$^+$ 333.1996, found 333.2021; >99% ee (3S,4S)-isomer as determined by HPLC (OD-H, 20:1 hexanes/i-PrOH), t$_r$ (3S,4S)=6.7 min, t$_r$ (3R, 4R)= 6.0 min.

Example 28

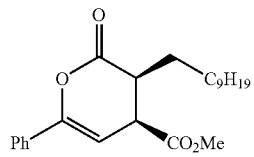

(3S,4S)-Methyl 3-decyl-6-phenyl-2-oxo-3,4-dihydro-2H-pyran-4-carboxylate (Table 1, entry 8)

Prepared according to the general procedure from 2-chlorododecanal and (E)-methyl 4-oxo-4-phenylbut-2-enoate using 0.5 mol % 1 as the catalyst in 90% yield as a single diastereomer (white solid). [α]$_D^{20}$ (c 1.15, CHCl$_3$)=+154.3; mp=108-111° C.; $^1$H NMR (400 MHz, CDCl$_3$) δ 7.66-7.63 (m, 2H), 7.40-7.37 (m, 3H), 5.89 (d, 1H, J=6.4 Hz), 3.73 (s, 3H), 3.57 (t, 1H, J=6.3 Hz), 2.76 (q, 1H, J=6.3 Hz), 2.04 (t, 1H, J=7.0 Hz), 1.47-1.26 (m, 18H), 0.88 (t, 3H, J=6.8 Hz); $^{13}$C NMR (100 MHz, CDCl$_3$) δ 171.0, 169.5, 152.4, 132.0, 129.8, 128.8, 125.0, 97.9, 52.7, 41.9, 40.7, 32.1, 29.8, 29.8, 29.6, 29.6, 27.4, 27.3, 22.9, 14.4; IR (thin film) ν 3062, 2916, 2846, 1758, 1722, 1464, 1339, 1176, 1115 cm$^{-1}$; HRMS (ESI) calcd for C$_{23}$H$_{32}$O$_4$ [M+Na]$^+$ 395.2192, found 395.2192; 99% ee (3S,4S)-isomer as determined by HPLC (AD-H, 9:1 hexanes/i-PrOH), t$_r$ (3S,4S)=7.2 min, t$_r$ (3R,4R)= 10.3 min.

Example 29

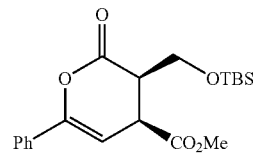 [SMILES: COC(=O)[C@H]1C=C(c2ccccc2)OC(=O)[C@H]1CO[Si](C)(C)C(C)(C)C]

(3R,4S)-Methyl 3-((tert-butyldimethylsilyloxy)methyl)-6-phenyl-2-oxo-3,4-dihydro-2H-pyran-4-carboxylate (Table 1, entry 9)

Prepared according to the general procedure from 3-(tert-butyldimethylsilyloxy)-2-chloropropanal and (E)-methyl 4-oxo-4-phenylbut-2-enoate using 0.5 mol % 1 as the catalyst in 80% yield as a 3:1 mixture of diastereomers. The diastereomers were separated by silica gel chromatography (15:1 hexanes/EtOAc) and characterized separately. [α]$_D^{20}$ (c 1.07, CHCl$_3$)=+133.6; $^1$H NMR (400 MHz, CDCl$_3$) δ 7.65-7.62 (m, 2H), 7.40-7.37 (m, 3H), 5.94 (d, 1H, J=7.1 Hz), 4.26 (dd, 1H, J=10.6, 5.7 Hz), 3.88 (t, 1H, J=10.1 Hz), 3.76 (dd, 1H, J=13.7, 7.4 Hz), 3.72 (s, 3H), 3.08-3.02 (m, 1H), 0.89 (s, 9H), 0.07 (s, 3H), 0.06 (s, 3H); $^{13}$C NMR (100 MHz, CDCl$_3$) δ 170.9, 167.7, 152.5, 131.9, 129.8, 128.8, 125.0, 98.1, 59.7, 52.6, 42.5, 38.7, 25.9, 18.4, −5.4, −5.6; IR (thin film) ν 3062, 2953, 2929, 2886, 2857, 1778, 1739, 1254, 1197, 1176 cm$^{-1}$; HRMS (EI) calcd for C$_{20}$H$_{25}$O$_5$Si [M]$^+$ 376.1706, found 376.1697; 97% ee (3R,4S)-isomer as determined by HPLC (AD-H, 100:1 hexanes/i-PrOH), t$_r$ (3R,4S)=21.8 min, t$_r$ (3S, 4R)=15.2 min.

Example 30

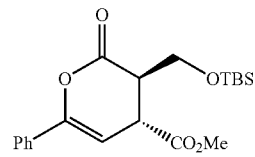 [SMILES: COC(=O)[C@@H]1C=C(c2ccccc2)OC(=O)[C@H]1CO[Si](C)(C)C(C)(C)C]

(3R,4R)-Methyl 3-((tert-butyldimethylsilyloxy)methyl)-6-phenyl-2-oxo-3,4-dihydro-2H-pyran-4-carboxylate $^1$H NMR (400 MHz, CDCl$_3$) δ 7.64-7.61 (m, 2H), 7.40-7.37 (m, 3H), 5.75 (d, 1H, J=7.1 Hz), 4.05 (dd, 1H, J=10.1, 6.3 Hz), 3.89 (dd, 1H, J=10.1, 4.2 Hz), 3.80-3.77 (m, 1H), 3.78 (s, 3H), 3.30-3.25 (m, 1H), 0.87 (s, 9H), 0.052 (s, 3H), 0.048 (s, 3H); $^{13}$C NMR (100 MHz, CDCl$_3$) δ 172.2, 167.6, 150.5, 131.9, 129.7, 128.7, 125.0, 97.2, 61.0, 52.9, 43.2, 39.5, 26.0, 18.5, −5.4; IR (thin film) ν 3062, 2953, 2929, 2886, 2857, 1778, 1739, 1254, 1197, 1176 cm$^{-1}$; HRMS (EI) calcd for C$_{20}$H$_{25}$O$_5$Si [M]$^+$ 376.1706, found 376.1697; 97% ee (3R, 4R)-isomer as determined by HPLC (AD-H, 100:1 hexanes/i-PrOH), t$_r$ (3R,4R)=24.6 min, t$_r$ (3S,4S)=17.1 min.

Example 31

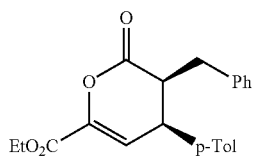

(4S,5S)-Ethyl 5-benzyl-6-oxo-4-para-tolyl-5,6-dihydro-4H-pyran-2-carboxylate (Table 2, entry 1)

Prepared according to the general procedure from 2-chloro-hydrocinnamaldehyde and (E)-ethyl 2-oxo-4-p-tolylbut-3-enoate using 2 mol % 1 as the catalyst in 74% yield as a single diastereomer (colorless oil). [α]$_D^2$ (c 1.02, CHCl$_3$)=+310.3; $^1$H NMR (400 MHz, CDCl$_3$) δ 7.32-7.24 (m, 3H), 7.16-7.07 (m, 4H), 6.93-6.91 (m, 2H), 6.65 (d, 1H, J=6.8 Hz), 4.30 (q, 1H, J=7.1 Hz), 3.58 (t, 1H, J=6.7 Hz), 3.29-3.23 (m, 2H), 2.41 (dd, 1H, J=15.8, 10.9 Hz), 2.35 (s, 3H), 1.33 (t, 3H, J=7.1 Hz); $^{13}$C NMR (100 MHz, CDCl$_3$) δ 168.9, 160.7, 142.1, 138.3, 132.8, 130.0, 129.1, 128.8, 128.4, 126.9, 118.9, 62.1, 45.0, 40.3, 32.1, 21.3, 14.3; IR (thin film) ν 3062, 3027, 2982, 2925, 1776, 1732, 1316, 1267, 1106 cm$^{-1}$; HRMS (ESI) calcd for C$_{22}$H$_{22}$O$_4$ [M+Na]$^+$ 373.1410, found 373.1409; 97% ee (4S,5S)-isomer as determined by HPLC (AD-H, 9:1 hexanes/i-PrOH), t$_r$ (4S,5S)=21.7 min, t$_r$ (4R,5R)=13.4 min.

Example 32

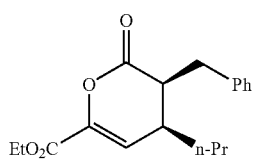

(4S,5S)-Ethyl 5-benzyl-6-oxo-4-propyl-5,6-dihydro-4H-pyran-2-carboxylate (Table 2, entry 2)

Prepared according to the general procedure from 2-chloro-hydrocinnamaldehyde and (E)-ethyl 2-oxohept-3-enoate using 2 mol % 1 as the catalyst in 84% yield as a single diastereomer (white solid). [α]$_D^{20}$ (c 1.01, CHCl$_3$)=+115.3; mp=77-81° C.; $^1$H NMR (400 MHz, CDCl$_3$) δ 7.32-7.17 (m, 5H), 6.57 (d, 1H, J=6.5 Hz), 4.28 (dq, 2H, J=7.2, 1.5 Hz), 3.33 (dd, 1H, J=14.3, 5.5 Hz), 2.95-2.90 (m, 1H), 2.74 (dd, 1H, J=14.3, 9.5 Hz), 2.42-2.39 (m, 1H), 1.62-1.58 (m, 2H), 1.42-1.20 (m, 5H), 0.88 (t, 3H, J=7.1 Hz); $^{13}$C NMR (100 MHz, CDCl$_3$) δ 169.7, 160.7, 142.2, 138.4, 128.9, 126.9, 120.5, 62.0, 44.4, 33.2, 32.0, 31.1, 20.0, 14.4, 14.3; IR (thin film) ν 3062, 3027, 2959, 2924, 1776, 1736, 1455, 1370, 1262, 1109 cm$^{-1}$; HRMS (ESI) calcd for C$_{18}$H$_{22}$O$_4$ [M+Na]$^+$ 325.1410, found 325.1398; 98% ee (4S,5S)-isomer as determined by HPLC (AS-H, 9:1 hexanes/i-PrOH), t$_r$ (4S,5S)=18.9 min, t$_r$ (4R,5R)=11.9 min.

Example 33

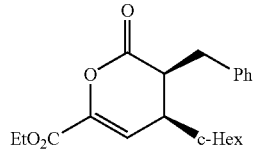

(4S,5S)-Ethyl 5-benzyl-6-oxo-4-cyclohexyl-5,6-dihydro-4H-pyran-2-carboxylate (Table 2, entry 3)

Prepared according to the general procedure from 2-chloro-hydrocinnamaldehyde and (E)-ethyl 4-cyclohexyl-2-oxobut-3-enoate using 2 mol % 1 as the catalyst in 85% yield as a single diastereomer (colorless oil). [α]$_D^{20}$ (c 1.20, CHCl$_3$)=+83.5; $^1$H NMR (400 MHz, CDCl$_3$) δ 7.33-7.21 (m, 5H), 6.48 (d, 1H, J=6.5 Hz), 4.30 (dq, 1H, J=7.2, 1.8 Hz), 3.38 (dd, 1H, J=14.3, 5.7 Hz), 2.97-2.91 (m, 1H), 2.77 (dd, 1H, J=14.3, 9.1 Hz), 2.45-2.41 (m, 1H), 1.76-1.62 (m, 5H), 1.47-1.44 (m, 1H), 1.34 (t, 3H, J=7.2 Hz), 1.27-1.06 (m, 4H), 0.93-0.89 (m, 1H); $^{13}$C NMR (100 MHz, CDCl$_3$) δ 170.4, 160.7, 142.8, 138.6, 128.9, 126.9, 117.6, 62.0, 43.0, 39.4, 37.7, 31.7, 31.4, 27.2, 26.8, 26.1, 14.3; IR (thin film) ν 3520, 3086, 3028, 2981, 2928, 2853, 1770, 1731, 1660, 1453, 1369, 1309, 1262, 1120, 1094, 1013 cm$^{-1}$; HRMS (ESI) calcd for C$_{21}$H$_{26}$O$_4$ [M+Na]$^+$ 365.1723, found 365.1721; 95% ee (4S, 5S)-isomer as determined by HPLC (AS-H, 20:1 hexanes/i-PrOH), t$_r$ (4S,5S)=19.1 min, t$_r$ (4R,5R)=15.7 min.

Example 34

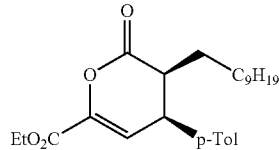

(4S,5S)-Ethyl 5-decyl-6-oxo-4-para-tolyl-5,6-dihydro-4H-pyran-2-carboxylate (Table 2, entry 4)

Prepared according to the general procedure from 2-chlorododecanal and (E)-ethyl 2-oxo-4-p-tolylbut-3-enoate using 2 mol % 1 as the catalyst in 70% yield as a single diastereomer (colorless oil). [α]$_D^{20}$ (c 1.31, CHCl$_3$)=+154.3; $^1$H NMR (400 MHz, CDCl$_3$) δ 7.32-7.24 (m, 3H), 7.12 (d, 2H, J=8.1 Hz), 6.99 (d, 2H, J=8.1 hz), 6.70 (d, 1H, J=6.5 Hz), 4.32 (q, 1H, J=7.2 Hz), 3.77 (t, 1H, J=6.8 Hz), 2.81 (q, 1H, J=6.8 Hz), 2.33 (s, 3H), 1.72-1.63 (m, 2H), 1.37-1.14 (m, 19H), 0.88 (t, 3H, J=6.8 Hz); $^{13}$C NMR (100 MHz, CDCl$_3$) δ 169.2, 160.8, 142.3, 138.1, 133.1, 130.0, 128.1, 118.6, 62.1, 43.6, 41.2, 32.1, 29.7, 29.7, 29.5, 27.3, 26.4, 22.9, 21.3, 14.4, 14.3; IR (thin film) ν 3027, 2925, 2854, 1777, 1739, 1659, 1464, 1370, 1316, 1260, 1104 cm$^{-1}$; HRMS (EI) calcd for C$_{25}$H$_{36}$O$_4$ [M]$^+$ 400.2614, found 400.2613; 99% ee (4S,5S)-isomer as determined by HPLC(OD-H, 20:1 hexanes/i-PrOH), $t_r$ (4S,5S)= 8.0 min, $t_r$ (4R,5R)=9.2 min.

Example 35

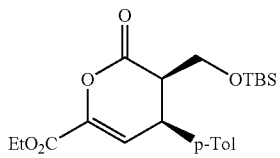

(4S,5R)-Ethyl 5-((tert-butyldimethylsilyloxy)methyl)-6-oxo-4-para-tolyl-5,6-dihydro-4H-pyran-2-carboxylate (Table 2, entry 5)

Prepared according to the general procedure from 3-(tert-butyldimethylsilyloxy)-2-chloropropanal and (E)-ethyl 2-oxo-4-p-tolylbut-3-enoate using 2 mol % 1 as the catalyst in 83% yield as a single diastereomer (white solid). $[\alpha]_D^2$ (c 1.27, CHCl$_3$)=+244.6; mp=60-61° C.; $^1$H NMR (400 MHz, CDCl$_3$) δ 7.32-7.24 (m, 3H), 7.12 (d, 2H, J=8.1 Hz), 6.99 (d, 2H, J=8.1 hz), 6.70 (d, 1H, J=7.5 Hz), 4.32 (q, 1H, J=7.2 Hz), 3.77 (t, 1H, J=6.8 Hz), 2.81 (q, 1H, J=6.8 Hz), 2.33 (s, 3H), 1.72-1.63 (m, 2H), 1.37-1.14 (m, 19H), 0.88 (t, 3H, J=6.8 Hz); $^{13}$C NMR (100 MHz, CDCl$_3$) δ 167.3, 160.7, 142.6, 138.2, 132.0, 129.8, 128.5, 118.9, 62.1, 58.7, 45.8, 38.3, 26.0, 21.3, 18.3, 14.4, −5.3, −5.4; IR (thin film) v 3027, 2953, 2929, 2857, 1776, 1740, 1658, 1471, 1370, 1317, 1262, 1084 cm$^{-1}$; HRMS (EI) calcd for C$_{25}$H$_{36}$O$_4$ [M-Bu]$^+$ 347.1315, found 347.1305; 95% ee (4S,5R)-isomer as determined by HPLC (AD-H, 100:1 hexanes/i-PrOH), $t_r$ (4S,5R)=8.5 min, $t_r$ (4R, 5S)=10.0 min.

Preparation of Starting Materials.

All the racemic and chiral 2-chloroaldehydes were prepared according to the previous literature procedures. The substituted 4-oxo-enoates (Table 1, entry 1~9) were prepared as previously reported via one-pot oxidation-stabilized Wittig reactions to provide the desired enoates.

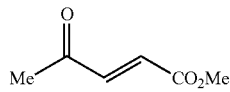

(E)-Methyl 4-oxopent-2-enoate $^1$HNMR (400 MHz, CDCl$_3$) δ 6.96 (d, 1H, J=16.1 Hz), 6.60 (d, 1H, J=16.1 hz), 3.75 (s, 31-1), 2.30 (s, 311); $^{13}$C NMR (100 MHz, CDCl$_3$) δ 197.7, 166.0, 140.2, 131.1, 52.5, 28.2; MS (EI) C$_6$H$_8$O$_3$[M]$^+$ 128.

The β,γ-unsaturated α-ketoesters were prepared by reacting ethyl triphenylphos-phoranylidenepyruvate with corresponding aldehydes.

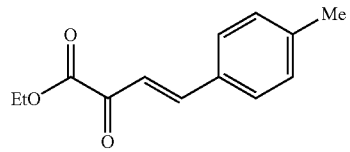 [SMILES: CCOC(=O)C(=O)/C=C/c1ccc(C)cc1]

(E)-Ethyl 2-oxo-4-para-tolylbut-3-enoate $^1$H NMR (400 MHz, CDCl$_3$) δ 7.85 (d, 1H, J=14.1 Hz), 7.54 (d, 2H, J=8.0 Hz), 7.33 (d, 1H, J=16.1 Hz), 7.25 (d, 2H, J=8.0 hz), 4.39 (q, 2H, J=7.1 Hz), 2.40 (s, 3H), 1.41 (t, 3H, J=7.1 Hz); $^{13}$C NMR (100 MHz, CDCl$_3$) δ 183.0, 162.4, 148.7, 142.6, 131.4, 130.0, 129.2, 119.6, 62.6, 21.7, 14.2; HRMS (EI) calcd for C$_{13}$H$_{14}$O$_3$ [M]$^+$ 218.0943, found 218.0951.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A compound having the formula:

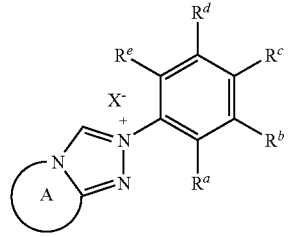

wherein
A is a ring system selected from substituted or unsubstituted cycloalkyl and substituted or unsubstituted heterocycloalkyl;
$R^a$ and $R^e$ are members independently selected from H, halogen, nitro, cyano, substituted or unsubstituted alkyl and substituted or unsubstituted heteroalkyl;
with the proviso that $R^a$ and $R^e$ cannot both be H, and with the further proviso that $R^a$ and $R^e$ cannot both be halogen if $R^b$, $R^c$ and $R^d$ are halogen;
$R^b$, $R^c$ and $R^d$ are members independently selected from H, halogen, nitro, cyano, substituted or unsubstituted alkyl and substituted or unsubstituted heteroalkyl and
$X^-$ is an anion.

2. The compound according to claim 1 wherein said compound has a structure according to the following formula:

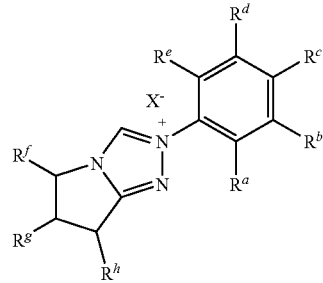

wherein each $R^f$, $R^g$ and $R^h$ are members individually selected from is a member selected from H, substituted or unsubstituted alkyl and substituted or unsubstituted heteroalkyl,
with the proviso that $R^f$ and $R^g$ can be optionally joined to form a five to seven membered ring;
with the proviso that $R^g$ and $R^h$ can be optionally joined to form a five to seven membered ring;
wherein said five to seven membered ring is a member selected from substituted or unsubstituted cycloalkyl, substituted or unsubstituted heterocycloalkyl, substituted or unsubstituted aryl and substituted or unsubstituted heteroaryl.

3. The compound according to claim 2 wherein $R^f$, $R^g$ and $R^h$ are H.

4. The compound according to claim 1 wherein said compound has a structure according to the following formula:

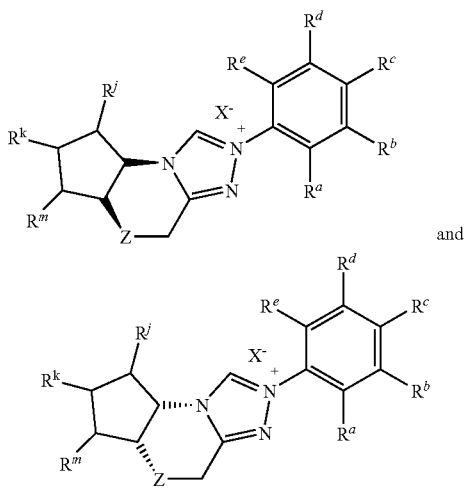

and wherein Z is a member selected from O and S;

wherein each $R^j$, $R^k$ and $R^m$ are members individually selected from is a member selected from H, substituted or unsubstituted alkyl and substituted or unsubstituted heteroalkyl, with the proviso that $R^j$ and $R^k$ can be optionally joined to form a five to seven membered ring;

with the proviso that $R^k$ and $R^m$ can be optionally joined to form a five to seven membered ring;

wherein said five to seven membered ring is a member selected from substituted or unsubstituted cycloalkyl, substituted or unsubstituted heterocycloalkyl, substituted or unsubstituted aryl and substituted or unsubstituted heteroaryl.

5. The compound according to claim 1 wherein said compound has a structure according to the following formula:

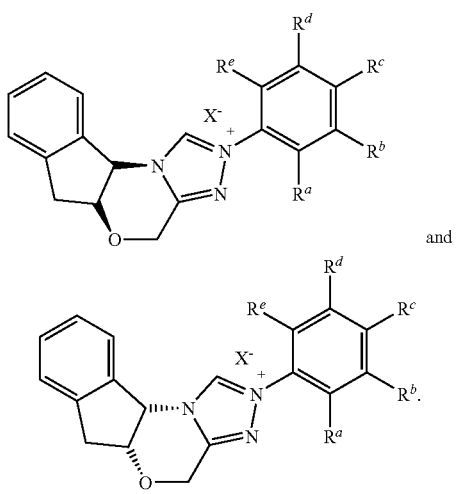

and

6. The compound according to claim 1 wherein $R^a$, $R^c$ and $R^e$ are each methyl.

7. The compound according to claim 1 wherein $R^b$ is H.

8. The compound according to claim 1 wherein $R^d$ is H.

9. The compound according to claim 1 wherein $R^b$ and $R^d$ are H.

10. The compound according to claim 1 wherein if one member of $R^a$ and $R^e$ is $C_1$-$C_6$ alkyl, then the other member is H.

11. The compound according to claim 10 wherein $R^e$ is a member selected from methyl, ethyl, propyl, isopropyl, butyl, isobutyl, pentyl, isopentyl and hexyl.

12. The compound according to claim 1 wherein $R^a$ and $R^e$ are each independently selected from $C_1$-$C_6$ alkyl.

13. The compound according to claim 1 wherein $R^e$ is $C_1$-$C_6$ alkyl.

14. The compound according to claim 1 wherein $R^a$, $R^c$ and $R^e$ are each methyl.

15. The compound according to claim 1 wherein $R^d$ is substituted or unsubstituted heteroalkyl.

16. The compound according to claim 15 wherein $R^d$ is substituted or unsubstituted methoxy.

17. The compound according to claim 1 wherein $R^b$ and $R^d$ are H.

18. The compound according to claim 1 wherein said compound is chiral.

19. The compound according to claim 1 wherein said compound has a formula selected from:

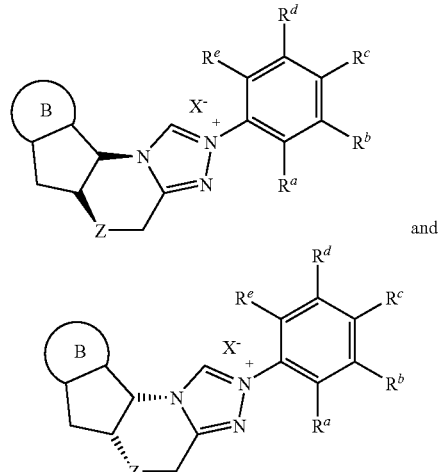

and wherein

B is a ring system selected from substituted or unsubstituted aryl and substituted or unsubstituted heteroaryl; and Z is a member selected from O and S.

20. The compound according to claim 19 wherein B is substituted or unsubstituted phenyl.

21. The compound according to claim 20 wherein said compound has a formula which is a member selected from:

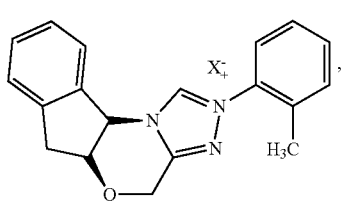

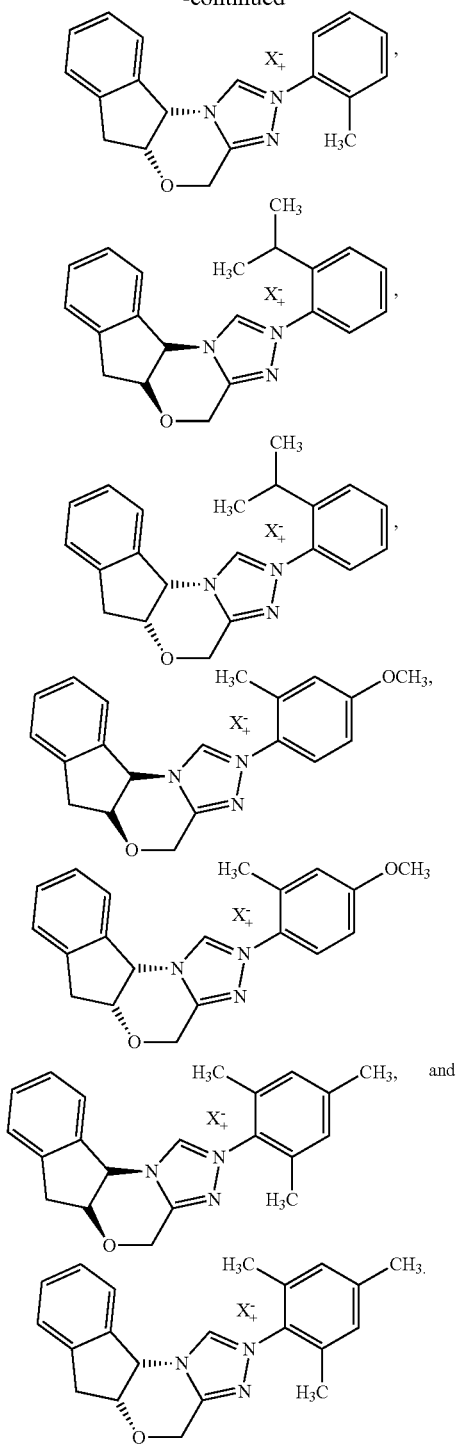

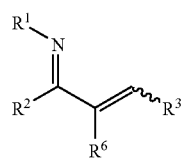

22. A mixture comprising:
(a) a compound according to claim 1; and
(b) an aldehyde.

23. The mixture according to claim 2, further comprising:
(c) an enone.

24. The mixture according to claim 22, further comprising:
(c) an imine.

25. The mixture according to claim 24 wherein said imine has the formula:

$R^1$ is a member selected from $C(O)R^7$, $S(O)_2R^7$, $P(O)(R^7)_2$ and $P(O)(OR^7)_2$ wherein
    each $R^7$ is a member independently selected from substituted or unsubstituted alkyl, substituted or unsubstituted heteroalkyl, substituted or unsubstituted aryl and substituted or unsubstituted heteroaryl;
$R^2$ and $R^6$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl; and
$R^3$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

26. A method for preparing a chiral heterocycle, having a formula which is a member selected from:

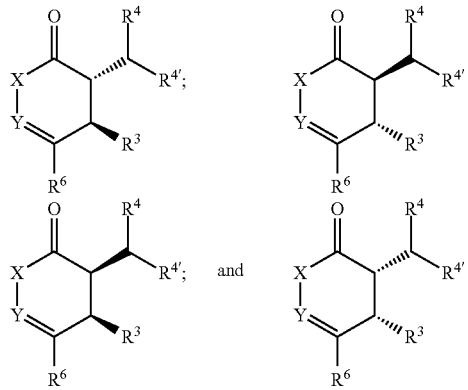

wherein
  X is a member selected from O and $NR^1$
  wherein
    $R^1$ is a member selected from $C(O)R^7$, $S(O)_2R^7$, $P(O)(R^7)_2$ and $P(O)(OR^7)_2$
    wherein
      each $R^7$ is a member independently selected from substituted or unsubstituted alkyl, substituted or unsubstituted heteroalkyl, substituted or unsubstituted aryl, substituted or unsubstituted heteroaryl and substituted or unsubstituted heterocycloalkyl;
  Y is a member selected from $CR^2$ and $NO^-$
  $R^2$, $R^4$, $R^{4'}$ and $R^6$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl; and
  $R^3$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl; and said method comprising:

(a) contacting an imine having the formula:

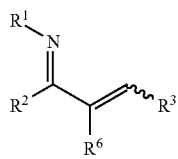

and an aldehyde having the formula:

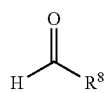

wherein
R⁸ is a member selected from substituted or unsubstituted unsaturated alkyl, substituted or unsubstituted unsaturated heteroalkyl and substituted or unsubstituted heterocycloalkyl with an organic catalyst according to claim 1:

under conditions appropriate to prepare said chiral heterocycle.

27. The method according to claim 26 wherein said chiral heterocycle has a formula which is a member selected from:

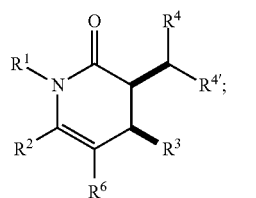 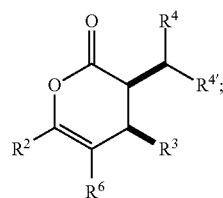

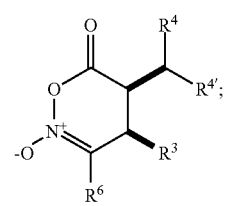 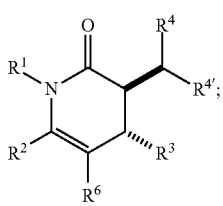

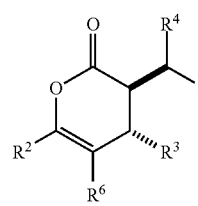; and 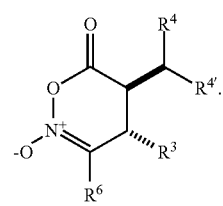.

28. The method according to claim 1 wherein $R^a$, $R^c$ and $R^e$ are each methyl.

29. The method according to claim 1 wherein said organic catalyst has a formula selected from:

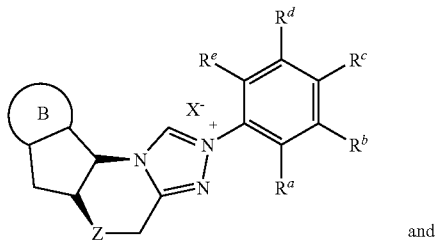

and

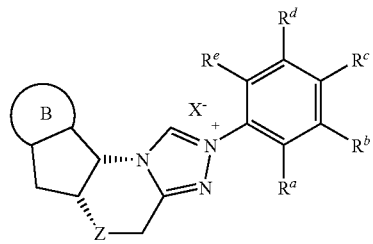

wherein
B is a ring system selected from substituted or unsubstituted aryl and substituted or unsubstituted heteroaryl; and Z is a member selected from O and S.

30. The method according to claim 29 wherein B is substituted or unsubstituted phenyl.

31. The method according to claim 1 wherein said organic catalyst has a formula which is a member selected from:

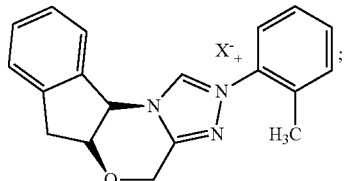

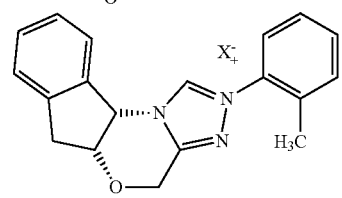

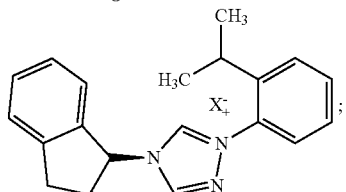

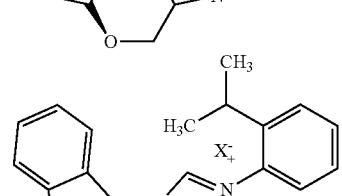

77

-continued

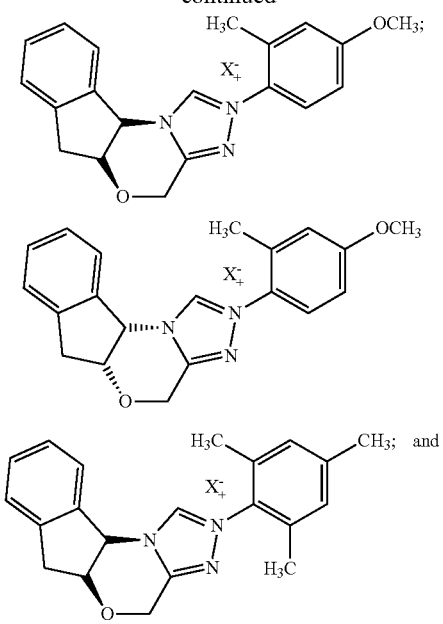

78

-continued

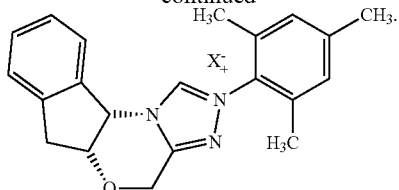

32. The method according to claim 1 wherein said method further comprises:
  (b) contacting said imine with a tertiary amine.
33. The method according to claim 32 wherein said amine is a member selected from diisopropylethylamine, spartene, imidazole, 4,4-dimethylamino pyridine, triethylamine, dicyclohexylethylamine, 1,8-diazabicylcoundec-7-ene (DBU) and combinations thereof.
34. The method according to claim 1 wherein said contacting occurs in an organic solvent.
35. The method according to claim 34 wherein said organic solvent is a member selected from toluene, THF, DMF, EtOAc, dichloromethane, dicholorethane, benzene, dioxane, tert-butyl alcohol, DMSO, acetonitrile, chloroform, xylenes and mixtures thereof.

* * * * *